US007597895B2

(12) United States Patent
Huang et al.

(10) Patent No.: US 7,597,895 B2
(45) Date of Patent: Oct. 6, 2009

(54) SIGNAL PEPTIDES, NUCLEIC ACID MOLECULES AND METHODS FOR TREATMENT OF CARIES

(75) Inventors: Yi-Chen Cathy Huang, Toronto (CA); Celine Levesque, Toronto (CA); Dennis G. Cvitkovitch, Oakville (CA)

(73) Assignee: The Governing Council of the University of Toronto, Toronto (CA)

( * ) Notice: Subject to any disclaimer, the term of this patent is extended or adjusted under 35 U.S.C. 154(b) by 394 days.

(21) Appl. No.: 11/005,636

(22) Filed: Dec. 6, 2004

(65) Prior Publication Data

US 2005/0152853 A1    Jul. 14, 2005

Related U.S. Application Data

(63) Continuation-in-part of application No. 09/833,017, filed on Apr. 10, 2001, now Pat. No. 6,923,962.

(60) Provisional application No. 60/269,949, filed on Feb. 20, 2001.

(51) Int. Cl.
*A61K 39/09* (2006.01)
*C07K 14/00* (2006.01)
*C07H 21/04* (2006.01)
*C12P 21/04* (2006.01)

(52) U.S. Cl. ............... 424/244.1; 424/184.1; 530/300; 435/69.7; 536/23.7

(58) Field of Classification Search ............. 424/244.1, 424/165.1, 181.1, 184.1, 185.1, 50, 54, 58; 530/300, 350, 388.2, 391.1; 536/23.5, 23.7; 435/69.5, 69.7; 514/12
See application file for complete search history.

(56) References Cited

U.S. PATENT DOCUMENTS

| 4,150,116 A | 4/1979 | Taubman et al. |
| 4,521,513 A * | 6/1985 | Russell ...................... 435/71.2 |
| 4,828,985 A | 5/1989 | Self |
| 4,950,480 A | 8/1990 | Barber |
| 5,073,494 A | 12/1991 | Heyneker |
| 5,085,862 A | 2/1992 | Klein |
| 5,124,147 A | 6/1992 | Wissner |
| 5,147,643 A | 9/1992 | Heyneker |
| 5,194,254 A | 3/1993 | Barber |
| 5,221,618 A | 6/1993 | Klein |
| 5,225,331 A | 7/1993 | Lacroix |
| 5,244,657 A | 9/1993 | Klein |
| 5,332,583 A | 7/1994 | Klein |
| 5,358,868 A | 10/1994 | Klein |
| 5,433,945 A | 7/1995 | Klein |
| 5,496,705 A | 3/1996 | Sugano |
| 5,500,345 A | 3/1996 | Soe |
| 5,501,988 A | 3/1996 | Kobayashi |
| 5,503,987 A | 4/1996 | Wagner |
| 5,510,241 A | 4/1996 | Thorns |
| 5,512,282 A | 4/1996 | Krivan |
| 5,530,102 A | 6/1996 | Gristina et al. |
| 5,543,302 A | 8/1996 | Boguslawski |
| 5,591,628 A | 1/1997 | Baek |
| 5,665,356 A | 9/1997 | De Burgh Bradle |
| 5,667,781 A | 9/1997 | Trowbridge |
| 5,679,352 A | 10/1997 | Chong |
| 5,683,693 A | 11/1997 | Noelle |
| 5,688,657 A | 11/1997 | Tsang |
| 5,688,681 A | 11/1997 | Kim |
| 5,695,931 A | 12/1997 | Labigne |
| 5,714,372 A | 2/1998 | Vehar |
| 5,736,337 A | 4/1998 | Avruch |
| 5,767,075 A | 6/1998 | Avruch |
| 5,801,233 A | 9/1998 | Haselkorn |
| 5,837,472 A | 11/1998 | Labigne |
| 5,851,788 A | 12/1998 | Fukuda |
| 6,024,958 A | 2/2000 | Lehner et al. |

OTHER PUBLICATIONS

Costerton and Lewandowski, 1997 The Biofilm Lifestyle, Adv. Dent Res., 11:192-195.
Christensen et al. 1998 Establishment of New Genetic Traits in a Microbial Biofilm Community, Appl Environ Microbial, 64:2247-2255.
Finlay, B.B., Falkow, S. Common Themes in Microbial Pathogenicity Revisited, Microbiol Molec Rev. 61:136-169.
Davies, D.G., Geesey, G.G. Regulation of the Alginate Biosynthesis Gene algC in *Pseudomonas aeruginosa* during Biofilm Development in Continuous Culture, Appl Environ Microbiol, 61:860-867.
Aspiras, M.B., R. P. Ellen, and D.G. Cvitkovitch. 2004 ComX Activity of *Streptococcus mutans* Growing in Biofilms. FEMS Microbiol. Lett. 238:167-174.
Balaban, N., L.V. Collins, J.S. Cullor, E.B. Hume, E. Medina-Acosta, O. Vieira Da Motta, R. C'Callaghan, PV.V Rossitto, M.E. Shirtliff, L. Serafim De Silveira, A. Tarkowski, and J.V. Torres. 2000. Prevention of diseases caused by *Staphylococcus aureus* using the peptide RIP. Peptides 21:1301-1311.
Banas, J.A. 2004. Virulence Properties of *Streptococcus mutans*. Front Bioscience 9:1267-1277.
Buckley, N.D., L.N. Lee, and D.J. Leblanc. 1995. Use of a Novel Mobilizable Vector to Inactivate the scrA Gene of *Streptococcus sobrinus* by Allelic Replacement. J. Bacteriol. 177:5028-5034.
Cvitkovitch, D.G., Y. Li, and R. P. Ellen. 2003. Quorumn-sensing and biofilm formation in streptococcal infections. J. Clin. Invest. 112:1626-1632.

(Continued)

*Primary Examiner*—Robert B Mondesi
*Assistant Examiner*—Padma V Baskar
(74) *Attorney, Agent, or Firm*—Brian R. Dorn; Merchant & Gould P.C.

(57) ABSTRACT

Compounds that competitively inhibit binding of CSP to *S. mutans* histidine kinase are provided. The compounds are preferably a peptide or an antibody, and are preferably a derivative of [SEQ ID NO:2], a fragment of [SEQ ID NO:2] or a derivative of a fragment of [SEQ ID NO:2]. Methods of making these compounds and their use for inhibiting the growth of *S. mutans*, for inhibiting dental caries, and for improving dental health are also disclosed.

15 Claims, 24 Drawing Sheets

OTHER PUBLICATIONS

Davies, D.G., M.R. Parsek, J.P. Pearson, B.H. Iglewski, J.W. Costerton, E.P. Greenberg. 1998. The involvement of cell-to-cell signals in the development of a bacterial biofilm. Science 280:295-298.

Dunny, G.M., and B.A.B. Leonard. 1997 Cell-cell Communication in Gram-Positive Bacteria. Annu. Rev. Microbiol 51:527-564.

Eberl, L., S. Molin, and M. Givskov. 1999. Surface Motility of *Serratia liquefaciens* MG1. J. Bacteriol. 181:1703-1712.

Havarstein, L.S., S., G. Gaustad, I.F. Nes, and D.A. Morrison. 1996. Identification of the Streptococcal competence pheromone receptor. Mol. Microbiol. 21:863-869.

Hentzer, M., and M. Givskov. 2003. Pharmacological Inhibition of Quorum Sensing for the Treatment of Chronic Bacterial Infections. J. Clin. Invest. 112:1300-1307.

Jefferson, K.K. 2004. What Drives Bacteria to Produce a Biofilm? FEMS Microbial. Rev. 236:163-173.

Ji, G., R.C. Beavis, and R.P. Novick. 1995. Cell Density Control of *Staphylococcal Virulence* Mediated by an Octapeptide Pheromone. Proc. Natl. Acad. Sci. USA. 92:12055-12059.

Lau, P.C. Y., C.K. Sung, J.H. Lee, D.A. Morrison, and D.G. Cvitkovitch. 2002. PCR ligation Mutagenesis in Transformable Streptococci; Application and Efficiency. J. Microbial. Methods 49:193-205.

Lee, M.S., and D.A. Morrison. 1999 Identification of a New Regulator in *Streptococcus pneumonia* Linking Quorum Sensing to Competence for Genetic Transformation. J. Bacteriol. 181:5004-5016.

Lewis, K. 2001. Riddle of Biofilm Resistance. Antimicrob. Agents Chemother. 45:999-1007.

Li, Y., N. Tang, M.B. Aspiras, P.C.Y. Lau, J.H. Lee, R.P. Ellen, and D.G. Cvitkovitch. 2002. A Quorum-Sensing Signaling System Essential for Genetic Competence in *Streptococcus mutans* is Involved in Biofilm Formation. J. Bacteriol 184:2699-2708.

Luo, P., H. Li, and D.A. Morrison 2003 ComX is a Unique Link Between Multiple Quorum Sensing Outputs and Competence in *Streptococcums pneumonia*. Mol. Microbiol. 50:623-633.

Marsh, P.D. 2004. Dental Plaque as Microbial Biofilm. Caries Res. 38:204-211.

Mayville, P., G. Ji, R. Beavis, H. Yang, M. Goger, R.P. Novick, and T.W. Muir. 1999 Structure-Activity Analysis of Synthetic Autoinducing Thiolactone Peptides from *Staphylococcus auerus* Responsible for Virulence. Proc. Natl. Acad. Sci. USA 96:1218-1223.

Mitchell, T.J. 2003 The Pathogenesis of Streptococcal Infections: From Tooth Decay to Meningitis. Nat. Rev. Microbiol 1:219-230.

Oggioni, M.R., F. Iannelli, S. Ricci, D. Chiavolini, R. Parigi, C. Trapetti, J.-P Claverys, and G. Pozzi. 2004 Antibacterial Activity of a Competence-Stimulating Peptide in Experimental Sepsis caused by *Streptococcus pneumoniae* Antimicrob. Agents Chemother 48:4725-4732.

Otto, M., R. Sussmuth, G. Vuong, G. Jung, and F. Gotz. 1999 Inhibition of Virulence Factor Expression in *Staphylococcus aureus* by the *Staphylococcus epidermis* agr Pheromone and Derivatives FEBS Lett. 450:257-262.

Peterson, F.C., and A.A. Scheie. 2000 Genetic Transformation in *Streptococcus mutans* Requires a Peptide Secretion-Like Apparatus. Oral Microbiol. Immunol. 15:329-34.

Shapiro, J.A. 1998. Thinking About Bacterial Populations as Multicellular Organisms. Annu. Rev. Microbiol 52:81-104.

Bassler, B.L. 2002. Small talk. Cell to cell Communication in Bacteria. Cell 109:421-424.

Benet et al., 1990, 'Pharmacokinetics: The dynamics of Drug Absorption, Distribution, and Elimination,' in *The Pharmacological Basis of Therapeutics*, Gilman et al., eds., Pergamon Press, New York, pp. 3-32.

Cvitkovitch, Dennis, et al. 'Presentation (poster) American Society of Microbiology Jul. 6-9, 2001 'A cell-cell signaling system in *Streptococcus mutans* modulates several virulence factors including acid tolerance and the ability to form biofilms.' Cell-cell communications in bacteria', Snowbird, Utah.

Li, Yung Hua, et al. Presentation (poster) American Society of Microbiology May 20-24, 2001 'A quorum sensing system essential for induction of genetic competence in *Streptococcus mutans* is involved in biofilm formation.' Orlando, Florida.

Li, Yung Hua, Presentation (oral) Jan. 31, 2001 'Quorum sensing in *Streptococcus mutans* biofilms.' Edmonton, Alberta.

Article (on-line) Jan. 16, 2001 'Natural genetic transformation of *Streptococcus mutans* growing in biofilms.' *Journal of Bacteriology* 183(3), p. 897-908.

Li, Yung Hua et al. Article (hard copy) Feb. 2001 'Natural genetic transformation of *Streptococcus mutans* growing in biofilms' *Journal of Bacteriology*, 183 p. 897-908.

Cvitkovitch, Dennis. Presentation (oral) Dec. 12, 2000 'Survival and dominance in *Streptococcus mutans* biofilms.' Toronto, Ontario.

Cvitkovitch, Dennis. Presentation (oral) Oct. 16, 2000 'Genetic Transformation in *Streptococcus mutans* biofilms.' Rochester, New York.

Cvitkovitch, Dennis. Presentation (oral) Oct. 25, 2000 'Cell-cell signaling in *Streptococcus mutans* biofilms.' Edmonton, Alberta.

Cvitkovitch, Dennis and Li, Yung Hua. Presentation (poster) American Society of Microbiology Jul. 16-20, 2000 'Natural genetic transformation of *Streptococcus mutans* growing in biofilms.' Big Sky, Montana.

Li, Yung Hua, et al.. Presentation (poster) American Society of Microbiology Jul. 16-20, 2000 'Acid tolerance response of biofilm-grown cells of *Streptococcus mutans*.' Big Sky, Montana.

GenBank submission Jun. 12, 2000 *Streptococcus mutans* competence stimulating peptide precursor (comC) gene.

GenBank Jan. 15, 2001 *Streptococcus mutans* strain BM71 competence stimulating protein Accession AF277151.

Li, Yung Hua and Cvitkovitch, Dennis. Abstract Jun. 2000 'Natural genetic transformation of *Streptococcus mutans* growing in biofilms.' Winnipeg, Manitoba.

Barrett et al., "Antibacterial agents that inhibit two-component signal transduction systems", *Proc. Natl. Acad. Sci. USA*, 95:5317-5322 (1998).

Brady et al., "Monoclonal Antibody-Mediated Modulation of the Humoral Immune Response against Mucosally Applied *Streptococcus mutans*", *Infection and Immunity*, 68(4):1796-1805 (2000).

Burne, "Oral streptococci . . . Products of Their Environment", *J. Dent. Res.*, 77(3):445-452 (1998).

Devulapalle et al., "Effect of carbohydrate fatty acid esters on *Streptococcus sobrinus* nad glucosyltransferase activity", *Carbohydrate Research*, 339:1029-1034 (2004).

Jespersgaard et al., "Protective Immunity against *Streptococcus mutans* Infection in Mice after Intranasal Immunization with the Glucan-Binding Region of *S. mutans* Glucosyltransferase", *Infection and Immunity*, 67(12):6543-6549 (1999).

Kawasaki, "Amplification of RNA", *PCR Protocols: A Guide to Methods and Applications*, San Diego: Academic Press, Inc., pp. 21-27 (1990).

Kawashima et al., "Real-time interaction of oral streptococci with human salivary components", *Oral Microbiology Immunology*, 18:220-225 (2003).

Li et al., "Characteristics of accumulation of oral gram-positive bacteria on mucin-conditioned glass surfaces in a model system", *Oral Microbiol. Immunol.*, 9:1-11 (1994).

Lindler et al., "Characterization of Genetic Transformation in *Streptococcus mutans* by Using a Novel High-Efficiency Plasmid Marker Rescue System", *J Bacteriol.*, 166(2):658-665 (1986).

Morgan et al., "Approaches to the discovery of non-peptide ligands for peptide receptors and peptidases", *Annual Reports in Medicinal Chemistry*, vol. 24, Ch. 26, pp. 243-252 (1989).

Perry et al., "Genetic Transformation of Putative Cariogenic Properties in *Streptococcus mutans*", *Infect. Immun.*, 41(2):722-7.(1983).

Rakel, *Conn's Current Therapy*, Philadelphia: W. B. Saunders Company, Table of Contents (1995).

Suntharalingam et al., "Quorum sensing in streptococcal biofilm formation", *Trends in Microbiology*, 13(1):3-6 (2005).

Svensater et al., "Acid tolerance response and survival by oral bacteria", *Oral Microbiol. Immunol.*, 12:266-273 (1997).

Thompson et al., "Clustal W: improving the sensitivity of progressive multiple sequence alignment through sequence weighting, position-specific gap penalties and weight matrix choice", *Nucleic Acids Research*, 22(22):4673-4680 (1994).

\* cited by examiner

Figure 1

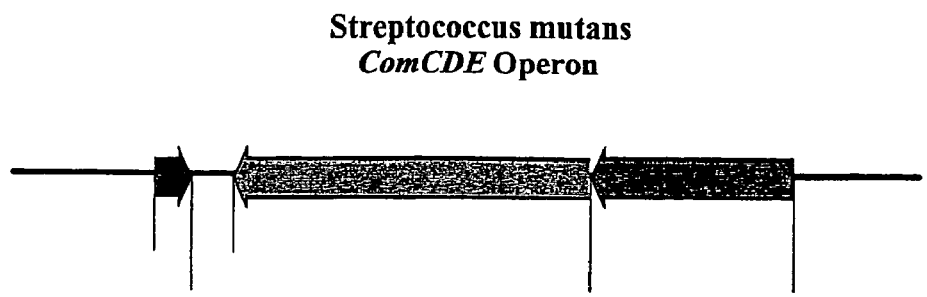

Figure 3

A.
MKKTLSLKNDFKEIKTDELEIIIGGSGSLSTFFRLFNRSFTQALGK

B.
MNEALMILSNGLLTYLTVLFLLFLFSKVSNVTLSKKELTLFSISNFLIMIAVTMVNVNL
FYPAEPLYFIALSIYLNRQNSLSLNIFYGLLPVASSDLFRRAIIFFILDGTQGIVMGSS
IITTYMIEFAGIALSYLFLSVFNVDIGRLKDSLTKMKVKKRLIPMNITMLLYYLLIQVL
YVIESYNVIPTLKFRKFVVIVYLILFLILISFLSQYTKQKVQNEIMAQKEAQIRNITQY
SQQIESLYKDIRSFRHDYLNILTSLRLGIENKDLASIEKIYHQILEKTGHQLQDTRYNI
GHLANIQNDAVKGILSAKILEAQNKKIAVNVEVSSKIQLPEMELLDFITILSILCDNAI
EAAFESLNPEIQLAFFKKNGSIVFIIQNSTKEKQIDVSKIFKENYSTKGSNRGIGLAKV
NHILEHYPKTSLQTSNHHHLFKQLLIIK

C.
MISIFVLEDDFLQQGRLETTIAAIMKEKNWSYKELTIFGKPQQLIDAIPEKGNHQIFFL
DIEIKKEEKKGLEVANQIRQHNPSAVIVFVTTHSEFMPLTFQYQVSALDFIDKSLNPEE
FSHRIESALYYAMENSQKNGQSEELFIFHSSETQFQVPFAEILYFETSSTAHKLCLYTY
DERIEFYGSMTDIVKMDKRLFQCHRSFIVNPANITRIDRKKRLAYFRNNKSCLISRTKL
TKLRAVIADQRRAK

Fig. 2A

[ATGAAAAAAACACTATCATTAAAAAATGACTTTAAAGAAATTAAGACTGATGAATTAGA
GATTATCATTGGCGGA ( AGCGGAAGCCTATCAACATTTTTCCGGCTGTTTAACAGAAGTT
TTACACAAGCTTTGGGAAAA) ] TAA [SEQ ID NO: 4]

Fig. 2B

AGCGGAAGCCTATCAACATTTTTCCGGCTGTTTAACAGAAGTTTTACACAAGCTTTGGGA
AAA [SEQ ID NO: 5]

Fig. 2C

[ATGAATGAAGCCTTAATGATACTTTCAAATGGTTTATTAACTTATCTAACCGT
TCTATTTCTCTTGTTTCTATTTTCTAAGGTAAGTAATGTCACTTTATCGAAAAA
GGAATTAACTCTTTTTTCGATAAGCAATTTTCTGATAATGATTGCTGTTACGA
TGGTGAACGTAAACCTGTTTTATCCTGCAGAGCCTCTTTATTTTATAGCTTTAT
CAATTTATCTTAATAGACAGAATAGTCTTTCTCTAAATATATTTTATGGTCTGC
TGCCTGTTGCCAGTTCTGACTTGTTTAGGCGGGCAATCATATTCTTTATCTTGG
ATGGAACTCAAGGAATTGTAATGGGCAGTAGCATTATAACCACCTATATGAT
CGAGTTTGCAGGAATAGCGCTAAGTTACCTCTTTCTCAGTGTGTTCAATGTTG
ATATTGGTCGACTTAAAGATAGTTTGACCAAGATGAAGGTCAAAAAACGCTT
GATTCCAATGAATATTACTATGCTTCTATACTACCTTTTAATACAGGTATTGT
ATGTTATAGAGAGTTATAATGTGATACCGACTTTAAAATTTCGTAAATTTGTC
GTTATTGTCTATCTTATTTTATTTTTGATTCTGATCTCATTTTTAAGCCAATATA
CCAAACAAAAGGTTCAAAATGAGATAATGGCACAAAAGGAAGCTCAGATTC
GAAATATCACCCAGTATAGTCAGCAAATAGAATCTCTTTACAAGGATATTCG
AAGTTTCCGCCATGATTATCTGAATATTTTAACTAGCCTCAGATTAGGCATTG
AAAATAAAGATTTAGCTAGTATTGAAAAGATTTACCATCAAATCTTAGAAAA
AACAGGACATCAATTGCAGGATACCCGTTATAATATCGGCCATCTAGCTAAT
ATTCAAAACGATGCTGTCAAGGGTATCTTGTCAGCAAAAATCTTAGAAGCTC
AGAATAAAAAGATTGCTGTCAATGTAGAAGTCTCAAGTAAAATACAACTGCC
TGAGATGGAGTTGCTTGATTTCATTACCATACTTTCTATCTTGTGTGATAATGC
CATTGAGGCTGCTTTCGAATCATTAAATCCTGAAATTCAGTTAGCCTTTTTTA
AGAAAAATGGCAGTATAGTCTTTATCATTCAGAATTCCACCAAAGAAAAACA
AATAGATGTGAGTAAAATTTTTAAAGAAAACTATTCCACTAAAGGCTCCAAT
CGCGGTATTGGTTTAGCAAAGGTGAATCATATTCTTGAACATTATCCCAAAAC
CAGTTTACAAACAAGCAATCATCATCATTTATTCAAGCAACTCCTAATAATAA
AA] TAG [SEQ ID NO: 6]

Fig. 2D

[ATGATTTCTATTTTTGTATTGGAAGATGATTTTTTACAACAAGGACGTCTTGAAACCAC
CATTGCAGCTATCATGAAAGAAAAAAATTGGTCTTATAAAGAATTGACTATTTTTGGAAA
ACCACAACAACTTATTGACGCTATCCCTGAAAAGGGCAATCACCAGATTTTCTTTTTGGA
TATTGAAATCAAAAAAGAGGAAAAGAAAGGACTGGAAGTAGCCAATCAGATTAGACAGCA
TAATCCTAGTGCAGTTATTGTCTTTGTCACGACACATTCTGAGTTTATGCCCCTCACTTT
TCAGTATCAGGTATCTGCTTTGGATTTTATTGATAAATCTTTGAATCCTGAGGAGTTCTC
CCACCGCATTGAATCAGCGCTGTATTATGCTATGGAAAACAGCCAGAAGAATGGTCAATC
AGAGGAACTTTTTATTTTCCATTCATCTGAAACTCAGTTTCAGGTCCCTTTTGCTGAGAT
TCTGTATTTTGAAACATCTTCAACAGCCCATAAGCTCTGCCTTTATACTTATGATGAACG
GATTGAATTCTACGGCAGTATGACTGACATTGTTAAAATGGATAAGAGACTTTTTCAGTG
CCATCGCTCTTTTATTGTCAATCCTGCCAATATTACCCGTATTGATCGGAAAAAACGCTT
GGCCTATTTTCGAAATAATAAGTCTTGTCTTATTTCACGAACTAAGTTAACAAAACTGAG
AGCTGTGATTGCTGATCAAAGGAGAGCAAAA] TGA [SEQ ID NO: 7]

Fig. 3A

MKKTLSLKNDFKEIKTDELEIIIGGSGSLSTFFRLFNRSFTQALGK [SEQ ID NO: 1]

Fig. 3B

MNEALMILSNGLLTYLTVLFLLFLFSKVSNVTLSKKELTLFSISNFLIMIAVTMVNVNL
FYPAEPLYFIALSIYLNRQNSLSLNIFYGLLPVASSDLFRRAIIFFILDGTQGIVMGSS
IITTYMIEFAGIALSYLFLSVFNVDIGRLKDSLTKMKVKKRLIPMNITMLLYYLLIQVL
YVIESYNVIPTLKFRKFVVIVYLILFLILISFLSQYTKQKVQNEIMAQKEAQIRNITQY
SQQIESLYKDIRSFRHDYLNILTSLRLGIENKDLASIEKIYHQILEKTGHQLQDTRYNI
GHLANIQNDAVKGILSAKILEAQNKKIAVNVEVSSKIQLPEMELLDFITILSILCDNAI
EAAFESLNPEIQLAFFKKNGSIVFIIQNSTKEKQIDVSKIFKENYSTKGSNRGIGLAKV
NHILEHYPKTSLQTSNHHHLFKQLLIIK [SEQ ID NO: 2]

Fig. 3C

MISIFVLEDDFLQQGRLETTIAAIMKEKNWSYKELTIFGKPQQLIDAIPEKGNHQIFFL
DIEIKKEEKKGLEVANQIRQHNPSAVIVFVTTHSEFMPLTFQYQVSALDFIDKSLNPEE
FSHRIESALYYAMENSQKNGQSEELFIFHSSETQFQVPFAEILYFETSSTAHKLCLYTY
DERIEFYGSMTDIVKMDKRLFQCHRSFIVNPANITRIDRKKRLAYFRNNKSCLISRTKL
TKLRAVIADQRRAK [SEQ ID NO: 3]

Fig. 4A

| | | |
|---|---|---|
| BM71 CSP | 1 MKKTPSLKNDFKEIKTDELEIIIGGSGSLSTFFRLFNRSFTQALGK | 46 [SEQ ID NO: 8] |
| GB14 CSP | 1 MKKTLSLKNDFKEIKTDELEIIIGGSGSLSTFFRLFNRSFTQALGK | 46 [SEQ ID NO: 9] |
| H7 CSP | 1 MKKTLSLKNDFKEIKTDELEIIIGGSGSLSTFFRLFNRSFTQALGK | 46 [SEQ ID NO: 9] |
| JHIOO5 CSP | 1 MKKTLSLKNDFKEIKTDELEIIIGGSGTLSTFFRLFNRSFTQA | 43 [SEQ ID NO: 10] |
| LT11 CSP | 1 MKKTLSLKNDFKEIKTDELEIIIGGSGSLSTFFRLFNRSFTQALGK | 46 [SEQ ID NO: 9] |
| NG8 CSP | 1 MKKTLSLKNDFKEIKTDELEIIIGGSGSLSTFFRLFNRSFTQALGK | 46 [SEQ ID NO: 9] |
| UABIS9 CSP | 1 MKKTLSLKNDFKEIKTDELEIIIGGSGSLSTFFRLFNRSFTQALGK | 46 [SEQ ID NO: 9] |
| | **** ******************* ************* | |

Fig. 4B consensus: 1 MKKTLSLKNDFKEIKTDELEIIIGG SGSLSTFFRLFNRSFTQALGK 46 [SEQ ID NO:9]
predicted cleavage site:

Fig. 5

SGSLSTFFRLFNRSFTQALGK [SEQ ID NO: 11]

| Strain | Peptide added Number of Transformants/Recipients | No peptide Number of Transformants/Recipients |
|---|---|---|
| UAB15 | $4.65 \times 10^{-1}$ | $1.78 \times 10^{-6}$ |
| JH1005[2] | $6.98 \times 10^{-2}$ | 0 |

[1]The final concentration of SCSP used was 500 ng/ml.
The strain contains a nonsense mutation in the *comC* gene encoding the CSP.

Fig. 8

ComC region

ComC Primer Pair: F5-B5
--------------------------

[F5] 23406-23424   5'- AGTTTTTTTGTCTGGCTGCG -3' [SEQ ID NO: 12]
                  19 nt forward primer
                  pct G+C: 47.4 Tm: 50.5

[B5] 24056-24037 5'-TCCACTAAAGGCTCCAATCG -3' [SEQ ID NO: 13]
                  20 nt backward primer
                  pct G+C: 50.0 Tm: 51.9

651 Dtproducl for F5-B5 pair (23406-24056)
                  Optimal annealing temp: 50.3
                  pct G+C: 30.9 Tm: 71.5

ComD region

ComD Primer Pair: FI-B I
--------------------------

[FI] 392-415      5'-CGCTAAGTTACCTCTTTCTCAGTG -3' [SEQ ID NO: 14]
                  24 nt forward primer
                  pct G+C: 45.8 Tm: 51.6

[Bl]   683-663 5'-GCTTCCTTTTGTGCCATTATC -3' [SEQ ID NO: 15]
                  21 nt backward primer
                  pct G+C: 42.9 Tm: 50.8

292 nt product for FI-BI pair (392-683)
                  Optimal annealing temp: 49.5
                  pct G+C: 30.8 Tm: 70.2

ComE region

ComE Primer Pair: FI-BI
------------------------

[Fl] 145-165      5'-CTGAAAAGGGCAATCACCAG -3' [SEQ ID NO: 16]
                  21 nt forward primer
                  pct G+C: 52.4 Tm: 55.9

[Bl] 606-585      5'-GCGATGGCACTGAAAAAGTCTC-3' [SEQ ID NO: 17]
                  22 nt backward primer
                  pct G+C: 50.0 Tm: 55.4

462 nt product for FI-B I pair (145-606)
                  Optimal annealing temp: 53.6
                  pct G+C: 38.3 Tm: 74.1

Fig. 9A

Sequence Range: 1 to 2557

```
           10         20         30         40         50
ACATTATGTGTCCTAAGGAAAATATTACTTTTTCAAGAAAATCCATGATT  [SEQ ID NO: 18]
TGTAATACACAGGATTCCTTTTATAATGAAAAAGTTCTTTTAGGTACTAA  [SEQ ID NO: 19]
                      <K   K   L   F   I   W   S   K
<_____

60         70         80         90        100
TTTTCATAAAAAATAGTATACTAATTATAATCAAAAAAAGGAGATATAAA
AAAAGTATTTTTTATCATATGATTAATATTAGTTTTTTTCCTCTATATTT
<K   M   F   F   L   I   S   I   I   I   L   F   L   L   Y   L
<_____

110        120        130        140        150
ATGAAAAAAACACTATCATTAAAAAATGACTTTAAAGAAATTAAGACTGA
TACTTTTTTTGTGATAGTAATTTTTTACTGAAATTTCTTTAATTCTGACT
[SEQ ID NO: 1 ] M   K   K   T   L   S   L   K   N   D   F   K   E   I   K   T   D>
_____ORF RF [2]_____>
<I   F   F   V   S   D   N   F   F   S   K   L   S   I   L   V   S
<_____

160        170        180        190        200
TGAATTAGAGATTATCATTGGCGGAAGCGGAAGCCTATCAACATTTTTCC
ACTTAATCTCTAATAGTAACCGCCTTCGCCTTCGGATAGTTGTAAAAAGG
    E   L   E   I   I   I   G   G   S   G   S   L   S   T   F   F>
_____ORF RF [2]_____>
<S   N   S   I   I   M [SEQ ID NO: 20]
<_____

210        220        230        240        250
GGCTGTTTAACAGAAGTTTTACACAAGCTTTGGGAAAATAAGATAGGCTA
CCGACAAATTGTCTTCAAAATGTGTTCGAAACCCTTTTATTCTATCCGAT
    R   L   F   N   R   S   F   T   Q   A   L   G   K>
_____ORF RF [2]_____>

260        270        280        290        300
ACATTGGAATAAAACAAGGCTGGATTTATTATTCCAGCCTTTTTAAATGT
TGTAACCTTATTTTGTTCCGACCTAAATAATAAGGTCGGAAAAATTTACA 310        320        330        340        350
AAAATAAAAATACAGGGTTAAATAATCAAGTGTGCTGTCGTGGATGAGAA
TTTTATTTTTATGTCCCAATTTATTAGTTCACACGACAGCACCTACTCTT 360        370        380        390        400
GATAAAACTATCTCTTAGAGAATAGGCCTCCTCTATTTTATTATTAGGAG
CTATTTTGATAGAGAATCTCTTATCCGGAGGAGATAAAATAATAATCCTC
                                    <K   I   I   L   L
                                    <____ORF RF [_____

410        420        430        440        450
TTGCTTGAATAAATGATGATGATTGCTTGTTTGTAAACTGGTTTTGGGAT
AACGAACTTATTTACTACTACTAACGAACAAACATTTGACCAAAACCCTA
<Q   K   F   L   H   H   H   N   S   T   Q   L   S   T   K   P   Y
<_____ORF RF[4] C_____
```

Fig. 9B

```
          460        470        480        490        500
AATGTTCAAGAATATGATTCACCTTTGCTAAACCAATACCGCGATTGGAG
TTACAAGTTCTTATACTAAGTGGAAACGATTTGGTTATGGCGCTAACCTC
 <H   E   L   I   H   N   V   K   A   L   G   I   G   R   N   S
 <_____ORF RF [4] C_____

510        520        530        540        550
CCTTTAGTGGAATAGTTTTCTTTAAAAATTTTACTCACATCTATTTGTTT
GGAAATCACCTTATCAAAAGAAATTTTTAAAATGAGTGTAGATAAACAAA
 <G   K   T   S   Y   N   E   K   F   I   K   S   V   D   I   Q   K
 <_____ORF  RF[ 4] C_____

560        570        580        590        600
TTCTTTGGTGGAATTCTGAATGATAAAGACTATACTGCCATTTTTCTTAA
AAGAAACCACCTTAAGACTTACTATTTCTGATATGACGGTAAAAAGAATT
 <F   K   T   S   N   Q   I   I   F   V   I   S   G   N   K   K   F
 <_____ORF RF [4] C_____

610        620        630        640        650
AAAAGGCTAACTGAATTTCAGGATTTAATGATTCGAAAGCAGCCTCAATG
TTTTCCGATTGACTTAAAGTCCTAAATTACTAAGCTTTCGTCGGAGTTAC
                                            M> [SEQ ID NO: 21]
                                        ____>
 <F   A   L   Q   I   E   P   N   L   S   E   F   A   A   E   I
 <_____ORF RF [4] C_____

660        670        680        690        700
GCATTATCACACAAGATAGAAAGTATGGTAATGAAATCAAGCAACTCCAT
CGTAATAGTGTGTTCTATCTTTCATACCATTACTTTAGTTCGTTGAGGTA
    A   L   S   H   K   I   E   S   M   V   M   K   S   S   N   S   I>
 _____ORF RF [3]_____>
 <A   N   D   C   L   I   S   L   I   T   I   F   D   L   L   E   M 710        720        730        740        750
CTCAGGCAGTTGTATTTTACTTGAGACTTCTACATTGACAGCAATCTTTT
GAGTCCGTCAACATAAAATGAACTCTGAAGATGTAACTGTCGTTAGAAAA
    S   G   S   C   I   L   L   E   T   S   T   L   T   A   I   F>
 _____ORF RF [3]_____>
 <E   P   L   Q   I   K   S   S   V   E   V   N   V   A   I   K   K
 <_____ORF RF [4] C_____

760        770        780        790        800
TATTCTGAGCTTCTAAGATTTTTGCTGACAAGATACCCTTGACAGCATCG
ATAAGACTCGAAGATTCTAAAAACGACTGTTCTATGGGAACTGTCGTAGC
   L   F>
 _____>
 <N   Q   A   E   L   I   K   A   S   L   I   G   K   V   A   D
 <_____ORF RF [4] C_____

810        820        830        840        850
TTTTGAATATTAGCTAGATGGCCGATATTATAACGGGTATCCTGCAATTG
AAAACTTATAATCGATCTACCGGCTATAATATTGCCCATAGGACGTTAAC
 <N   Q   I   N   A   L   H   G   I   N   Y   R   T   D   Q   L   Q
 <_____ORF RF [4] C_____
```

Fig. 9C

```
            860         870         880         890         900
    ATGTCCTGTTTTTTCTAAGATTTGATGGTAAATCTTTTCAATACTAGCTA
    TACAGGACAAAAAAGATTCTAAACTACCATTTAGAAAAGTTATGATCGAT
    <H   G   T   K   E   L   I   Q   H   Y   I   K   E   I   S   A   L
    <_____ORF RF [4] C_____

910         920         930         940         950
    AATCTTTATTTTCAATGCCTAATCTGAGGCTAGTTAAAATATTCAGATAA
    TTAGAAATAAAAGTTACGGATTAGACTCCGATCAATTTTATAAGTCTATT
     <D   K   N   E   I   G   L   R   L   S   T   L   I   N   L   Y
    <_____ORF RF [4] C_____

960         970         980         990         1000
    TCATGGCGGAAACTTCGAATATCCTTGTAAAGAGATTCTATTTGCTGACT
    AGTACCGCCTTTGAAGCTTATAGGAACATTTCTCTAAGATAAACGACTGA
         M   A   E   T   S   N   I   L   V   K   R   F   Y   L   L   T> [SEQ ID NO:22]
                                                                      >
    <D   H   R   F   S   R   I   D   K   Y   L   S   E   I   Q   Q   S
    <_____ORF RF [4] C_____

1010        1020        1030        1040        1050
    ATACTGGGTGATATTTCGAATCTGAGCTTCCTTTTGTGCCATTATCTCAT
    TATGACCCACTATAAAGCTTAGACTCGAAGGAAAACACGGTAATAGAGTA
         I   L   G   D   I   S   N   L   S   F   L   L   C   H   Y   L   I>
                                                                          >
    <Y   Q   T   I   N   R   I   Q   A   E   K   Q   A   M   I   E   N
    <_____ORF RF [4] C_____

1060        1070        1080        1090        1100
    TTTGAACCTTTTGTTTGGTATATTGGCTTAAAAATGAGATCAGAATCAAA
    AAACTTGGAAAACAAACCATATAACCGAATTTTTACTCTAGTCTTAGTTT
         L   N   L   L   F   G   I   L   A>
                                          >
         <Q   V   K   Q   K   T   Y   Q   S   L   F   S   I   L   I   L
    <_____ORF RF [4] C_____

1110        1120        1130        1140        1150
    AATAAAATAAGATAGACAATAACGACAAATTTACGAAATTTTAAAGTCGG
    TTATTTTATTCTATCTGTTATTGCTGTTTAAATGCTTTAAAATTTCAGCC
    <F   L   I   L   Y   V   I   V   V   F   K   R   F   K   L   T   P
    <_____ORF RF [4] C_____

1160        1170        1180        1190        1200
    TATCACATTATAACTCTCTATAACATACAATACCTGTATTAAAAGGTAGT
    ATAGTGTAATATTGAGAGATATTGTATGTTATGGACATAATTTTCCATCA
    <I   V   N   Y   S   E   I   V   Y   L   V   Q   I   L   L   Y   Y
    <_____ORF RF [4] C_____

1210        1220        1230        1240        1250
    ATAGAAGCATAGTAATATTCATTGGAATCAAGCGTTTTTTGACCTTCATC
    TATCTTCGTATCATTATAAGTAACCTTAGTTCGCAAAAAACTGGAAGTAG
     <L   L   M   T   I   N   M   P   I   L   R   K   K   V   K   M
    <_____ORF RF [4] C_____
```

Fig. 9D

```
             1260       1270       1280       1290       1300
       TTGGTCAAACTATCTTTAAGTCGACCAATATCAACATTGAACACACTGAG
       AACCAGTTTGATAGAAATTCAGCTGGTTATAGTTGTAACTTGTGTGACTC
       <K   T   L   S   D   K   L   R   G   I   D   V   N   F   V   S   L
       <_____ORF RF [4] C_____

1310       1320       1330       1340       1350
       AAAGAGGTAACTTAGCGCTATTCCTGCAAACTCGATCATATAGGTGGTTA
       TTTCTCCATTGAATCGCGATAAGGACGTTTGAGCTAGTATATCCACCAAT
       <F   L   Y   S   L   A   I   G   A   F   E   I   M   Y   T   T   I
       <_____ORF RF [4] C_____

1360       1370       1380       1390       1400
       TAATGCTACTGCCCATTACAATTCCTTGAGTTCCATCCAAGATAAAGAAT
       ATTACGATGACGGGTAATGTTAAGGAACTCAAGGTAGGTTCTATTTCTTA
        <I   S   S   G   M   V   I   G   Q   T   G   D   L   I   F   F
       <_____ORF RF [4] C_____
                       <L   E   K   L   E   M   W   S   L   S   Y
                       <_____

1410       1420       1430       1440       1450
       ATGATTGCCCGCCTAAACAAGTCAGAACTGGCAACAGGCAGCAGACCATA
       TACTAACGGGCGGATTTGTTCAGTCTTGACCGTTGTCCGTCGTCTGGTAT
       <I   I   A   R   R   F   L   D   S   S   A   V   P   L   L   G   Y
       <_____ORF RF [4] C_____
         <S   Q   G   G   L   C   T   L   V   P   L   L   C   C   V   M [SEQ ID NO: 23]
       <_____

1460       1470       1480       1490       1500
       AAATATATTTAGAGAAAGACTATTCTGTCTATTAAGATAAATTGATAAAG
       TTTATATAAATCTCTTTCTGATAAGACAGATAATTCTATTTAACTATTTC
       <F   I   N   L   S   L   S   N   Q   R   N   L   Y   I   S   L   A
       <_____ORF RF [4] C_____

1510       1520       1530       1540       1550
       CTATAAAATAAAGAGGCTCTGCAGGATAAAACAGGTTTACGTTCACCATC
       GATATTTTATTTCTCCGAGACGTCCTATTTTGTCCAAATGCAAGTGGTAG
        <I   F   Y   L   P   E   A   P   Y   F   L   N   V   N   V   M
       <_____ORF RF [4] C_____

1560       1570       1580       1590       1600
       GTAACAGCAATCATTATCAGAAAATTGCTTATCGAAAAAGAGTTAATTC
       CATTGTCGTTAGTAATAGTCTTTTAACGAATAGCTTTTTCTCAATTAAG
       <T   V   A   I   M   I   L   F   N   S   I   S   F   L   T   L   E
       <_____ORF RF [4] C_____

1610       1620       1630       1640       1650
       CTTTTTCGATAAAGTGACATTACTTACCTTAGAAAATAGAAACAAGAGAA
       GAAAAAGCTATTTCACTGTAATGAATGGAATCTTTTATCTTTGTTCTCTT
       <K   K   S   L   T   V   N   S   V   K   S   F   L   F   L   L   F
       <_____ORF RF [4] C_____
```

Fig. 9E

```
           1660        1670        1680        1690        1700
     ATAGAACGGTTAGATAAGTTAATAAACCATTTGAAAGTATCATTAAGGCT
     TATCTTGCCAATCTATTCAATTATTTGGTAAACTTTCATAGTAATTCCGA
      <L   V   T   L   Y   T   L   L   G   N   S   L   I   M   L   A
     <_____ORF RF [4] C_____

1710        1720        1730        1740        1750
     TCATTCATTTTGCTCTCCTTTGATCAGCAATCACAGCTCTCAGTTTTGTT
     AGTAAGTAAAACGAGAGGAAACTAGTCGTTAGTGTCGAGAGTCAAAACAA
     <E   N   M [SEQ ID NO: 2]
     <_____
              <K   A   R   R   Q   D   A   I   V   A   R   L   K   T
              <_____ORF RF [5] C_____

1760        1770        1780        1790        1800
     AACTTAGTTCGTGAAATAAGACAAGACTTATTATTTCGAAAATAGGCCAA
     TTGAATCAAGCACTTTATTCTGTTCTGAATAATAAAGCTTTTATCCGGTT
     <L   K   T   R   S   I   L   C   S   K   N   N   R   F   Y   A   L
     <_____ORF RF [5] C_____

1810        1820        1830        1840        1850
     GCGTTTTTTCCGATCAATACGGGTAATATTGGCAGGATTGACAATAAAAG
     CGCAAAAAAGGCTAGTTATGCCCATTATAACCGTCCTAACTGTTATTTTC
     <R   K   K   R   D   I   R   T   I   N   A   P   N   V   I   F   S
     <_____ORF RF [5] C_____

1860        1870        1880        1890        1900
     AGCGATGGCACTGAAAAAGTCTCTTATCCATTTTAACAATGTCAGTCATA
     TCGCTACCGTGACTTTTTCAGAGAATAGGTAAAATTGTTACAGTCAGTAT
     [SEQ ID NO: 24]MALK   K   S   L   I   H   F   N   N   V   S   H>
     _____ORF RF [1]_____>
           <R   H   C   Q   F   L   R   K   D   M   K   V   I   D   T   M
     <_____ORF RF [5] C_____
                                                                    <V
                                                                    <___

1910        1920        1930        1940        1950
     CTGCCGTAGAATTCAATCCGTTCATCATAAGTATAAAGGCAGAGCTTATG
     GACGGCATCTTAAGTTAGGCAAGTAGTATTCATATTTCCGTCTCGAATAC
      T   A   V   E   F   N   P   F   I   I   S   I   K   A   E   L   M>
     _____ORF RF [1]_____>
     <S   G   Y   F   E   I   R   E   D   Y   T   Y   L   C   L   K   H
     <_____ORF RF [5] C_____
         <A   T   S   N   L   G   N   M   M   L   I   F   A   S   S   I
     <_____ORF RF [6] C_____

1960        1970        1980        1990        2000
     GGCTGTTGAAGATGTTTCAAAATACAGAATCTCAGCAAAAGGGACCTGAA
     CCGACAACTTCTACAAAGTTTTATGTCTTAGAGTCGTTTTCCCTGGACTT
       G   C>
     _____>
     <A   T   S   S   T   E   F   Y   L   I   E   A   F   P   V   Q   F
     <_____ORF RF [5] C_____
     <P   Q   Q   L   H   K   L   I   C   F   R   L   L   L   S   R   F
     <_____ORF RF [6] C_____
```

Fig. 9F

```
         2010       2020       2030       2040       2050
ACTGAGTTTCAGATGAATGGAAAATAAAAAGTTCCTCTGATTGACCATTC
TGACTCAAAGTCTACTTACCTTTTATTTTTCAAGGAGACTAACTGGTAAG
  <Q  T  E  S  S  H  F  I  F  L  E  E  S  Q  G  N
 <_____ORF RF [5] C_____
  <S  L  K  L  H  I  S  F  L  F  N  R  Q  N  V  M  R
 <_____ORF RF [6] C_____

2060       2070       2080       2090       2100
TTCTGGCTGTTTTCCATAGCATAATACAGCGCTGATTCAATGCGGTGGGA
AAGACCGACAAAAGGTATCGTATTATGTCGCGACTAAGTTACGCCACCCT
 <K  Q  S  N  E  M  A  Y  Y  L  A  S  E  I  R  H  S
 <_____ORF RF [5] C_____
     <R  A  T  K  W  L  M [SEQ ID NO: 25]
 <_____ORF RF [6] C_____

2110       2120       2130       2140       2150
GAACTCCTCAGGATTCAAAGATTTATCAATAAAATCCAAAGCAGATACCT
CTTGAGGAGTCCTAAGTTTCTAAATAGTTATTTTAGGTTTCGTCTATGGA
 <F  E  E  P  N  L  S  K  D  I  F  D  L  A  S  V  Q
 <_____ORF RF [5] C_____

2160       2170       2180       2190       2200
GATACTGAAAAGTGAGGGGCATAAACTCAGAATGTGTCGTGACAAAGACA
CTATGACTTTTCACTCCCCGTATTTGAGTCTTACACAGCACTGTTTCTGT
                               M  C  R  D  K  D> [SEQ ID NO: 26]
                              _____>
 <Y  Q  F  T  L  P  M  F  E  S  H  T  T  V  F  V
 <_____ORF RF [5] C_____

2210       2220       2230       2240       2250
ATAACTGCACTAGGATTATGCTGTCTAATCTGATTGGCTACTTCCAGTCC
TATTGACGTGATCCTAATACGACAGATTAGACTAACCGATGAAGGTCAGG
 N  N  C  T  R  I  M  L  S  N  L  I  G  Y  F  Q  S>
_____>
 <I  V  A  S  P  N  H  Q  R  I  Q  N  A  V  E  L  G
 <_____ORF RF [5] C_____

2260       2270       2280       2290       2300
TTTCTTTTCCTCTTTTTTGATTTCAATATCCAAAAAGAAAATCTGGTGAT
AAAGAAAAGGAGAAAAAACTAAAGTTATAGGTTTTTCTTTTAGACCACTA
   F   L  F  L  F  F  D  F  N  I  Q  K  E  N  L  V  I>
                                                      >
 <K  K  E  E  K  K  I  E  I  D  L  F  F  I  Q  H  N
 <_____ORF RF [5] C_____

2310       2320       2330       2340       2350
TGCCCTTTTCAGGGATAGCGTCAATAAGTTGTTGTGGTTTTCCAAAAATA
ACGGGAAAAGTCCCTATCGCAGTTATTCAACAACACCAAAAGGTTTTTAT
    A  L  F  R  D  S  V  N  K  L  L  W  F  S  K  N>
                                                    >
 <G  K  E  P  I  A  D  I  L  Q  Q  P  K  G  F  I
 <_____ORF RF [5] C_____
```

Fig. 9G

```
          2360        2370        2390        2390        2400
GTCAATTCTTTATAAGACCAATTTTTTTCTTTCATGATAGCTGCAATGGT
CAGTTAAGAAATATTCTGGTTAAAAAAAGAAAGTACTATCGACGTTACCA
 S   Q   F   F   I   R   P   I   F   F   F   H   D   S   C   N   G>
                                                                  >
                                           M   I   A   A   M   V> [SEQ ID NO:27]
                                                                >
<T   L   E   K   Y   S   W   N   K   E   K   M   I   A   A   I   T
<_____ORF RF [5] C_____

2410        2420        2430        2440        2450
GGTTTCAAGACGTCCTTGTTGTAAAAAATCATCTTCCAATACAAAAATAG
CCAAAGTTCTGCAGGAACAACATTTTTTAGTAGAAGGTTATGTTTTATC
    G   F   K   T   S   L   L>
                              >
     V   S   R   R   P   C   K   K   S   S   S   N   T   K   I>
                                                                >
<T   E   L   R   G   Q   Q   L   F   D   D   E   L   V   F   I   S
<_____ORF RF [5] C_____

2460        2470        2480        2490        2500
AAATCATTATTTCTCCTTTAATCTTCTATTTAGGTTAGCTGATTAACACT
TTTAGTAATAAAGAGGAAATTAGAAGATAAATCCAATCGACTAATTGTGA
 E   I   I   I   S   P   L   I   F   Y   L   G>
                                              >
              <I   M [SEQ ID NO: 3]
              <_____

2510        2520        2530        2540        2550
ATACACAGAAAAGGTATAAAACGATATCACTCAATAAAATCTACTAACTT
TATGTGTCTTTTCCATATTTTGCTATAGTGAGTTATTTTAGATGATTGAA

AATAACC
TTATTGG
```

Fig. 10A

ATGGAAGAAGATTTTGAAATTGTTTTTAATAAGGTTAAGCCAATTGTATGGAAATTAAG
CCGTTATTACTTTATTAAAATGTGGACTCGTGAAGATTGGCAACAAGAGGGAATGTTGA
TTTTGCACCAATTATTAAGGGAACATCCAGAATTAGAAGAGGATGATACAAAATTGTAT
ATCTATTTTAAGACACGTTTTTCTAATTACATTAAAGATGTTTTGCGTCAGCAAGAAAG
TCAGAAACGTCGTTTTAATAGAATGTCTTATGAAGAAGTCGGTGAGATTGAACACTGTT
TGTCAAGTGGCGGTATGCAATTGGATGAATATATTTTATTTCGTGATAGTTTGCTTGCA
TATAAACAAGGTCTGAGTACTGAAAAGCAAGAGCTGTTTGAGCGCTTGGTAGCAGGAGA
GCACTTTTTGGGAAGGCAAAGTATGCTGAAAGATTTACGTAAAAAATTAAGTGATTTTA
AGGAAAAA [SEQ ID NO: 28]

Fig. 10B

MEEDFEIVFNKVKPIVWKLSRYYFIKMWTREDWQQEGMLILHQLLREHPELEEDDTKLY
IYFKTRFSNYIKDVLRQQESQKRRFNRMSYEEVGEIEHCLSSGGMQLDEYILPRDSLLA
YKQGLSTEKQELFERLVAGEHFLGRQSMLKDLRKKLSDFKEK [SEQ ID NO: 29]

Fig. 10C

GTAAATAAAACAGCCAGTTAAGATGGGACATTTATGTCCTGTTCTTAAAGTCTTTTTCG
TTTTATAATAATTTTATTATAAAAGGAGGTCATCGTAATAGATGGAAGAAGATTTTGAA
ATTGTTTTTAATAAGGTTAAGCCAATTGTATGGAAATTAAGCCGTTATTACTTTATTAA
AATGTGGACTCGTGAAGATTGGCAACAAGAGGGAATGTTGATTTTGCACCAATTATTAA
GGGAACATCCAGAATTAGAAGAGGATGATACAAAATTGTATATCTATTTTAAGACACGT
TTTTCTAATTACATTAAAGATGTTTTGCGTCAGCAAGAAAGTCAGAAACGTCGTTTTAA
TAGAATGTCTTATGAAGAAGTCGGTGAGATTGAACACTGTTTGTCAAGTGGCGGTATGC
AATTGGATGAATATATTTTATTTCGTGATAGTTTGCTTGCATATAAACAAGGTCTGAGT
ACTGAAAAGCAAGAGCTGTTTGAGCGCTTGGTAGCAGGAGAGCACTTTTTGGGAAGGCA
AAGTATGCTGAAAGATTTACGTAAAAAATTAAGTGATTTTAAGGAAAAATAGTTAAAAA
GGGAAAGAATGGAACATGTGATTGTACCATTCTTTTTGGTTGAAAATTAAGAAAAGTTA
TTATAAATTATTGGTTTAACATGCCATATTA [SEQ ID NO: 30]

Fig. 11A

ATGAAACAAGTTATTTATGTTGTTTTAATCGTCATAGCCGTTAACATTCTCTTAGAGATT
ATCAAAAGAGTAACAAAAAGGGGAGGGACAGTTTCGTCATCTAATCCTTTACCAGATGGG
CAGTCTAAGTTGTTTTGGCGCAGACATTATAAGCTAGTACCTCAGATTGATACCAGAGAC
TGTGGGCCGGCAGTGCTGGCATCTGTTGCAAAGCATTACGGATCTAATTACTCTATCGCT
TATCTGCGGGAACTCTCAAAGACTAACAAGCAGGGAACAACAGCTCTTGGCATTGTTGAA
GCTGCTAAAAAGTTAGGCTTTGAAACACGCTCTATCAAGGCGGATATGACGCTTTTTGAT
TATAATGATTTGACCTATCCTTTTATCGTCCATGTGATTAAAGGAAAACGTCTGCAGCAT
TATTATGTCGTCTATGGCAGCCAGAATAATCAGCTGATTATTGGAGATCCTGATCCTTCA
GTTAAGGTGACTAGGATGAGTAAGGAACGCTTTCAATCAGAGTGGACAGGCCTTGCAATT
TTCCTAGCTCCTCAGCCTAACTATAAGCCTCATAAAGGTGAAAAAAATGGTTTGTCTAAT
TTCTTCCCGTTGATCTTTAAGCAGAAAGCTTTGATGACTTATATTATCATAGCTAGCTTG
ATTGTGACGCTCATTGATATTGTCGGATCATACTATCTCCAAGGAATATTGGACGAGTAC
ATTCCTGATCAGCTGATTTCAACTTTAGGAATGATTACGATTGGTCTGATAATAACCTAT
ATTATCCAGCAGGTCATGGCTTTTGCAAAAGAATACCTCTTGGCCGTACTCAGTTTGCGT
TTAGTCATTGATGTTATCCTGTCTTATATCAAACATATTTTTACGCTTCCTATGTCTTTC
TTTGCGACAAGGCGAACAGGAGAAATCACGTCTCGTTTTACAGATGCCAATCAGATTATT
GATGCTGTAGCGTCAACCATCTTTTCAATCTTTTAGATATGACTATGGTAATTTTGGTT
GGTGGGGTTTTGTTGGCGCAAAACAATAACCTTTTCTTTCTAACCTTGCTCTCCATTCCG
ATTTATGCCATCATTATTTTTGCTTTCTTGAAACCCTTTGAGAAAATGAATCACGAAGTG
ATGGAAAGCAATGCTGTGGTAAGTTCTTCTATCATTGAAGATATCAATGGGATGGAAACC
ATTAAATCACTCACAAGTGAGTCCGCTCGTTATCAAAACATTGATAGTGAATTTGTTGAT
TATTTGGAGAAAAACTTTAAGCTACACAAGTATAGTGCCATTCAAACCGCATTAAAAAGC
GGTGCTAAGCTTATCCTCAATGTTGTCATTCTCTGGTATGGCTCTCGTCTAGTTATGGAT
AATAAAATCTCAGTTGGTCAGCTTATCACCTTTAATGCTTTGCTGTCTTATTTCTCAAAT
CCAATTGAAAATATTATCAATCTGCAATCCAAACTGCAGTCAGCTCGCGTTGCCAATACA
CGTCTTAATGAGGTCTATCTTGTCGAATCTGAATTTGAAAAAGACGGCGATTTATCAGAA
AATAGCTTTTTAGATGGTGATATTTCGTTTGAAAATCTTTCTTATAAATATGGATTTGGG
CGAGATACCTTATCAGATATTAATTTATCAATCAAAAAAGGCTCCAAGGTCAGTCTAGTT
GGAGCCAGTGGTTCTGGTAAAACAACTTTGGCTAAACTGATTGTCAATTTCTACGAGCCT
AACAAGGGGATTGTTCGAATCAATGGCAATGATTTAAAAGTTATTGATAAGACAGCTTTG
CGGCGGCATATTAGCTATTTGCCGCAACAGGCCTATGTTTTTAGTGGCTCTATTATGGAT
AATCTCGTTTTAGGAGCTAAAGAAGGAACGAGTCAGGAAGACATTATTCGTGCTTGTGAA
ATTGCTGAAATCCGCTCGGACATTGAACAAATGCCTCAGGGCTATCAGACAGAGTTATCA
GATGGTGCCGGTATTTCTGGCGGTCAAAAACAGCGGATTGCTTTAGCTAGGGCCTTATTA
ACACAGGCACCGGTTTTGATTCTGGATGAAGCCACCAGCAGTCTTGATATTTTGACAGAA
AAGAAAATTATCAGCAATCTCTTACAGATGACGGAGAAAACAATAATTTTTGTTGCCCAC
CGCTTAAGCATTTCACAGCGTACTGACGAAGTCATTGTCATGGATCAGGGAAAAATTGTT
GAACAAGGCACTCATAAGGAACTTTTAGCTAAGCAAGGTTTCTATTATAACCTGTTTAAT
[SEQ ID NO: 31]

Fig. 11B

MKQVIYVVLIVIAVNILLEIIKRVTKRGGTVSSSNPLPDGQSKLFWRRHYKLVPQIDTRD
CGPAVLASVAKHYGSNYSIAYLRELSKTNKQGTTALGIVEAAKKLGFETRSIKADMTLFD
YNDLTYPFIVHVIKGKRLQHYYVVYGSQNNQLIIGDPDPSVKVTRMSKERFQSEWTGLAI
FLAPQPNYKPHKGEKNGLSNFFPLIFKQKALMTYIIIASLIVTLIDIVGSYYLQGILDEY
IPDQLISTLGMITIGLIITYIIQQVMAFAKEYLLAVLSLRLVIDVILSYIKHIFTLPMSF
FATRRTGEITSRFTDANQIIDAVASTIFSIFLDMTMVILVGGVLLAQNNNLFFLTLLSIP
IYAIIIFAFLKPFEKMNHEVMESNAVVSSSIIEDINGMETIKSLTSESARYQNIDSEFVD
YLEKNFKLHKYSAIQTALKSGAKLILNVVILWYGSRLVMDNKISVGQLITFNALLSYFSN
PIENIINLQSKLQSARVANTRLNEVYLVESEFEKDGDLSENSFLDGDISFENLSYKYGFG
RDTLSDINLSIKKGSKVSLVGASGSGKTTLAKLIVNFYEPNKGIVRINGNDLKVIDKTAL
RRHISYLPQQAYVFSGSIMDNLVLGAKEGTSQEDIIRACEIAEIRSDIEQMPQGYQTELS
DGAGISGGQKQRIALARALLTQAPVLILDEATSSLDILTEKKIISNLLQMTEKTIIFVAH
RLSISQRTDEVIVMDQGKIVEQGTHKELLAKQGFYYNLFN [SEQ ID NO: 32]

Fig. 11C

ATGGATCCTAAATTTTTACAAAGTGCAGAATTTTATAGGAGACGCTATCATAATTTTGCG
ACACTATTAATTGTTCCTTTGGTCTGCTTGATTATCTTCTTGGTCATATTCCTTTGTTTT
GCTAAAAAAGAAATTACAGTGATTTCTACTGGTGAAGTTGCACCAACAAAGGTTGTAGAT
GTTATCCAATCTTACAGTGACAGTTCAATCATTAAAAATAATTTAGATAATAATGCAGCT
GTTGAGAAGGGAGACGTTTTAATTGAATATTCAGAAAATGCCAGTCCAAACCGTCAGACT
GAACAAAAGAATATTATAAAAGAAAGACAAAAACGAGAAGAGAAGGAAAAGAAAAAACAC
CAAAAGAGCAAGAAAAAGAAGAAGTCTAAGAGCAAGAAAGCTTCCAAAGATAAGAAAAAG
AAATCGAAAGACAAGGAAAGCAGCTCTGACGATGAAAATGAGACAAAAAAGGTTTCGATT
TTTGCTTCAGAAGATGGTATTATTCATACCAATCCCAAATATGATGGTGCCAATATTATT
CCGAAGCAAACCGAGATTGCTCAAATCTATCCTGATATTCAAAAAACAAGAAAAGTGTTA
ATCACCTATTATGCTTCTTCTGATGATGTTGTTTCTATGAAAAAGGGGCAAACCGCTCGT
CTTTCCTTGGAAAAAAAGGGAAATGACAAGGTTGTTATTGAAGGAAAAATTAACAATGTC
GCTTCATCAGCAACTACTACTAAAAAAGGAAATCTCTTTAAGGTTACTGCCAAAGTAAAG
GTTTCTAAGAAAAATAGCAAACTCATCAAGTATGGTATGACAGGCAAGACAGTCACTGTC
ATTGATAAAAAGACTTATTTTGATTATTTCAAAGATAAATTACTGCATAAAATGGATAAT
[SEQ ID NO: 33]

Fig. 11D

MDPKFLQSAEFYRRRYHNFATLLIVPLVCLIIFLVIFLCFAKKEITVISTGEVAPTKVVD
VIQSYSDSSIIKNNLDNNAAVEKGDVLIEYSENASPNRQTEQKNIIKERQKREEKEKKKH
QKSKKKKKSKSKKASKDKKKKSKDKESSSDDENETKKVSIFASEDGIIHTNPKYDGANII
PKQTEIAQIYPDIQKTRKVLITYYASSDDVVSMKKGQTARLSLEKKGNDKVVIEGKINNV
ASSATTTKKGNLFKVTAKVKVSKKNSKLIKYGMTGKTVTVIDKKTYFDYFKDKLLHKMDN
[SEQ ID NO: 34]

SIGNAL PEPTIDES, NUCLEIC ACID MOLECULES AND METHODS FOR TREATMENT OF CARIES

CROSS REFERENCE TO RELATED APPLICATIONS

This application is a continuation-in-part of U.S. patent application Ser. No. 09/833,017 filed Apr. 10, 2001, now U.S. Pat. No. 6,923,962, which claims the benefit under 35 U.S.C. § 119(e) of U.S. Provisional Patent Application No. 60/269,949 filed Feb. 20, 2001. The disclosures of said applications are hereby incorporated herein by reference.

BACKGROUND OF INVENTION

1. Field of the Invention

The invention generally relates to compounds and methods that inhibit or disrupt microbial biofilms involved in infections in man and animals and in biofouling of surfaces susceptible to microbial accumulation.

2. Description of the Related Art

Bacteria often attach and accumulate on surfaces, enabling them to resist removal and killing by mechanical and chemical means. This can result in persistent and chronic infections and fouling of devices that are in contact with liquids containing the colonizing bacteria. Bacteria respond to signals resulting from the proximity, density, and identity of microbial neighbors. Through the process of quorum sensing (QS), bacteria can indirectly determine population density by sensing concentration of a secreted signal molecule (Bassler, 2002). The ability of bacteria to communicate with one another by QS and behave collectively as a group confers significant advantages, including more efficient proliferation, better access to resources and niches, and a stronger defense against competitors (Jefferson, 2004). Many QS systems having various effects on bacterial cell physiology have been studied. Examples include biofilm differentiation in *Pseudomonas aeruginosa* (Davies et al., 1998), swarming motility in *Serratia liquefaciens* (Eberl et al., 1999), competence development in *Streptococcus pneumoniae* (Lee and Morrison, 1999) and *Streptococcus mutans* (Li et al., 2001), and induction of virulence factors in *Staphylococcus aureus* (Ji et al., 1995).

Controlling bacterial biofilms is desirable for almost every human enterprise in which solid surfaces are introduced into non-sterile aqueous environments. U.S. Pat. No. 6,024,958 describes peptides that attempt to control biofilm formation by preventing bacterial adherence to teeth. In addition to occurrence in dental caries, medical examples of biofilm growth include cases involving indwelling medical devices, joint implants, prostatitis, endocarditis, and respiratory infections. In fact, the Centers for Disease Control and Prevention (CDC; Atlanta, Ga.) estimate that 65% of human bacterial infections involve biofilms. Non-medical examples of biofilm colonization are water and beverage lines, cooling towers, radiators, aquaculture contamination, submerged pumps and impellers, hulls of commercial, fishing and military vessels and literally every situation where biofouling occurs. The potential benefits of basic research focused at biofilm physiology and genetics with the ultimate goal of controlling surface-mediated microbial growth are limitless.

Interest in the study of biofilm-grown cells has increased partly because biofilm growth provides a microenvironment for cells to exist in a physical and physiological state that can increase their resistance to antimicrobial compounds and mechanical forces (reviewed in Costerton and Lewandowski, *Adv Dent Res,* 11:192-195). Growth in biofilms can also facilitate the transfer of genetic information between different species (Christensen et al. Appl Environ Microbiol, 64:2247-2255). Recent evidence suggests that biofilm-grown cells may display a dramatically different phenotype when compared with their siblings grown in liquid culture. In some, this altered physiological state has been shown to result from gene activation initiated by contact with surfaces (Finlay and Falkow. Microbiol. Molec Rev, 61:136-169) or from signal molecules produced by the bacteria allowing them to sense the cell density (quorum sensing) (Davies et al. Appl Environ Microbiol, 61:860-867). Biofilms may also act as 'genotypic reservoirs', allowing persistence, transfer and selection of genetic elements conferring resistance to antimicrobial compounds.

*Streptococcus mutans* is the principal etiological agent of dental caries in humans. None of the known types of *S. mutans* antibiotics has satisfactorily controlled caries. There is a need to identify new ways to control *S. mutans* induced caries.

SUMMARY OF THE INVENTION

In accordance with certain embodiments of the present invention a compound is provided that competitively inhibits binding of CSP [SEQ ID NO:1] to *S. mutans* histidine kinase [SEQ ID NO:2]. In certain embodiments the compound is a peptide or an antibody. In some embodiments the compound is a derivative of SEQ ID NO:5, a fragment of SEQ ID NO:5 or a derivative of a fragment of SEQ ID NO:5.

In accordance with certain embodiments of the present invention methods of making an above-described compound are provided. In still other embodiments of the invention methods are provided in which an above-described compound is used for inhibiting the growth of *S. mutans*, for inhibiting dental caries, or for improving dental health. These and other embodiments, features and advantages of the invention will be apparent with reference to the following description and drawings.

BRIEF DESCRIPTION OF THE DRAWINGS

FIG. 1 shows the schematic layout of the arrangement of the genetic locus encoding the signal peptide precursor (ComC) [SEQ ID NO:4], the histidine kinase (ComD) [SEQ ID NO:2] and the response regulator (ComE) [SEQ ID NO:3]. Note that this arrangement is different from other loci in related streptococci for the following reasons: a). The comC gene [SEQ ID NO:4] is transcribed from its own unique promoter, unlike the genes thus far described in other streptococci that are arranged in an operon-like cluster with the comC/DE genes being transcribed from a single promoter, b) The comC gene [SEQ ID NO:4] is separated by 148 nucleotides from the comD gene [SEQ ID NO:6].

FIG. 2 shows the nucleic acid molecule that is SEQ ID NO:4. In a preferred embodiment, the figure shows a nucleic acid encoding CSP (competence signal peptide [SEQ ID NO:5]). FIG. 2 also shows histidine kinase [SEQ ID NO:6] sequences and response regulator [SEQ ID NO:7] sequences. FIG. 2A. *S. mutans* comC gene [SEQ ID NO:4]. Encodes a precursor to a signal peptide [SEQ ID NO:1]. FIG. 2B. *S. mutans* CSP encoding sequence [SEQ ID NO:5]. Encodes a Competence Signal Peptide [SEQ ID NO:11]. FIG. 2C. *S. mutans* comD gene [SEQ ID NO:6]. Encodes a response regulator that activates transcription of a number of genes. FIG. 2D. *S. mutans* comE gene [SEQ ID NO:7].

FIG. 3. Sequence of the deduced amino acid sequence of the signal peptide [SEQ ID NO:1], histidine kinase [SEQ ID NO:2], and response regulator [SEQ ID NO:3]. FIG. 3A. *S. mutans* ComC protein (CSP Precursor) [SEQ ID NO:1]. FIG. 3B. *S. mutans* ComD protein (Histidine Kindase) [SEQ ID NO:2]. FIG. 3C. *S. mutans* ComE protein (Response Regulator) [SEQ ID NO:3].

FIG. 4. The deduced amino acid sequence of the signal peptide precursor in various strains and its predicted cleavage site. The original peptide is expressed as a 46 amino acid peptide that is cleaved after the glycine-glycine residues to generate an active signal peptide.

FIG. 5 shows the peptide that is SEQ ID NO:11. The synthetic signal peptide is effective at inducing competence, biofilm formation and acid tolerance in *Streptococcus mutans*.

FIG. 8 is a list of the primers used to amplify the genes or internal regions of the target genes by polymerase chain reaction (PCR) for subsequent sequencing or inactivation.

FIG. 9 shows the ComCDE local region [SEQ ID NO:18 and SEQ ID NO:19]. The ComC (first highlighted region; nucleotide 101 to 241), ComD (second highlighted region; nucleotides 383 to 1708) and ComE (third highlighted region; nucleotides 1705 to 2457) proteins are highlighted.

FIG. 10 shows the comX DNA sequence [SEQ ID NO:28], protein sequence [SEQ ID NO:29], and the comX gene local region [SEQ ID NO:30] with 100 bp included both upstream and downstream (promoter is upstream). FIG. 10A. *S. mutans* comX gene [SEQ ID NO:28]. FIG. 10B. *S. mutans* ComX protein [SEQ ID NO:29]. FIG. 10C. *S. mutans* comX gene local region [SEQ ID NO:30].

FIG. 11 shows the comA and comB nucleotide [SEQ ID NO:31] and [SEQ ID NO:33] and amino acid sequences [SEQ ID NO:32] and [SEQ ID NO:34]. ComA and ComB are the components of the CSP exporter. FIG. 11A. *S. mutans* comA gene [SEQ ID NO:31]. FIG. 11B. *S. mutans* ComA protein [SEQ ID NO:32]. FIG. 11C. *S. mutans* comB gene [SEQ ID NO:33] FIG. 11D. *S. mutans* ComB protein [SEQ ID NO:34].

DETAILED DESCRIPTION OF THE PREFERRED EMBODIMENTS

Figures 6, 7:
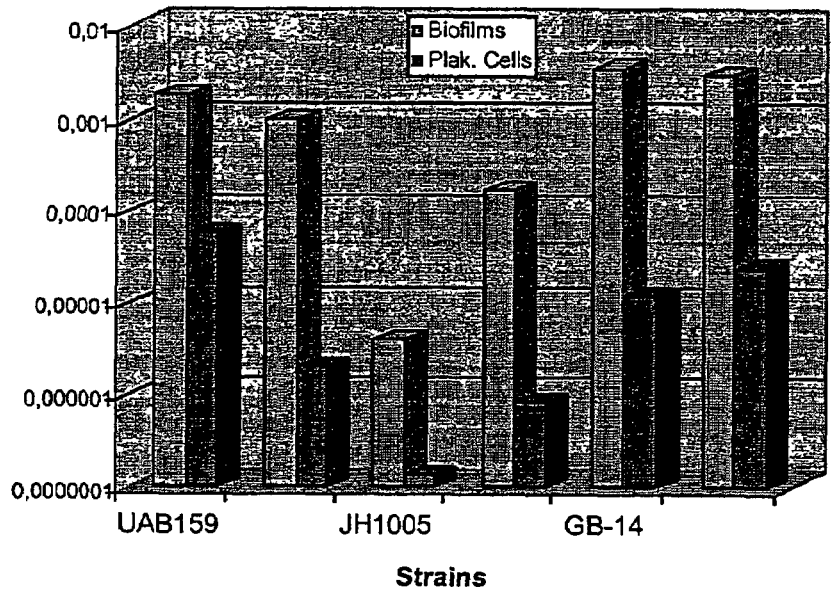
FIG. 6 shows the natural activity of the signal/receptor system functioning in vitro in model biofilms as determined by the ability of various strains of *S. mutans* to accept donor plasmid DNA conferring erythromycin resistance.
FIG. 7 is a table illustrating the effect of synthetic peptide on genetic competence in *S. mutans* cells. Induction of genetic transformation in *Streptococcus mutans* by synthetic competence stimulating peptide (SCSP).
Figure 12:
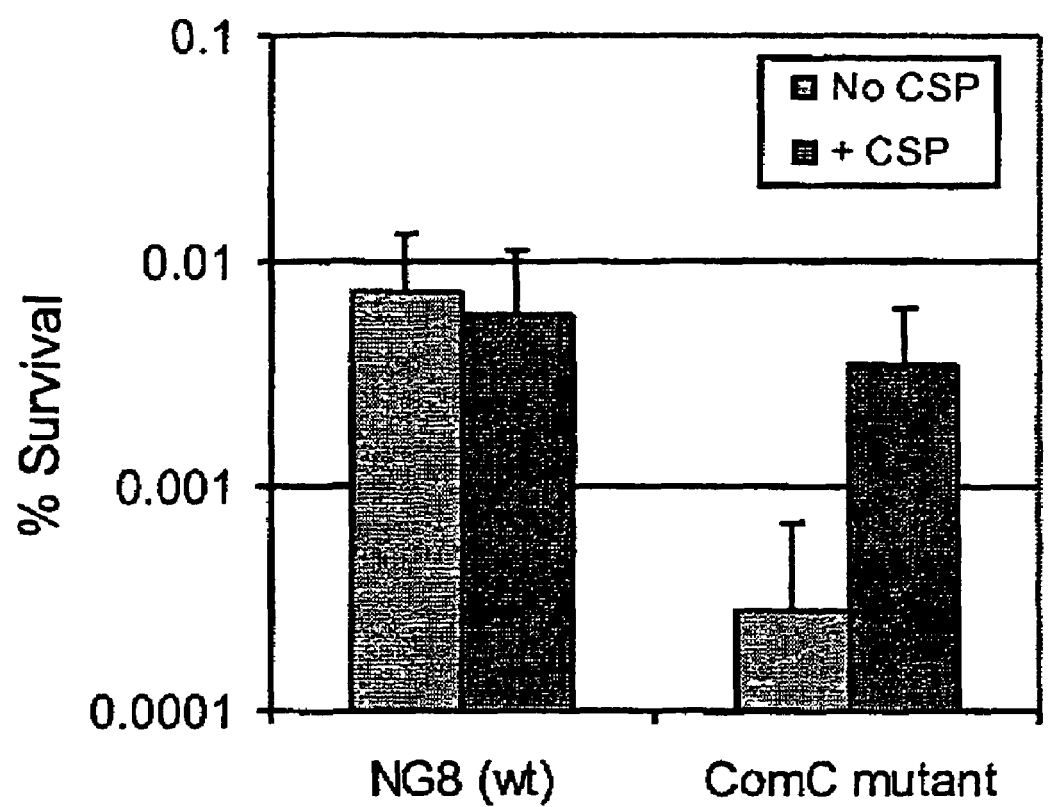
FIG. 12 illustrates the effect of synthetic peptide on acid resistance tolerance in *S. mutans* comC deficient cells. Addition of synthetic signal peptide (CSP) [SEQ ID NO:11] into the culture of the comC mutant restored the ability of the mutant to survive a low pH challenge when compared to the parent strain NG8.
Figure 13:
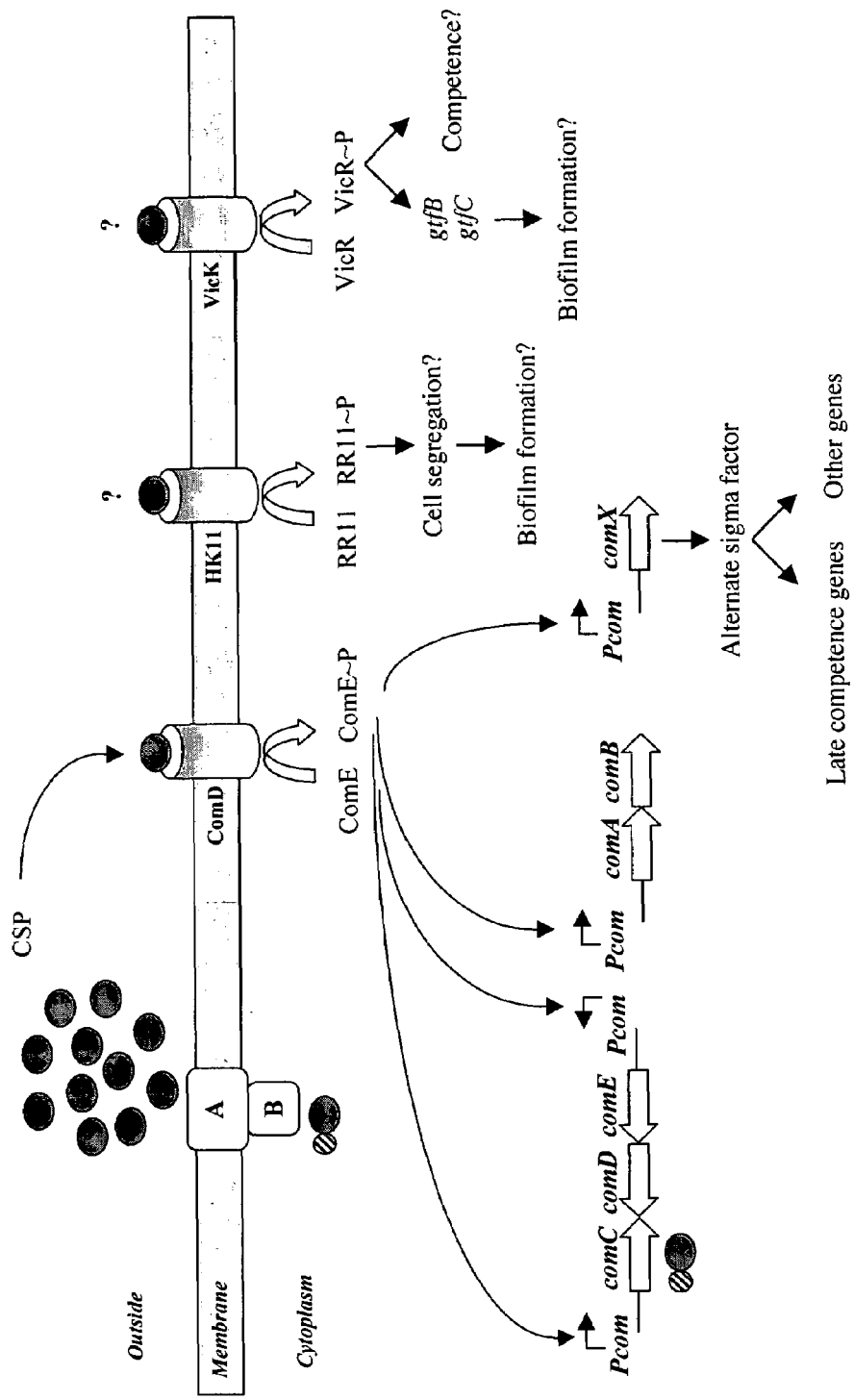
FIG. 13 is a schematic representation of quorum sensing circuit in *S. mutans*.
Figure 14:
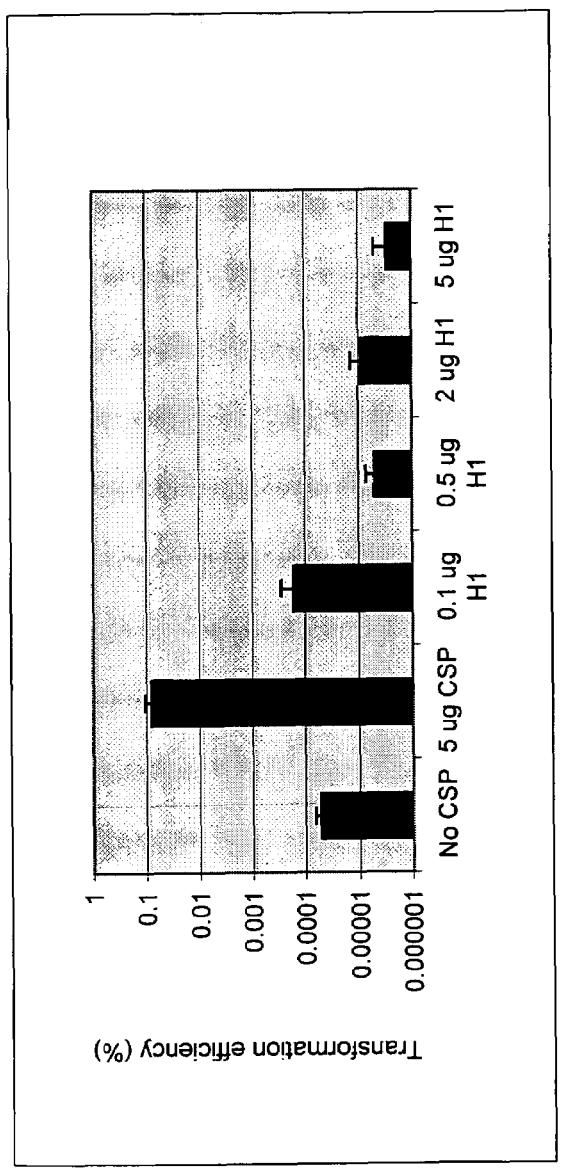
FIG. 14 shows the effect of different concentrations of H1 on genetic transformation of *S. mutans* wild-type UA159. Results are expressed as the mean±SE of three independent experiments.
Figure 15:
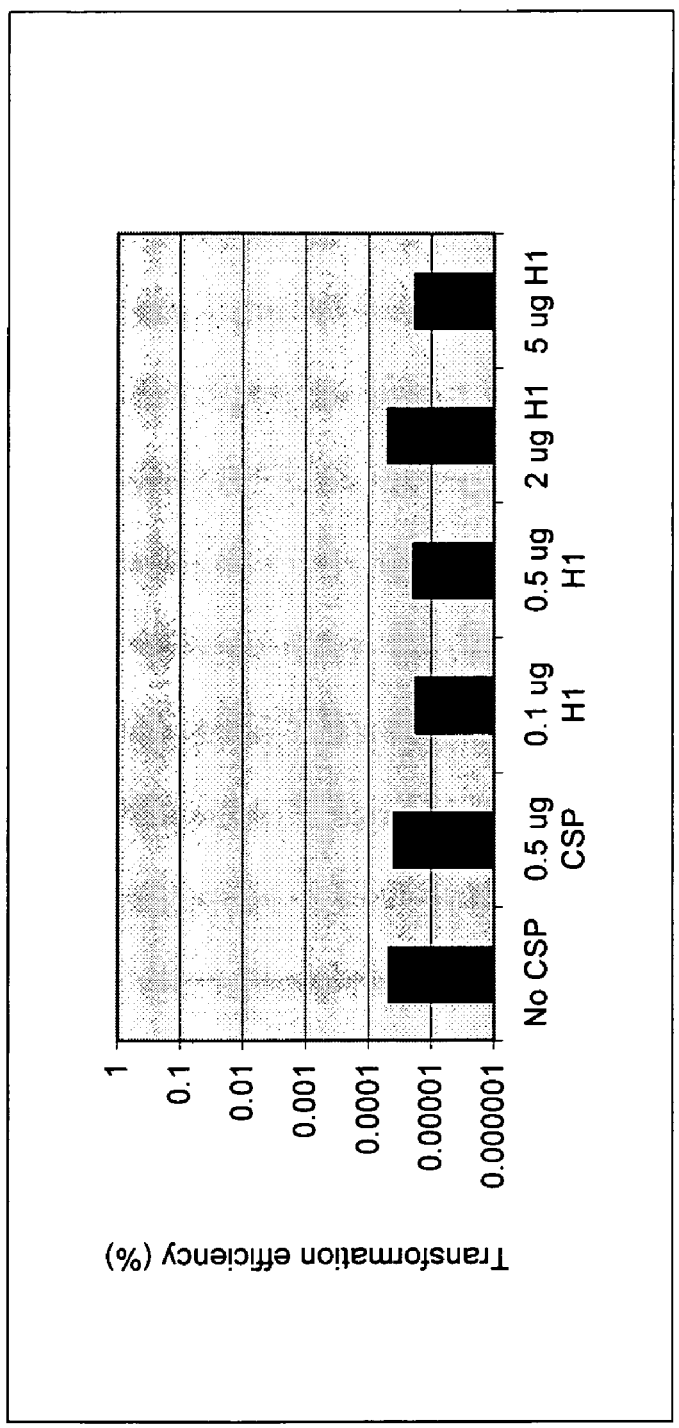
FIG. 15 shows the effect of different concentrations of H1 on genetic transformation of *S. mutans* comD null mutant.
Figure 16:
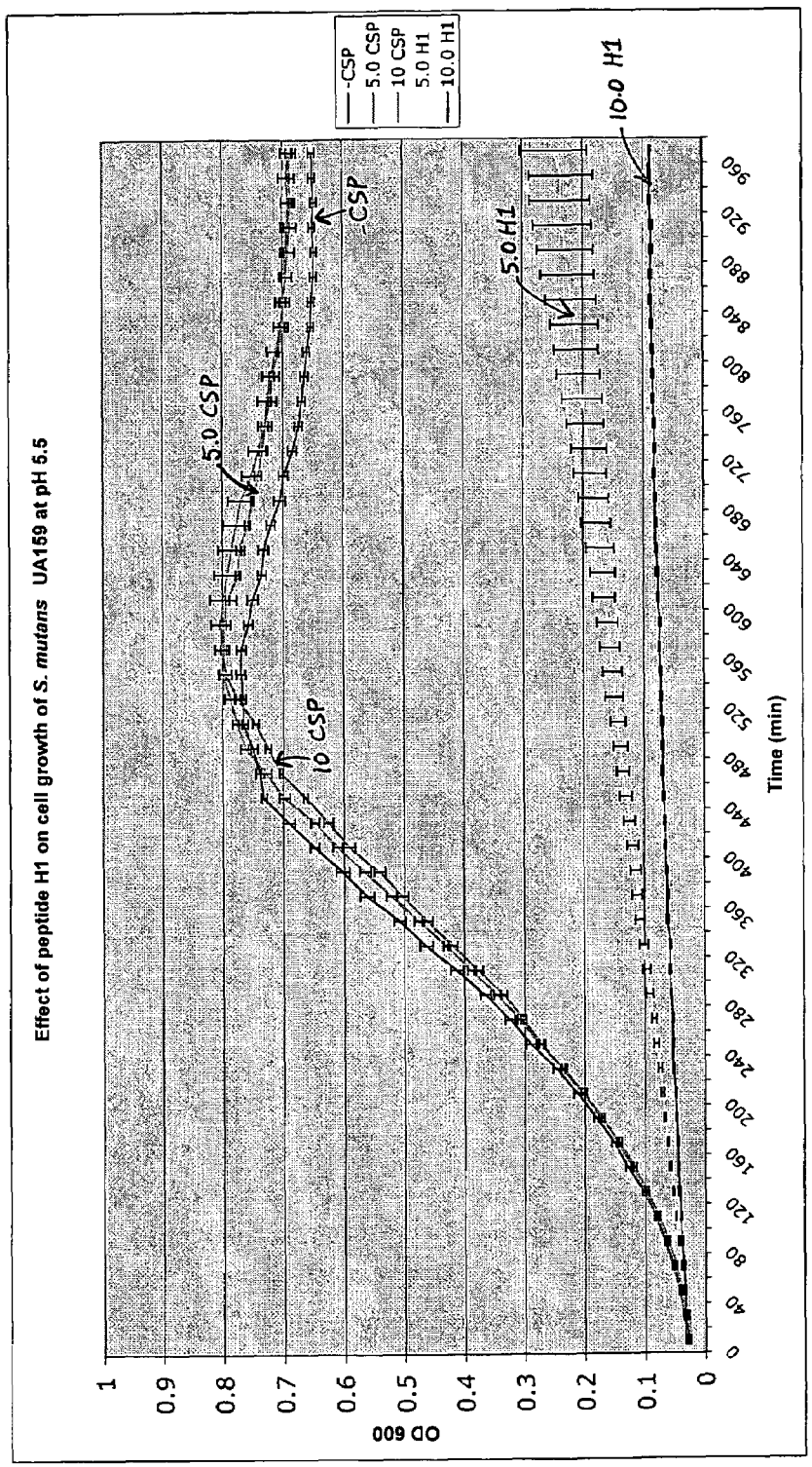
FIG. 16 shows the effect of different concentrations (μg/ml) of CSP and H1 on cell growth of *S. mutans* wild-type UA159 in THYE at pH 5.5. Means $OD_{600}$ values±SE, Results represent the average of three independent experiments.
Figure 17:
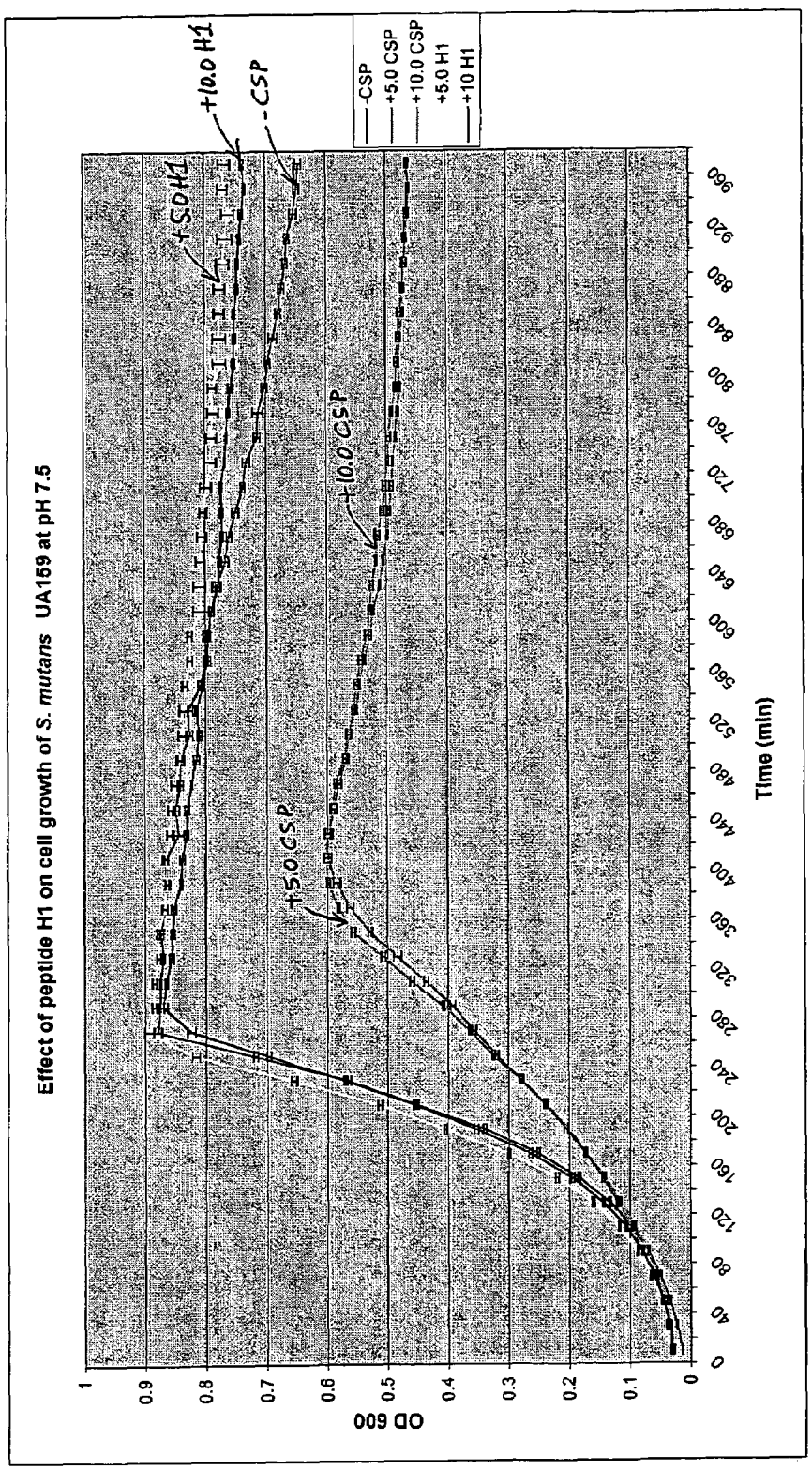
FIG. 17 effect of different concentrations (μg/ml) of CSP and H1 on cell growth of *S. mutans* wild-type UA159 in THYE at pH 7.5. Means $OD_{600}$ values±SE. Results represent the average of three independent experiments.

In some Gram-positive bacteria (including *Streptococcus mutans*), when a specific histidine kinase receptor located in the cell membrane is disrupted, the cells become ineffective at developing a biofilm. The cells growing in this biofilm environment use a small peptide signal molecule to activate the receptor in surrounding cells, thereby communicating the message to form a biofilm. This same signal peptide and histidine kinase are also involved in the induction of genetic competence, the cell's ability to take up and incorporate DNA from its extracellular environment, as well as that of acid tolerance, the cell's ability to survive pH levels as low as pH 3.0. A mechanism that blocks the signal molecule from activating the histidine kinase receptor molecule provides a novel method for controlling microbial biofilms, either alone or in combination with chemical or physical means.

We have identified a genetic locus in *S. mutans* consisting of three genes that encode: 1) a peptide precursor [SEQ ID NO:1] that is processed during export into a secreted 21-amino acid peptide (CSP) [SEQ ID NO:11]; 2) a histidine kinase [SEQ ID NO:2] that acts as a cell surface receptor activated by the peptide; 3) a response regulator [SEQ ID NO:3] that activates a number of other genes involved in genetic competence, biofilm formation, and acid tolerance of *S. mutans*. These properties have been attributed to the bacterium's ability to cause dental caries. Inactivation of any of these three genes or impairment of interaction or activity of any of their encoded proteins will disrupt the bacterium's ability to take up foreign DNA, form biofilms, and tolerate acidic pH.

*Streptococcus mutans* is a resident of the biofilm environment of dental plaque, a matrix of bacteria and extracellular material that adheres to the tooth surface. Under appropriate environmental conditions populations of *S. mutans* and the pH of the surrounding plaque will drop. *S. mutans*, being among the most acid tolerant organisms residing in dental plaque, will increase its numbers in this acidic environment and eventually become a dominant member of the plaque community. This situation eventually leads to dissolution of the tooth enamel, resulting in the development of dental caries. We control the accumulation and acid tolerance of this bacterium to make it less able to cause caries. We accomplish this by using inhibitors of an extracellular signal peptide that promotes the expression of genes involved in *S. mutans* biofilm formation and acid tolerance. Compounds are disclosed that inhibit the action of the peptide. These inhibitors can include peptides, antibodies, or other agents that specifically inhibit the activation of the histidine kinase and the family of genes activated as a result of the histidine kinase activation by the signal molecule. Inhibitors include: modified structures of the peptide where amino acids are removed from the N- and/or COOH terminal of the peptide and/or substitutions of internal amino acid residues. We delete, one, two to 5, 6 to 10 and 10 to 15 amino acids from the peptide (for example at either terminal) and measure competitive inhibition of signal peptide binding to histidine kinase (1, 2, 3, 4, 5, 6, 7, 8, 9, or 10 or more amino acids are deleted and inhibition measured). Inhibitors also include antibodies raised against the 21-amino acid CSP [SEQ ID NO:11] alone or coupled to a larger molecule to increase immunogenicity. We also test inhibitors described in Barrett et al. Proc. Natl. Acad. Sci. USA 95:5317-5322) and measure competitive inhibition of signal peptide binding to histidine kinase.

In addition to identifying the genes encoding this signaling/sensing system, we have identified and chemically synthesized a 21-amino acid peptide [SEQ ID NO:11] that promotes biofilm formation and acid tolerance of *S. mutans*. A survey of the literature and genome databases reveals that genes similar to this signal-receptor system are present in most Gram-positive bacteria, and therefore an inhibitor, or family of related inhibitors may be effective at inhibiting biofilm formation among a large group of bacteria.

Treatment or prevention of dental caries comprises addition of compounds that inhibit the stimulatory action of the 21-amino acid peptide [SEQ ID NO:11] on biofilm formation and acid tolerance of *S. mutans*. This is accomplished by delivery of these compounds to the biofilm and/or to incorporate these inhibitors into materials to control growth on surfaces. This includes delivery by topical application, alone or in combination with other compounds including toothpaste, mouthwash, food or food additives.

*Streptococcus mutans* is also implicated in causing infective endocarditis. Inhibitors of biofilm formation, and hence aggregation are useful in the treatment of these bacterial infections as well.

Identification and characterization of Competence Signal Peptide (CSP), Histidine Kinase (UK) and Response Regulator (RR)

Competence Signal Peptide

An isolated CSP from *S. mutans* is provided in accordance with certain embodiments of the present invention. Also provided in accordance with certain embodiments of the present invention is a recombinant isolated CSP [SEQ ID SEQ 11] peptide produced by a cell including a nucleic acid molecule encoding CSP [SEQ ID NO:5] operably linked to a promoter. Further provided in accordance with certain embodiments of the present invention is an isolated nucleic acid molecule encoding a CSP [SEQ ID NO:5]. The peptide we work with is preferably chemically synthesized.

CSP-encoding nucleic acid molecules [SEQ ID NO:5] and molecules having sequence identity or which hybridize to the CSP-encoding sequence and which encode a peptide having CSP activity (preferred percentages for sequence identity are described below) as well as vectors including these molecules are provided in accordance with various embodiments of the present invention. In certain embodiments of the invention, CSP [SEQ ID NO:11] or peptides having sequence identity (preferred percentages described below) or which have CSP activity are provided. The nucleic acid molecules and peptides disclosed herein may be from *S. mutans* and they may be isolated from a native source, synthetic or recombinant. CSP [SEQ ID NO:11] or peptides having sequence identity, which have CSP activity, as prepared by the processes described in this application, are also provided in accordance with the present invention.

Histidine Kinase

In accordance with certain embodiments of the present invention, an isolated HK [SEQ ID NO:2] from *S. mutans* is disclosed. Also disclosed is a recombinant isolated HK polypeptide produced by a cell including a nucleic acid molecule encoding HK [SEQ ID NO:6] operably linked to a promoter. In another embodiment of the invention an isolated nucleic acid molecule encoding a HK polypeptide [SEQ ID NO:2] is disclosed.

HK-encoding nucleic acid molecules and molecules having sequence identity or which hybridize to the HK-encoding sequence [SEQ ID NO:6] and which encode a protein having HK activity (preferred percentages for sequence identity are described below) as well as vectors including these molecules are disclosed as part of the present invention. In accordance with some embodiments of the present invention, HK [SEQ ID NO:2] or polypeptides having sequence identity (preferred percentages described below) or which have HK activity are disclosed. The nucleic acid molecules and polypeptides disclosed herein may be from *S. mutans* and they may be isolated from a native source, synthetic or recombinant. Also provided according to certain embodiments of the present invention is HK [SEQ ID NO:2] or polypeptides having sequence identity, which have HK activity, as prepared by the processes described in this application.

Response Regulator

In accordance with certain embodiments of the present invention an isolated RR [SEQ ID NO:3] from *S. mutans* is disclosed. A recombinant isolated RR [SEQ ID NO:3] polypeptide produced by a cell including a nucleic acid molecule encoding RR [SEQ ID NO:7] operably linked to a promoter is provided according to certain other embodiments of the present invention. Still other embodiments of the invention include an isolated nucleic acid molecule encoding a RR polypeptide.

Certain embodiments of the invention include RR-encoding nucleic acid molecules and molecules having sequence identity or which hybridize to the RR-encoding sequence [SEQ ID NO:7] and which encode a polypeptide having RR activity (preferred percentages for sequence identity are described below) as well as vectors including these molecules. Some embodiments of the invention also include RR [SEQ ID NO:3] or polypeptides having sequence identity (preferred percentages described below) or which have RR activity. The nucleic acid molecules and polypeptides of the invention may be from *S. mutans* and they may be isolated from a native source, synthetic or recombinant. Certain embodiments of the invention include RR [SEQ ID NO:3] or polypeptides having sequence identity, which have RR activity, as prepared by the processes described in this application.

The comA and comB nucleotide [SEQ ID NO:31 and SEQ ID NO:33] and amino acid sequences [SEQ ID NO:32 and SEQ ID NO:34] are also aspects of certain embodiments of the invention. ComA and ComB are components of the CSP exporter. The discussion of variants, sequence identity etc. for CSP, HK, RR applies to both the full sequences shown in the figures as well as bracketed portions of sequences (coding regions). The peptides and polypeptides may be natural, recombinantly produced or synthetic.

Functionally Equivalent Nucleic Acid Molecules

Certain embodiments of the invention include nucleic acid molecules that are functional equivalents of all or part of the CSP sequence in SEQ ID NO:5. (A nucleic acid molecule may also be referred to as a DNA sequence or nucleotide sequence in this application. All these terms have the same meaning as nucleic acid molecule). Functionally equivalent nucleic acid molecules are DNA and RNA (such as genomic DNA, complementary DNA, synthetic DNA, and messenger RNA molecules) that encode peptides having the same or similar CSP activity as the CSP peptide shown in SEQ ID NO:11. Functionally equivalent nucleic acid molecules can encode peptides that contain a region having sequence identity to a region of a CSP peptide [SEQ ID NO:11] or more preferably to the entire CSP peptide. Identity is calculated according to methods known in the art. The ClustalW program (preferably using default parameters) [Thompson, J D et al., Nucleic Acid Res. 22:4673-4680.], described below, is most preferred. For example, if a nucleic acid molecule (called "Sequence A") has 90% identity to a portion of the nucleic acid molecule in SEQ ID NO:5, then Sequence A will preferably be identical to the referenced portion of the nucleic acid molecule in SEQ ID NO:5, except that Sequence A may include up to 10 point mutations, such as substitutions with other nucleotides, per each 100 nucleotides of the referenced portion of the nucleic acid molecule in SEQ ID NO:5. Mutations described in this application preferably do not disrupt the reading frame of the coding sequence. Nucleic acid molecules functionally equivalent to the CSP sequences can occur in a variety of forms as described below.

Nucleic acid molecules may encode conservative amino acid changes in CSP peptide [SEQ ID NO:11]. Certain embodiments of the invention include functionally equivalent nucleic acid molecules that encode conservative amino acid changes within a CSP amino acid sequence and produce silent amino acid changes in CSP.

Nucleic acid molecules may encode non-conservative amino acid substitutions, additions or deletions in CSP peptide. Some embodiments of the invention include functionally equivalent nucleic acid molecules that make non-conservative amino acid changes within the CSP amino acid sequence in SEQ ID NO:11. Functionally equivalent nucleic acid molecules include DNA and RNA that encode peptides, peptides and proteins having non-conservative amino acid substitutions (preferably substitution of a chemically similar amino acid), additions, or deletions but which also retain the same or similar CSP activity as the CSP peptide shown in SEQ ID NO:11. The DNA or RNA can encode fragments or variants of CSP. Fragments are useful as immunogens and in immunogenic compositions (U.S. Pat. No. 5,837,472). The CSP or CSP-like activity of such fragments and variants is identified by assays as described below. Fragments and variants of CSP encompassed by the present invention should preferably have at least about 40%, 60%, 80% or 95% sequence identity to the naturally occurring CSP nucleic acid molecule, or a region of the sequence, such as the coding sequence or one of the conserved domains of the nucleic acid molecule, without being identical to the sequence in SEQ ID NO:11. Sequence identity is preferably measured with the ClustalW program (preferably using default parameters) (Thompson, J D et al., Nucleic Acid Res. 22:4673-4680).

Nucleic acid molecules functionally equivalent to the CSP nucleic acid molecule in SEQ ID NO:5 will be apparent from the following description. For example, the sequence shown in SEQ ID NO:5 may have its length altered by natural or artificial mutations such as partial nucleotide insertion or deletion, so that when the entire length of the coding sequence within SEQ ID NO:5, is taken as 100%, the functional equivalent nucleic acid molecule preferably has a length of about 60-120% thereof, more preferably about 80-110% thereof. Fragments may be less than 60%.

Nucleic acid molecules containing partial (usually 80% or less, preferably 60% or less, more preferably 40% or less of the entire length) natural or artificial mutations so that some codons in these sequences code for different amino acids, but wherein the resulting peptide retains the same or similar CSP activity as that of a naturally occurring CSP peptide [SEQ ID NO:11]. The mutated DNAs created in this manner should preferably encode a peptide having at least about 40%, preferably at least about 60%, at least about 80%, and more preferably at least about 90% or 95% sequence identity to the amino acid sequence of the CSP peptide in SEQ ID NO:11. The ClustalW program preferably assesses sequence identity.

Since the genetic code is degenerate, the nucleic acid sequence in SEQ ID NO:5 is not the only sequence which may code for a peptide having CSP activity. This invention includes nucleic acid molecules that have the same essential genetic information as the nucleic acid molecule described in SEQ ID NO:5. Nucleic acid molecules (including RNA) having one or more nucleic acid changes compared to the sequences described in this application and which result in production of a peptide shown in SEQ ID NO:11 are within the scope of various embodiments of the invention.

Other functional equivalent forms of CSP-encoding nucleic acids can be isolated using conventional DNA-DNA or DNA-RNA hybridization techniques. Thus, certain embodiments of the present invention also include nucleic acid molecules that hybridize to one or more of the sequences in SEQ ID NO:5 or its complementary sequence, and that encode expression for peptides, peptides and proteins exhibiting the same or similar activity as that of the CSP peptide produced by the DNA in SEQ ID NO:5 or its variants. Such nucleic acid molecules preferably hybridize to the sequence in SEQ ID NO:5 under moderate to high stringency conditions (see Sambrook et al. Molecular Cloning: A Laboratory Manual, Most Recent Edition, Cold Spring Harbor Laboratory Press, Cold Spring Harbor, N.Y.). High stringency washes have low salt (preferably about 0.2% SSC), and low stringency washes have high salt (preferably about 2% SSC). A temperature of about 37° C. or about 42° C. is considered low stringency, and a temperature of about 50-65° C. is high stringency. Some embodiments of the invention also include a method of identifying nucleic acid molecules encoding a CSP activator peptide (preferably a mammalian peptide), including contacting a sample containing nucleic acid molecules including all or part of SEQ ID NO:5 (preferably at least about 15 or 20 nucleotides of SEQ ID NO:5) under moderate or high stringency hybridization conditions and identifying nucleic acid molecules which hybridize to the nucleic acid molecules including all or part of SEQ ID NO:5. Similar methods are described in U.S. Pat. No. 5,851,788, which is incorporated by reference in its entirety.

Certain embodiments of the present invention also include methods of using all or part of the nucleic acid molecules which hybridize to all or part of SEQ ID NO:5, for example as probes or in assays to identify antagonists or inhibitors of the peptides produced by the nucleic acid molecules (described below). Some embodiments of the present invention include methods of using nucleic acid molecules having sequence identity to the CSP nucleic acid molecule (as described below) in similar methods.

Certain embodiments of the invention also include a nucleic acid molecule detection kit including, preferably in a suitable container means or attached to a surface, a nucleic acid molecule as disclosed herein encoding CSP [SEQ ID NO:5] or a peptide having CSP activity and a detection reagent (such as a detectable label). Other variants of kits will be apparent from this description and teachings in patents such as U.S. Pat. Nos. 5,837,472 and 5,801,233, which are incorporated by reference in their entirety.

A nucleic acid molecule described above is considered to have a function substantially equivalent to the CSP nucleic acid molecules [SEQ ID NO:5] of the present invention if the peptide [SEQ ID NO:11] produced by the nucleic acid molecule has CSP activity. A peptide has CSP activity if it can stimulate genetic competence and acid tolerance in *S. mutans*. Activation of the HK [SEQ ID NO:2]/RR [SEQ ID NO:3] is shown where a peptide is capable of stimulating the uptake and incorporation of foreign DNA. We describe below how the activity of these peptide-mediated processes can be measured by determining the efficiency of plasmid uptake, which is a measure of genetic competence. Since the ability to transport and incorporate foreign DNA relies on activation of the HK [SEQ ID NO:2]/RR [SEQ ID NO:3] and subsequent genes activated by the signal cascade initiated by the signal peptide, measurement of the conferment of erythromycin resistance by cells exposed to the peptide and plasmid DNA conferring erythromycin resistance indicates its level of function. Conversely if an inhibitor is capable of interfering with the action of the peptide the competence assay will indicate this by a corresponding decrease in the number of cells that acquire erythromycin resistance as described in the assays below (assays of genetic competence and assay of transformation of biofilms). Activation of the HK [SEQ ID NO:2]/RR [SEQ ID NO:3] is also shown where a peptide is capable of stimulating an acid tolerance response. We describe below how the activity of these peptide-mediated processes can be measured by determining the survival rate of cells in acidic pH conditions. Since the ability to survive exposure to acidic pH depends on the activation of the HK/RR and subsequent genes activated by the signal peptide, measurement of the survival of S. mutans in low pH conditions indicates the level of function of the signal peptide. Conversely, if an inhibitor is capable of interfering with the signal peptide sensing system the assay for acid adaptation will indicate this by a corresponding decrease in the survival rate of cells grown in acidic pH conditions as described in the assay below (assay of acid adaptation).

Production of CSP in Eukaryotic and Prokaryotic Cells

The nucleic acid molecules disclosed herein may be obtained from a cDNA library. The nucleotide molecules can also be obtained from other sources known in the art such as expressed sequence tag analysis or in vitro synthesis. The DNA described in this application (including variants that are functional equivalents) can be introduced into and expressed in a variety of eukaryotic and prokaryotic host cells. A recombinant nucleic acid molecule for the CSP contains suitable operatively linked transcriptional or translational regulatory elements. Suitable regulatory elements are derived from a variety of sources, and they may be readily selected by one with ordinary skill in the art (Sambrook, J, Fritsch, E. E. & Maniatis, T. (Most Recent Edition). Molecular Cloning: A Laboratory Manual. Cold Spring Harbor Laboratory Press. New York; Ausubel et al. (Most Recent Edition). Current Protocols in Molecular Biology, John Wiley & Sons, Inc.). For example, if one were to upregulate the expression of the nucleic acid molecule, one could insert a sense sequence and the appropriate promoter into the vector. Promoters can be inducible or constitutive, environmentally- or developmentally-regulated, or cell- or tissue-specific. Transcription is enhanced with promoters known in the art for expression. The CMV and SV40 promoters are commonly used to express desired peptide in cells. Other promoters known in the art may also be used (many suitable promoters and vectors are described in the applications and patents referenced in this application).

If one were to downregulate the expression of the nucleic acid molecule, one could insert the antisense sequence and the appropriate promoter into the vehicle. The nucleic acid molecule may be either isolated from a native source (in sense or antisense orientations), synthesized, or it may be a mutated native or synthetic sequence or a combination of these.

Examples of regulatory elements include a transcriptional promoter and enhancer or RNA polymerase binding sequence, a ribosomal binding sequence, including a translation initiation signal. Additionally, depending on the vector employed, other genetic elements, such as selectable markers, may be incorporated into the recombinant molecule.

Other regulatory regions that may be used include an enhancer domain and a termination region. The regulatory elements may be bacterial, fungal, viral or avian in origin. Likewise the regulatory elements may originate from animal, plant, yeast, insect or other sources, including synthetically produced elements and mutated elements.

In addition to using the expression vectors described above, the peptide may be expressed by inserting a recombinant nucleic acid molecule in a known expression system derived from bacteria, viruses, yeast, mammals, insects, fungi or birds. The recombinant molecule may be introduced into the cells by techniques such as Agrobacterium tumefaciens-mediated transformation, particle-bombardment-mediated transformation, direct uptake, microinjection, coprecipitation, transfection and electroporation depending on the cell type. Retroviral vectors, adenoviral vectors, Adeno Associated Virus (AAV) vectors, DNA virus vectors and liposomes may be used. Suitable constructs are inserted in an expression vector, which may also include markers for selection of transformed cells. The construct may be inserted at a site created by restriction enzymes.

In one embodiment of the invention, a cell is transfected with a nucleic acid molecule of the invention inserted in an expression vector to produce cells expressing a peptide encoded by the nucleic acid molecule.

Another embodiment of the invention relates to a method of transfecting a cell with a nucleic acid molecule disclosed herein, inserted in an expression vector to produce a cell expressing the CSP peptide [SEQ ID NO:11] or other peptide of the invention. In accordance with certain embodiments of the invention a method is provided for expressing the disclosed peptides in a cell. A preferred process would include culturing a cell including a recombinant DNA vector including a nucleic acid molecule encoding CSP [SEQ ID NO:5] (or another nucleic acid molecule of the invention) in a culture medium so that the peptide is expressed. The process preferably further includes recovering the peptide from the cells or culture medium.

Probes

Certain embodiments of the present invention include oligonucleotide probes made from the cloned CSP nucleic acid molecules described in this application or other nucleic acid molecules disclosed herein (see Materials and Methods section). The probes may be 15 to 20 nucleotides in length. A preferred probe is at least 15 nucleotides of SEQ ID NO:5. Certain embodiments of the invention also include at least 15 consecutive nucleotides of SEQ ID NO:5. The probes are useful to identify nucleic acids encoding CSP peptides as well as peptides functionally equivalent to CSP. The oligonucleotide probes are capable of hybridizing to the sequence shown in SEQ ID NO:5 under stringent hybridization conditions. A nucleic acid molecule encoding a peptide disclosed herein may be isolated from other organisms by screening a library under moderate to high stringency hybridization conditions with a labeled probe. The activity of the peptide encoded by the nucleic acid molecule is assessed by cloning and expression of the DNA. After the expression product is isolated, the peptide is assayed for CSP activity as described in this application.

Functionally equivalent CSP nucleic acid molecules from other cells, or equivalent CSP-encoding cDNAs or synthetic DNAs, can also be isolated by amplification using Polymerase Chain Reaction (PCR) methods. Oligonucleotide primers, such as degenerate primers, based on SEQ ID NO:5 can be prepared and used with PCR and reverse transcriptase (E. S. Kawasaki (1990), In Innis et al., Eds., PCR Protocols, Academic Press, San Diego, Chapter 3, p. 21) to amplify functional equivalent DNAs from genomic or cDNA libraries of other organisms. The oligonucleotides can also be used as probes to screen cDNA libraries.

Functionally Equivalent Peptides, Peptides and Proteins

The present invention includes not only the peptides encoded by the sequences disclosed herein, but also functionally equivalent peptides, peptides and proteins that exhibit the same or similar CSP peptide activity.

We designed and synthesized peptide analogs based on the native sequence of the *S. mutans* CSP and assayed their ability to interfere with competence development, acid tolerance response, and biofilm formation.

Peptide Analogs were Altered Based on the Amino Acid Sequence of Native CSP.

A panel of 17 peptide analogs with modification in length and hydrophobicity were designed and synthesized. The first set of peptide analogs were generated by deleting the $1^{st}$, 2nd, $3^{rd}$, $4^{th}$, or $5^{th}$ residues from the N- and C-termini of the mature CSP sequence. The second set included peptide analogs with substitutions of charged internal residues with neutral (valine) or hydrophobic (alanine) residues. The peptide analogs synthesized and tested in this study are listed at Table 1.

Peptide Analog H1 is Capable of Inhibiting Genetic Competence.

All 17 peptide analogs designed and synthesized based on the sequence of the native *S. mutans* CSP were first screened for their ability to hinder transformation efficiency in the *S. mutans* wild-type UA159 strain. Among them, analog H1 caused a significant decrease (18-fold) in transformation efficiency compared to that of the natural transformation (without addition of exogenous CSP) of the *S. mutans* UA159 strain (Table 2 and FIG. 2). These results demonstrate that H1 inhibited the *S. mutans* natural genetic transformation. The competence regulon identified and characterized by our laboratory indicated that transformation in *S. mutans* is a comD-dependent process. To test the hypothesis that the peptide analog H1 is able to compete with the natural CSP produced by *S. mutans* for occupying the ComD histidine kinase receptor, we tested the ability of H1 to induce genetic competence in an *S. mutans* comD null mutant. As expected, the results showed that the effect of peptide analog H1 is indeed accomplished via the ComD receptor, and therefore is a ComD-dependent process (FIG. 3).

In contrast, the peptide analogs IH-1, IH-2, B1, and C1 showed no significant effect on transformation efficiency compared to the wild-type CSP (Table 2). These results suggested that these peptide analogs have retained the native CSP activity despite the sequence modifications. However, the transformation efficiency of *S. mutans* UA159 in the presence of the peptide analogs D1, E1, F1, G1, A2, B2, C2, D2, E2, F2, G2, or B3 is diminished compared to the wild-type CSP (5 μg CSP). This suggested that these peptide analogs behave similarly to CSP in terms of competence stimulation but may not have the same affinity for the comD receptor as the native wild-type CSP.

TABLE 1

Modified versions of the mature *S. mutans* CSP peptide

| Peptide analog | Amino acid sequence | Modification |
|---|---|---|
| CSP | SGSLSTFFRLFNRSFTQALGK [SEQ ID NO:11] | mature wild-type CSP sequence |
| IH-1 | ~~S~~GSLSTFFRLFNRSFTQALGK [SEQ ID NO:35] | 1st residue removed from N' |
| IH-2 | SGSLSTFFRLFNRSFTQALG~~K~~ [SEQ ID NO:36] | 1st residue removed from C' |
| B1 | S~~G~~SLSTFFRLFNRSFTQALGK [SEQ ID NO:37] | 2nd residue removed from N' |
| C1 | SG~~S~~LSTFFRLFNRSFTQALGK [SEQ ID NO:38] | 3rd residue removed from N' |
| D1 | SGS~~L~~STFFRLFNRSFTQALGK [SEQ ID NO:39] | 4th residue removed from N' |
| E1 | SGSL~~S~~TFFRLFNRSFTQALGK [SEQ ID NO:40] | 5th residue removed from N' |
| F1 | SGSLSTFFRLFNRSFTQAL~~G~~K [SEQ ID NO:41] | 2nd residue removed from C' |
| G1 | SGSLSTFFRLFNRSFTQA~~L~~GK [SEQ ID NO:42] | 3rd residue removed from C' |
| H1 | SGSLSTFFRLFNRSFTQ~~A~~LGK [SEQ ID NO:43] | 4th residue removed from C' |
| A2 | SGSLSTFFRLFNRSFT~~Q~~ALGK [SEQ ID NO:44] | 5th residue removed from C' |
| B2 | SGSLSTFFVLFNRSFTQALGK [SEQ ID NO:45] | Substitution of 1st R residue with V |
| C2 | SGSLSTFFALFNRSFTQALGK [SEQ ID NO:46] | Substitution of 1st R residue with A |
| D2 | SGSLSTFFRLFNVSFTQALGK [SEQ ID NO:47] | Substitution of 2nd R residue with V |
| E2 | SGSLSTFFRLFNASFTQALGK [SEQ ID NO:48] | Substitution of 2nd R residue with A |
| F2 | SGSLSTFFRLFNRSFTQALGV [SEQ ID NO:49] | Substitution of K residue with V |
| G2 | SGSLSTFFRLFNRSFTQALGA [SEQ ID NO:50] | Substitution of K residue with A |
| B3 | SGTLSTFFRLFNRSFTQA~~LGK~~ [SEQ ID NO:51] | JH1005 CSP sequence |

TABLE 2

Effect of 5 μg/ml of peptide analogs on competence of *S. mutans* wild-type UA159

| Peptide analog | Transformation efficiency (vs no CSP) | Transformation efficiency (vs 5 μg CSP) |
| --- | --- | --- |
| CSP | 1554-fold increase | — |
| IH-1 | no effect[a] | no effect |
| IH-2 | no effect | no effect |
| B1 | no effect | no effect |
| C1 | no effect | no effect |
| D1 | 275-fold increase | 6-fold decrease |
| E1 | 791-fold increase | 2-fold decrease |
| F1 | 541-fold increase | 3-fold decrease |
| G1 | 848-fold increase | 2-fold decrease |
| H1 | 18-fold decrease | 28,000-fold decrease |
| A2 | 125-fold increase | 7-fold decrease |
| B2 | 4-fold increase | 414-fold decrease |
| C2 | 32-fold increase | 48-fold decrease |
| D2 | 99-fold increase | 16-fold decrease |
| E2 | 252-fold increase | 6-fold decrease |
| F2 | 543-fold increase | 3-fold decrease |
| G2 | 56-fold increase | 28-fold decrease |
| B3 | 195-fold increase | 8-fold decrease |

[a]No effect: no significant difference by comparison with CSP.

TABLE 3

Effect of 5 μg/ml of peptide analogs on growth at pH 7.5, acid resistance, and biofilm formation of *S. mutans* wild-type UA159

| Peptide analog | Growth (pH 7.5) | Acid resistance (pH 5.5) | Biofilm formation (SDM-glucose) |
| --- | --- | --- | --- |
| CSP | ↓ growth | growth | no effect |
| IH-1 | ↓ growth | growth | no effect |
| IH-2 | ↓ growth | growth | no effect |
| B1 | ↓ growth | growth | no effect |
| C1 | ↓ growth | growth | no effect |
| D1 | ↓ growth | growth | no effect |
| E1 | ↓ growth | growth | no effect |
| F1 | ↓ growth | ↓ growth | ↓ 36.7% biomass |
| G1 | ↓ growth | growth | ↓ 24.4% biomass |
| H1 | no effect | ↓ growth | no effect |
| A2 | no effect | ↓ growth | no effect |
| B2 | no effect | ↓ growth | no effect |
| C2 | no effect | ↓ growth | no effect |
| D2 | no effect | ↓ growth | no effect |
| E2 | no effect | ↓ growth | ↓ 38.9% biomass |
| F2 | ↓ growth | ↓ growth | ↓ 38.7% biomass |
| G2 | ↓ growth | ↓ growth | ↓ 35.6% biomass |
| B3 | no effect | ↓ growth | ↓ 34.4% biomass |

Multiple Peptide Analogs Affect Cell Growth in an Acidic Medium.

In order to determine if the peptide analogs were capable of inhibiting the acid tolerance mechanisms of *S. mutans*, the cells' ability to withstand acid challenge typically encountered in dental plaque, the *S. mutans* UA159 cells were grown in THYE medium at pH 7.5 and pH 5.5 in the presence of various concentrations of peptide analogs. The results presented at Table 3 showed that the peptide analogs F1, F2, and G2 caused a diminution of cell growth at pH 7.5 and 5.5. The peptide analogs H1, A2, B2, C2, D2, E2, and B3 have no effect on *S. mutans* cell growth at pH 7.5. Moreover, when the same peptide analogs were tested at pH 5.5, the results showed that there was a significant decrease in cell growth. Interestingly, the peptide analog H1 involved in the inhibition of genetic competence is also able to inhibit the *S. mutans* cell growth in an acidic medium (FIG. 4), while the growth at neutral pH is unaffected (FIG. 5).

Peptide Analogs Inhibit of *S. mutans* Biofilm Formation.

It has been demonstrated that the *S. mutans* comC null mutant unable to produce the CSP signal peptide forms a biofilm lacking the wild-type architecture. Moreover, the exogenous addition of synthetic CSP restores the wild-type phenotype in the comC defective mutant (Li et al., 2002). Therefore, CSP seems to play an integral part in *S. mutans* biofilm formation. Consequently, the peptide analogs were tested for their ability to inhibit the formation of *S. mutans* biofilms. Results presented at Table 3 indicated that the peptide analogs F1, G1, E2, F2, G2 and B3 had a significantly reduced biomass ranging from 24.4% to 38.9% compared to the *S. mutans* biofilm grown in the presence of wild-type CSP suggesting that these peptide analogs are able to hinder the signal pathway regulating the formation of biofilm by *S. mutans*. Peptide analog E2 could be a potent *S. mutans* QS inhibitor as it elicited a significant decrease in biofilm formation as well as inhibited cell growth at pH 5.5 without affecting the cell growth at neutral pH.

A peptide is considered to possess a function substantially equivalent to that of the CSP peptide [SEQ ID NO:11] if it has CSP activity. CSP activity means that it is able to confer genetic competence to *S. mutans*, as measured by an increased ability to incorporate and express foreign genetic material, when added to cells as described in the assay of genetic competence below. CSP activity also means that the peptide is able to confer an acid tolerance response in *S. mutans* as measured by an increase in cell survival under acidic pH conditions when added to cells as described in the assay for acid adaptation below. Functionally equivalent peptides, peptides and proteins include peptides, peptides and proteins that have the same or similar protein activity as CSP when assayed, i.e. they are able to stimulate genetic competence and low pH tolerance (the ability to withstand acid challenges of pH 3.5-pH 3.0 for up to 3 hours) in *S. mutans*. A peptide has CSP activity if it is capable of increasing the frequency of uptake and expression of foreign DNA as described in the following assay for genetic competence and if the peptide can promote an acid tolerance response as described in the assay for acid adaptation.

Identity refers to the similarity of two peptides or proteins that are aligned so that the highest order match is obtained. Identity is calculated according to methods known in the art, such as the ClustalW program. For example, if a peptide (called "Sequence A") has 90% identity to a portion of the peptide in SEQ ID NO:3, then Sequence A will be identical to the referenced portion of the peptide in SEQ ID NO:3, except that Sequence A may include up to 1 point mutations, such as substitutions with other amino acids, per each 10 amino acids of the referenced portion of the peptide in SEQ ID NO:3. Peptides, peptides and proteins functional equivalent to the CSP peptides can occur in a variety of forms as described below.

Peptides biologically equivalent in function to CSP peptide include amino acid sequences containing amino acid changes in the CSP sequence [SEQ ID NO:11]. The functional equivalent peptides have at least about 40% sequence identity, preferably at least about 60%, at least about 75%, at least about 80%, at least about 90% or at least about 95% sequence identity, to the natural CSP peptide [SEQ ID NO:11] or a corresponding region. The ClustalW program preferably determines sequence identity. Most preferably, 1, 2, 3, 4, 5, 5-10, 10-15 amino acids are modified.

Variants of the CSP peptide may also be created by splicing. A combination of techniques known in the art may be used to substitute, delete or add amino acids. For example, a hydrophobic residue such as methionine can be substituted for another hydrophobic residue such as alanine. An alanine residue may be substituted with a more hydrophobic residue such as leucine, valine or isoleucine. An aromatic residue such as phenylalanine may be substituted for tyrosine. An acidic, negatively-charged amino acid such as aspartic acid may be substituted for glutamic acid. A positively-charged amino acid such as lysine may be substituted for another positively-charged amino acid such as arginine. Modifications of the peptides disclosed herein may also be made by treating such peptide with an agent that chemically alters a side group, for example, by converting a hydrogen group to another group such as a hydroxy or amino group.

Peptides having one or more D-amino acids are contemplated in certain embodiments of the present invention. Also contemplated are peptides where one or more amino acids are acetylated at the N-terminus. Those skilled in the art recognize that a variety of techniques are available for constructing peptide mimetics (i.e., a modified peptide or peptide or protein) with the same or similar desired biological activity as the corresponding disclosed peptide but with more favorable activity than the peptide with respect to characteristics such as solubility, stability, and/or susceptibility to hydrolysis and proteolysis. See for example, Morgan and Gainor, *Ann. Rep. Med. Chem.*, 24:243-252(1989).

Certain embodiments of the invention also include hybrid nucleic acid molecules and peptides, for example where a nucleic acid molecule from the nucleic acid molecule disclosed herein is combined with another nucleic acid molecule to produce a nucleic acid molecule which expresses a fusion peptide. One or more of the other domains of CSP described in this application could also be used to make fusion peptides. For example, a nucleotide domain from a molecule of interest may be ligated to all or part of a nucleic acid molecule encoding CSP peptide (or a molecule having sequence identity) described in this application. Fusion nucleic acid molecules and peptides can also be chemically synthesized or produced using other known techniques. Certain embodiments of the invention include a nucleic acid molecule encoding a fusion peptide or a recombinant vector including the nucleic acid molecule.

The variants preferably retain the same or similar CSP activity as the naturally occurring CSP [SEQ ID NO:11]. The CSP activity of such variants can be assayed by techniques described in this application and known in the art.

Variants produced by combinations of the techniques described above but which retain the same or similar CSP activity as naturally occurring CSP [SEQ ID NO:11] are also included in certain embodiments of the invention (for example, combinations of amino acid additions, and substitutions).

Variants of CSP produced by techniques described above which competitively inhibit CSP activity are also included in certain embodiments of the invention (for example, combinations of amino acid additions, and substitutions).

Variants of CSP produced by techniques described above which decrease transformation efficiency of bacteria are also included in the invention (for example, combinations of amino acid additions, and substitutions).

Variants of CSP produced by techniques described above which decrease biofilm formation are also included in certain embodiments of the invention (for example, combinations of amino acid additions, and substitutions).

Variants of CSP encompassed by the present invention preferably have at least about 40% sequence identity, preferably at least about 60%, 75%, 80%, 90% or 95% sequence identity, to the naturally occurring peptide, or corresponding region or moiety of the peptide, or corresponding region. Sequence identity is preferably measured with the ClustalW.

Histidine Kinase & Response Regulator

Certain embodiments of the invention also include sequences having identity with the histidine kinase, response regulator of the invention and comA and comB. Preferred percentages of identity (nucleic acid molecule and polypeptide) are the same as those described for the CSP.

As well, probes and antibodies for a histidine kinase [SEQ ID NO:2 and SEQ ID NO:6], response regulator [SEQ ID NO:3 and SEQ ID NO:7] comA [SEQ ID NO:31 and SEQ ID NO:32] or comB [SEQ ID NO:33 and SEQ ID NO:34] may be prepared using the description in this application and techniques known in the art. The description for preparation of CSP variants and mutants is also applicable to the histidine kinase [SEQ ID NO:2 and SEQ ID NO:6], response regulator [SEQ ID NO:3 and SEQ ID NO:7] or comA [SEQ ID NO:31 and SEQ ID NO:32] and comB [SEQ ID NO:33 and SEQ ID NO:34] of the invention. Certain embodiments of the invention also include fragments of HK having HK activity, fragments of RR [SEQ ID NO:3 and SEQ ID NO:7] having RR activity and fragments of comA [SEQ ID NO:31 and SEQ ID NO:32] or comB [SEQ ID NO:33 and SEQ ID NO:34] having activity.

Design of CSP Peptide Competitive Inhibitors

The activity of the CSP peptide [SEQ ID NO:11] may be varied by carrying out selective site-directed mutagenesis. We characterize the binding domain and other critical amino acid residues in the peptide that are candidates for mutation, insertion and/or deletion. Sequence variants may be synthesized. A DNA plasmid or expression vector containing the CSP nucleic acid molecule [SEQ ID NO:5] or a nucleic acid molecule having sequence identity may be used for these studies using the U.S.E. (Unique site elimination) mutagenesis kit from Pharmacia Biotech or other mutagenesis kits that are commercially available, or using PCR. Once the mutation is created and confirmed by DNA sequence analysis, the mutant peptide is expressed using an expression system and its activity is monitored. This approach is useful to identify CSP inhibitors. All these modifications of the CSP DNA sequences presented in this application and the peptides produced by the modified sequences are encompassed by the present invention.

Pharmaceutical Compositions

The CSP inhibitors are also useful when combined with a carrier in a pharmaceutical composition. The compositions are useful when administered in methods of medical treatment or prophylaxis of a disease, disorder or abnormal physical state caused by *S. mutans*. Certain embodiments of the invention also include methods of medical treatment of a disease, disorder or abnormal physical state characterized by excessive *S. mutans* or levels or activity of CSP peptide [SEQ ID NO:11], for example by administering a pharmaceutical composition including a carrier and a CSP inhibitor. Caries is one example of a disease, which can be treated or prevented by antagonizing CSP [SEQ ID NO:11].

The pharmaceutical compositions can be administered to humans or animals by methods such as food, food additives, gel, toothpaste, mouthwash, dental floss or chewing gum in methods of medical treatment. The peptides of the invention may be coupled to lipids or carbohydrates. This increases their ability to adhere to teeth, either by prolonging the duration of the adhesion or by increasing its affinity, or both. They may also be coupled to polymers, for example in dental work (eg. crowns, braces, fillings) or dental floss. The pharmaceutical compositions can be administered to humans or animals. Dosages to be administered depend on individual patient condition, indication of the drug, physical and chemical stability of the drug, toxicity of the desired effect and the chosen route of administration (Robert Rakel, ed., Conn's Current Therapy (1995, W.B. Saunders Company, USA)). The pharmaceutical compositions are used to treat diseases caused by streptococcal infections such as caries and endocarditis.

CSP activity could be blocked by antisense mRNA or by inhibiting the activity of the exporter that secretes it from the cell. We have the sequence of these exporters. There are two copies of the genes (comAB) [SEQ ID NO:31 and SEQ ID NO:33] that are involved in export.

Nucleic acid molecules (antisense inhibitors of CSP) and competitive inhibitors of CSP may be introduced into cells using in vivo delivery vehicles such as liposomes. They may also be introduced into these cells using physical techniques such as microinjection and electroporation or chemical methods such as coprecipitation or using liposomes.

The pharmaceutical compositions can be prepared by known methods for the preparation of pharmaceutically acceptable compositions which can be administered to patients, and such that an effective quantity of the nucleic acid molecule or peptide is combined in a mixture with a pharmaceutically acceptable vehicle. Suitable carriers are described, for example in Remington's Pharmaceutical Sciences (Remington's Pharmaceutical Sciences, Mack Publishing Company, Easton, Pa., USA). Carriers include saline and D5W (5% dextrose and water). Excipients include additives such as a buffer, solubilizer, suspending agent, emulsifying agent, viscosity controlling agent, flavor, lactose filler, antioxidant, preservative or dye. There are preferred excipients for stabilizing peptides for parenteral and other administration. The excipients include serum albumin, glutamic or aspartic acid, phospholipids and fatty acids.

On this basis, the pharmaceutical compositions could include an active compound or substance, such as a CSP inhibitor, in association with one or more pharmaceutically acceptable vehicles or diluents, and contained in buffered solutions with a suitable pH and isoosmotic with the physiological fluids. The methods of combining the active molecules with the vehicles or combining them with diluents is well known to those skilled in the art. The compositions may also contain additives such as antioxidants, buffers, bacteriostatis, bactericidal antibiotics and solutes which render the formulation isotonic in the intended recipient; and aqueous and non-aqueous sterile suspensions which may include suspending agents and thickening agents. The composition could include a targeting agent for the transport of the active compound to specified sites.

According to another aspect of the present invention, there is provided a process of producing cells genetically modified to produce a CSP derivative which inhibits transformation efficiency. Another aspect comprises administering to a patient S. mutans genetically modified to produce a CSP derivative which inhibits transformation efficiency. Methods of producing and administering genetically engineered cells are known in the art, see, for example, WO02/44230.

A further aspect of the present invention provides the use in the preparation of a medicament for administration to a mammalian patient to alleviate dental caries, of viable, transfected S. mutans genetically modified to produce a CSP derivative which inhibits transformation efficiency.

According to another aspect of the present invention, there is provided a process of producing cells genetically modified to produce a CSP derivative which inhibits biofilm formation.

Another aspect comprises administering to a patient cells genetically modified to produce a CSP derivative which inhibits biofilm formation.

A further aspect of the present invention provides the use in the preparation of a medicament for administration to a mammalian patient to improve oral health or to alleviate dental caries, of viable, transfected cells genetically modified to produce a CSP derivative which inhibits biofilm formation.

Vaccines

Antibodies directed against CSP [SEQ ID NO:11] would provide protection against caries. Antibodies may be manufactured as described below. Alternatively, a disclosed peptide [SEQ ID NO:11] or a fragment thereof may be used with a carrier to make a vaccine. The peptide or fragment may also be conjugated to another molecule to increase its antigenicity. Antibodies can also be coupled to the peptide (Brady, L J. et al., "Monoclonal Antibody-Mediated Modulation of the Humoral Immune Response against Mucosally Applied Streptococcus mutans" (in press). In order to enhance the immune response the peptide can be coupled to KLH, ovalbumin, or thyroglobulin prior to immunization. The vaccine composition will trigger the mammal's immune system to produce antibodies. Certain embodiments of the invention include vaccine compositions and methods of vaccinating a mammal, preferably a human, against dental caries by administering to the mammal an effective amount of a vaccine composition. Techniques for preparing and using vaccines are known in the art. To prepare the vaccine, the peptide, or a fragment of the peptide, may be mixed with other antigens (of different immunogenicity), a vehicle or an excipient. Examples of peptide vaccines are found in U.S. Pat. Nos. 5,679,352, 5,194,254 and 4,950,480. Techniques for preparing vaccines involving site-directed mutagenesis are described in U.S. Pat. Nos. 5,714,372, 5,543,302, 5,433,945, 5,358,868, 5,332,583, 5,244,657, 5,221,618, 5,147,643, 5,085,862 and 5,073,494. Vaccines may be administered by known techniques, such as topical or parenteral administration. Vast changes are taking place in vaccinology consequent to the introduction of new technologies. A cellular purified fractions devoid of side effects, non-pathogenic but immunogenic mutants, recombinant technology, conjugated vaccines, combination vaccines (to limit the number of injections). Vaccine delivery systems can deliver multiple doses of the vaccine at a single contact point. A genetically engineered oral vaccine is useful to impart better and longer duration of immunity. Oral vaccines are useful. The nose as a route for immunization is also useful. DNA alone can constitute the vaccines, inducing both humoral and cell-mediated immune responses. Live recombinant vaccines are also useful. Potent adjuvants add to the efficacy of the vaccines. One can also 'humanize' mouse monoclonals by genetic engineering and express these efficiently in plants. These recombinant antibodies are opening out an era of highly specific and safe therapeutic interventions. An advantage of preformed antibodies directed at a defined target and given in adequate amounts is the certainty of efficacy in every recipient, in contrast to vaccines, where the quality and quantum of immune response varies from individual to individual. For example, nasal immunization may be done as described in C. Jespersgaard et al. "Protective Immunity against Streptococcus mutans Infection in Mice after Intranasal Immunization with the Glucan-Binding Region of S. mutans Glucosyltransferase" Infection and Immunity, December 1999, p. 6543-6549, Vol. 67, No. 12. Vaccine compositions may comprise solid or liquid formulations such as gels, sprays, inhalants, tablets, toothpastes, mouthwashes or chewing gum.

For vaccine application, cholera toxin can be used by coupling the peptide to its B-subunit to stimulate production of secretory antibody i.e., Coupling to CTB. Screening for inhibitors of CSP.

Inhibitors are preferably directed towards CSP [SEQ ID NO:11] to block S. mutans competence, low pH tolerance and biofilm formation.

A method of identifying a compound which reduces the interaction of CSP [SEQ ID NO:11] with HK [SEQ ID NO:2], can include: contacting (i) CSP [SEQ ID NO:11] with (ii) HK [SEQ ID NO:2], a CSP-binding fragment of HK or a derivative of either of the foregoing in the presence of the compound; and b) determining whether the interaction between (i) and (ii) is reduced, thereby indicating that the compound reduces the interaction of CSP [SEQ ID NO:11] and HK [SEQ ID NO:2]. A CSP inhibitor (caries treating or preventing compound) inhibits the interaction between (i) and (ii). By way of example, one can screen a synthetic peptide library. One could also screen small non-peptide organic molecules.

In one embodiment, the invention includes an assay for evaluating whether test compounds are capable of acting as agonists or antagonists for CSP, or a peptide having CSP functional activity, including culturing cells containing DNA which expresses CSP [SEQ ID NO:5], or a peptide having CSP activity so that the culturing is carried out in the presence of at least one compound whose ability to modulate CSP activity is sought to be determined and thereafter monitoring the cells for either an increase or decrease in the level of CSP [SEQ ID NO:11] or CSP activity. Other assays (as well as variations of the above assay) will be apparent from the description of this invention and techniques such as those disclosed in U.S. Pat. Nos. 5,851,788, 5,736,337 and 5,767,075 which are incorporated by reference in their entirety. For example, the test compound levels may be either fixed or variable.

Preparation of Antibodies

The CSP peptide [SEQ ID NO:11] is also useful as an antigen for the preparation of antibodies that can be used to purify or detect other CSP-like peptides. Antibodies may also block CSP [SEQ ID NO:11] binding to HK [SEQ ID NO:2]. Antibodies are preferably targeted to the entire CSP [SEQ ID NO:11] sequence. The CSP peptide [SEQ ID NO:11] may be conjugated to other compounds, in order to increase immunogenicity.

We generate polyclonal antibodies against CSP [SEQ ID NO:11], which is a unique sequence. Monoclonal and polyclonal antibodies are prepared according to the description in this application and techniques known in the art. For examples of methods of preparation and uses of monoclonal antibodies, see U.S. Pat. Nos. 5,688,681, 5,688,657, 5,683,693, 5,667,781, 5,665,356, 5,591,628, 5,510,241, 5,503,987, 5,501,988, 5,500,345 and 5,496,705, which are incorporated by reference in their entirety. Examples of the preparation and uses of polyclonal antibodies are disclosed in U.S. Pat. Nos. 5,512,282, 4,828,985, 5,225,331 and 5,124,147 which are incorporated by reference in their entirety. Antibodies recognizing CSP can be employed to screen organisms or tissues containing CSP peptide [SEQ ID NO:11] or CSP-like peptides. The antibodies are also valuable for immuno-purification of CSP or CSP-like peptides from crude extracts.

An antibody (preferably the antibody described above) may be used to detect CSP [SEQ ID NO:11] or a similar peptide, for example, by contacting a biological sample with the antibody under conditions allowing the formation of an immunological complex between the antibody and a peptide recognized by the antibody and detecting the presence or absence of the immunological complex whereby the presence of CSP [SEQ ID NO:11] or a similar peptide is detected in the sample. Certain embodiments of the invention also include compositions preferably including the antibody, a medium suitable for the formation of an immunological complex between the antibody and a peptide recognized by the antibody and a reagent capable of detecting the immunological complex to ascertain the presence of CSP [SEQ ID NO:11] or a similar peptide. Certain embodiments of the invention also include a kit for the in vitro detection of the presence or absence of CSP [SEQ ID NO:11] or a similar peptide in a biological sample, wherein the kit preferably includes an antibody, a medium suitable for the formation of an immunological complex between the antibody and a peptide recognized by the antibody and a reagent capable of detecting the immunological complex to ascertain the presence of CSP [SEQ ID NO:11] or a similar peptide in a biological sample. Further background on the use of antibodies is provided, for example in U.S. Pat. Nos. 5,695,931 and 5,837,472, which are incorporated by reference in their entirety.

Assay of Genetic Competence

The ability of the peptide to activate the HK [SEQ ID NO:2] and RR [SEQ ID NO:3] and the subsequent genes involved in the conferral of the properties of genetic competence, acid tolerance and biofilm formation can be determined by measuring the efficiency of uptake and expression of DNA (preferably plasmid DNA) in S. mutans when exposed to signal peptide and/or inhibitor. Two methods modified based on the protocols described by Perry et al. Infect Immun, 41:722-727 and Lindler and Macrina J Bacteriol, 166:658-665 are used to assay genetic competence. The method involves adding DNA and CSP DNA [SEQ ID NO:5] (preferably plasmid DNA) to a S. mutans culture (or culture of a bacteria expressing CSP [SEQ ID NO:11] or a variant thereof). The rate of transformation is then determined. S. mutans is preferably grown in THYE plus 5% horse serum (THYE-HS). After 2-hr incubation, 1 µg/ml plasmid DNA or 10 µg/ml of chromosomal DNA is added to the culture. To assay induction of competence, competence signal peptide, (SCSP) [SEQ ID NO:11] is then added to the cultures, incubation continued for 30 minutes with a final concentration of 500 ng/ml of SCSP added to each sample. After the 30-minute incubation equal amounts of DNA is added to each well (1 µg/ml plasmid or 10 µg/ml of chromosomal DNA) and incubation continued for another 2 hrs. Cell dilutions were immediately spread on THYE agar plates plus appropriate antibiotics. Transformation frequency was expressed as the number of transformants (antibiotic resistant cells) per number of viable recipients. This is determined by comparing the number of cells able to grow in the presence of antibiotic (conferred by the applied plasmid or chromosomal DNA) relative to the total number of cells present (i.e., that grow in the absence of antibiotic). A higher value indicates a higher rate of transformation and thus is reflective of a stimulatory effect by the peptide. Consequently, addition of a molecule that successfully acts as an inhibitor results in a lower ratio of transformants/recipients, indicating that the inhibitor is effective at blocking activity of the CSP [SEQ ID NO:11]. CSP deficient cells may also be used in a variation of these assays. One can identify compounds that inhibit CSP or variants thereof by adding a test compound to the mixture to determine if the rate of transformation is decreased by the addition of the test compound.

The activity of the system can also be measured by an in vitro assay that relies on the measurement of marker protein expression (such as green fluorescent protein (GFP)) via expression from a fusion to a promoter controlled by the signal cascade initiated by CSP [SEQ ID NO:11]/HK [SEQ ID NO:2]/RR [SEQ ID NO:3]. One such promoter occurs immediately 5' proximal to the *S. mutans* comX gene. *S. mutans* cells grown in microtiter wells are exposed to the CSP [SEQ ID NO:11] and/or inhibitor and the level of fluorescence of the comX::GFP strain is measured to give a quantitative measure of CSP [SEQ ID NO:11] stimulation (and conversely inhibitor activity). One can identify compounds that inhibit CSP [SEQ ID NO:11] or variants thereof by adding a test compound to the mixture to determine if the quantitative, measure of CSP [SEQ ID NO:11] stimulation is decreased by the addition of the test compound.

Assay of Acid Resistance Tolerance

The ability of CSP [SEQ ID NO:11] to promote acid resistance tolerance is determined by measuring the cell survival rate of *S. mutans* when exposed to acidic pH. In one example, *S. mutans* are first grown in batch culture to assay acid tolerance response in 'standard' log- and stationary-phase cells by using a modification of methods described previously by Svensater et al. Oral Microbiol. Immunol., 12:266-73. Mid-log-phase cells are obtained by transferring one volume of overnight culture into nine volumes (1:10) of fresh TYG medium (pH 7.5) and incubated at 37° C. with 5% $CO_2$ for 2 hours. These cells are then collected by centrifugation at 8,000×g for 10 min and resuspended in 2 ml of fresh TYG (pH 5.5) at various cell densities as determined by $O.D_{600}$. The cells are induced for acid adaptation by incubation at pH 5.5 for 2 h at 37° C. with 5% $CO_2$. The adapted log-phase cells are then exposed to the killing pH. Killing pH is pre-determined by incubating unadapted, mid-log phase cells in TYG medium at pH values from 6.0 to 2.0. Stationary-phase cells are prepared by re-suspending late-log phase cells in TY medium (tryptone-yeast extract) without glucose. The culture is incubated at 37° C. for 2 h to allow the cells to fully enter into stationary phase. Induction of acid adaptation in stationary-phase cells follows a similar procedure to that for log-phase cells. Adaptation of both log- and stationary-phase cells to acidic pH is determined by measuring the ability of bacterial cells to survive a killing pH for 3 h. Acid killing is initiated by resuspending cells in the same volume of fresh TYG (pH 3.5) and an aliquot of cell suspension is taken immediately from each sample to determine total viable cell number at zero time. The cells are then incubated for 3 h at 37° C. with 5% $CO_2$ and an aliquot of sample is taken to determine survival rate by viable cell counts. Addition of a molecule that successfully acts as an inhibitor results in a decrease in the acid resistance tolerance of *S mutans* resulting in a corresponding decrease in cell survival indicating that the inhibitor is effective at blocking activity of CSP. CSP deficient cells may also be used in a variation of these assays wherein addition of the signal peptide can complement the acid-adaptation-defective phenotype of a comC deficient cell. One can identify compounds that inhibit CSP or variants thereof by adding a test compound to the mixture to determine if the survival rate of cells is decreased by the addition of the test compound.

Cells transformed with a nucleic acid molecule disclosed herein (histidine kinase [SEQ ID NO:6], CSP [SEQ ID NO:5] or response regulator [SEQ ID NO:7]) are useful as research tools. For example, one may obtain a cell (or a cell line, such as an immortalized cell culture or a primary cell culture) that does not express histidine kinase [SEQ ID NO:2], CSP [SEQ ID NO:11] or response regulator [SEQ ID NO:3], insert a histidine kinase [SEQ ID NO:6], CSP [SEQ ID NO:5] or response regulator [SEQ ID NO:7] nucleic acid molecule in the cell, and assess the level of expression and activity. Alternatively, histidine kinase [SEQ ID NO:6], CSP [SEQ ID NO:5] or response regulator [SEQ ID NO:7] nucleic acid molecules may be over-expressed in a cell that expresses a histidine kinase [SEQ ID NO:2], CSP [SEQ ID NO:11] or response regulator [SEQ ID NO:3] nucleic acid molecule. In another example, experimental groups of cells may be transformed with vectors containing different types of histidine kinase, CSP or response regulator nucleic acid molecules to assess the levels of polypeptides and peptides produced, its functionality and the phenotype of the cells. The polypeptides and peptides are also useful for in vitro analysis of histidine kinase, CSP [SEQ ID NO:11] or response regulator [SEQ ID NO:3] activity or structure. For example, the polypeptides and peptides produced can be used for microscopy or X-ray crystallography studies.

The histidine kinase [SEQ ID NO:2 and SEQ ID NO:6], CSP [SEQ ID NO:5 and SEQ ID NO:11] or response regulator [SEQ ID NO:3 and SEQ ID NO:7] nucleic acid molecules and polypeptides are also useful in assays for the identification and development of compounds to inhibit and/or enhance polypeptide or peptide function directly. For example, they are useful in an assay for evaluating whether test compounds are capable of acting as antagonists for histidine kinase [SEQ ID NO:2], CSP [SEQ ID NO:11] or response regulator [SEQ ID NO:3] by: (a) culturing cells containing a nucleic acid molecule which expresses histidine kinase [SEQ ID NO:2], CSP [SEQ ID NO:11] or response regulator peptides [SEQ ID NO:3] (or fragments or variants thereof having histidine kinase [SEQ ID NO:2], CSP or response regulator activity) wherein the culturing is carried out in the presence of increasing concentrations of at least one test compound whose ability to inhibit histidine kinase [SEQ ID NO:2], CSP [SEQ ID NO:11] or response regulator [SEQ ID NO:3] is sought to be determined; and (b) monitoring in the cells the level of inhibition as a function of the concentration of the test compound, thereby indicating the ability of the test compound to inhibit histidine kinase [SEQ ID NO:2], CSP [SEQ ID NO:11] or response regulator [SEQ ID NO:3] activity.

Suitable assays may be adapted from, for example, U.S. Pat. No. 5,851,788.

MATERIALS AND METHODS

Growth Conditions of Cells

Cells are grown in Todd Hewitt yeast extract medium at various dilutions with and without 5% horse serum and 0.01% hog gastric mucin.

Protocol for Transformation of Biofilm-Grown Cells

Biofilms are developed on polystyrene microtiter plates to provide a rapid and simple method for assaying biofilm formation, and hence activity of the peptide [SEQ ID NO:11]/receptor [SEQ ID NO3]/kinase [SEQ ID NO:2] system. Formation of biofilms is initiated by inoculating 20 µl of cell suspension into each well containing 2 ml of biofilm medium (4× diluted Todd-Hewitt Yeast Extract supplemented with final concentration of 0.01% hog gastric mucin) for overnight incubation at 37° C. under an anaerobic condition. After 20-h incubation, fluid medium is removed and added with 2 ml of pre-warmed, fresh THYE plus 5% horse serum. The cultures are incubated for 30 minutes and each well is supplemented with a final concentration of 200 ng/ml of synthetic competence stimulating peptide (SCSP) and varying concentrations of the inhibitor and the incubation is continued. After 30 minutes, plasmid DNA (1 mg/ml) or chromosomal DNA (10 mg/ml) is added to each well and the cultures are incubated for an additional 2 hr. Planktonic cells are then removed and the wells are washed once with PBS buffer. Biofilm cells are collected into 2 ml fresh medium by a gentle sonication or washing the wells using a pipette. The samples are centrifuged at 12,000×g for 5 min. Both biofilm and planktonic cells are resuspended into 200 µl of fresh medium and are immediately spread on THYE agar plus appropriate antibiotics. Transformation frequency is determined after 48-h of incubation.

Genome Database Analysis

Homologues of the *Streptococcus pneumoniae* comD/comE genes encoding a histidine kinase/response regulator system were identified. This sequence was used to design primers to amplify the region from a number of *S. mutans* isolates. An open reading frame consisting of 138 nucleotides was located 148 nucleotides 5' proximal from the end of the comD homolog in the opposite orientation (FIG. 1). This ORF was found to encode a peptide of 46-amino acid [SEQ ID NO:1] in length, the precursor of the 21-amino acid CSP [SEQ ID NO:11].

PCR Amplification and Nucleotide Sequencing

The comCDE genes [SEQ ID NO:18 and SEQ ID NO:19] were amplified from the genomes of several *S. mutans* isolates by PCR using primers designed based on the genome database sequence and their nucleotide sequences determined. The deduced amino acid sequences are compared among the isolates by sequence alignment to confirm identity.

Gene Inactivations

Genes are inactivated by integration of internal homologous fragments into the suicide vector pVA8912. Mutants defective in each of the individual genes (comC, comD, comE) are inactivated and their phenotypes are compared to the parent strain NG8 for their abilities to form biofilms, tolerate acidic pH (pH 2-4), and transport and incorporate DNA. The knockout mutants of comD and comE were constructed by insertion-duplication mutagenesis, whereas the knockout comC mutant was created by allelic exchange via insertion of an erythromycin resistance determinant into the comC locus (Li et al, 2001). All mutant strains were therefore resistant to erythromycin. The wild-type strain was subcultured routinely on Todd-Hewitt-Yeast Extract (THYE) agar plates (BBL®; Becton Dickinson, Cockeysville, Md.), whereas the mutants were maintained on THYE agar plus 10 µg/ml of erythromycin. A minimal medium (DMM) was prepared to grow biofilms by a modification of the method described previously (Loo et al, 2000). The medium contained 58 mM $K_2HPO_4$, 15 mM $KH_2PO_4$, 10 mM $(NH_4)_2SO_4$, 35 mM NaCl, 2 mM $MgSO_2$ $7H_2O$, 0.2% (wt/vol) Casamino Acids and was supplemented with filter-sterilized vitamins, (0.04 mM nicotinic acid, 0.1 mM pyridoxin HCl, 0.01 mM pantothenic acid, 1 µM riboflavin, 0.3 µM thiamin HCl, and 0.05 µM D-biotin), amino acids (4 mM L-glutamic acid, 1 mM L-arginine HCl, 1.3 mM L-cysteine HCl, and 0.1 mM L-tryptophan) and 20 mM glucose.

Creation of comD Deletion Mutant.

An *S. mutans* UA159 comD null mutant was constructed by a PCR-based deletion strategy involving restriction-ligation and allelic replacement as described previously (Lau et al., 2002). The primers used to construct and confirm the *S. mutans* comD deletion mutant are P1-HK13 (5'-CACAACAACTTATTGACGCTATCCC-3') [SEQ ID NO:52], P2-HK13 (5'-GGCGCGCCAACTGGCAACAGGCAGCAGACC-3') [SEQ ID NO:53], P3-HK13 (5'-GGCCGGCCT-CAAAACGATGCTGTCAAGGG-3') [SEQ ID NO:54], P4-HK13 (5'-AGATTATCATTGGCGGAAGCG-3') [SEQ ID NO:55], Erm-19 (5'-GGCGCGCCCCGGGC-CCAAAATTTGTTTGAT-3') [SEQ ID NO:56], and Erm-20 (5'-GGCCGGCCAGTCGGCAGCGACTCATAGAAT-3') [SEQ ID NO:57].

Synthesis of Synthetic Peptide

The sequence of the processed peptide was deduced by determining the cleavage site to be located beside the gly-gly amino acid residues (numbers 24 and 25) (FIG. 4). A peptide was synthesized corresponding to amino acid sequence of residues 26-46 inclusive.

Synthesis of Peptide Analogs

The sequences of the peptide analogs used in this study are listed in Table 1. The peptides were synthesized by methods known in the art. The peptides were dissolved to 1 mg per ml in sterile distilled deionized water. To any insoluble peptides, 10% (vol/vol) acetic acid, 20% (vol/vol) acetonitrile or 100% (vol/vol) dimethylformamide (DMF) was subsequently added. Peptides were stored at −20° C. until used.

Restoration of Phenotypic Defects by Addition of CSP

To determine if the synthetic peptide could restore defective phenotypes of the comC mutants, a chemically synthesized 21-amino acid competence-stimulating peptide (CSP) [SEQ ID NO:11] (Li et al., 2001) was used in complementary experiments. The peptide was freshly dissolved in sterile distilled water to a concentration of 1 mg/ml. The CSP solution was then added to the cultures at a final concentration of 2 µg/ml 2 h after inoculation of bacterial cells.

Growth Rates

The parent and mutant strains were grown in THYE medium for assaying their growth curves using a Bioscreen Microbiology Reader incorporating a multi-well disposable microtiter plate (Bioscreen C, Helsinki, Finland). The Bioscreen Reader was equipped with Biolink software program that allowed us to record and display the growth curves and growth rate calculations automatically. The growth of the strains was initiated by inoculating 5 µl of cell suspension into each well containing 200 µl of fresh THYE medium. The cell suspensions were pre-adjusted to the same optical density at $O.D_{600}$ before inoculation. The plates were then placed in the Bioscreen system, which was set up to read optical density automatically every 15 minutes with shaking. The readings of optical density were automatically recorded and converted into growth curves. Each assay was performed in quadruplicate.

Bacterial Strains and Growth Conditions

Seven strains of *S. mutans* were used in this study (strains include: BM71, GB14, H7, JH1005, LT11, NG8, and UAB159. All the strains were cultured from freeze-dried ampoules and routinely maintained on Todd-Hewitt Yeast Extract (THYE) plates. For selection of antibiotic resistant colonies following transformation, the medium was supplemented with either erythromycin (Em) (10 µg/ml) or kanamycin (Km) (500 µg/ml).

*S. mutans* strain wild-type UA159 and its comD null mutant were routinely grown on Todd-Hewitt supplemented with 0.3% (wt/vol) yeast extract (THYE) agar plates and incubated at 37° C. in air with 5% $CO_2$. For biofilm experiments, *S. mutans* strains were grown in a semidefined minimal medium (SDM) supplemented with 5 mM glucose as described previously (Li et al., 2002). The replicative plasmid pDL289 (Buckley et al., 1995) was used as donor DNA for genetic transformation experiments. Plasmid DNA was prepared from *Escherichia coli* cultures by using a commercial plasmid preparation kit (Qiagen). When needed, antibiotics were added as follows: 10 µg erythromycin per ml or 500 µg kanamycin per ml for *S. mutans*, and 50 µg kanamycin per ml for *E. coli*.

Assay for Biofilms Formed on Polystyrene Microtiter Plates (a)

Biofilms were developed on polystyrene microtiter plates to provide a rapid and simple method for assaying genetic transformation. A 4× diluted THYE medium supplemented with final concentration of 0.01% hog gastric mucin was used as biofilm medium (BM). Formation of biofilms was initiated by inoculating 20 µl of cell suspension into each well containing 2 ml of BM and four wells were set up: two for assaying transformation and two for quantification of biofilms. After cultures were incubated at 37° C. for 20 h under an anaerobic condition, fluid medium was removed for viable cell counts. The wells were rinsed once with 10 mM PBS buffer (pH 7.2) and biofilm cells were collected in 2 ml PBS by a gentle sonication for 15 seconds. Both biofilm and the planktonic cells were immediately spread on THYE plates using a spiral system (Spriral Plater, Model D, Cincinnati, Ohio) and incubated at 37° C. under an anaerobic condition. Formation of biofilms was quantified by viable cell counts after 48 h of incubation.

Biofilm Assay. (b)

Biofilms were developed in 96-well polystyrene microtiter plates. The growth of the biofilm was initiated by inoculating 10 µl of an overnight *S. mutans* UA159 culture into 300 µl of SDM-glucose containing different concentrations (0, 0.1, 0.5, 2, and 5 µg per ml) of peptide analogs in the individual wells of a 96-well microtiter plate. Wells without cells were used as blank controls. The microtiter plates were then incubated at 37° C. in air with 5% $CO_2$ for 16 h without agitation. After the incubation, the planktonic cells were carefully removed and the plates were air dried overnight. The plates were then stained with 0.01% (wt/vol) safranin for 10 min, rinsed with sterile distilled water and air dried. Biofilms were quantified by measuring the absorbance of stained biofilms at 490 nm with a microplate reader (model 3550; Bio-Rad Laboratories, Richmond, Calif.).

Competence Assay

To determine if the peptide analogs had any impact on the development of genetic competence, *S. mutans* UA159 wild-type cells were assayed for genetic transformation. Overnight cultures of *S. mutans* UA159 were diluted (1:20) with pre-warmed THYE broth and incubated at 37° C. in air with 5% $CO_2$ until an optical density (OD) of approximately 0.1 at 600 nm was reached. The culture was then divided into six aliquots containing 1 µg/ml of plasmid pDL289 and different concentrations (0, 0.1, 0.5, 2, and 5 µg per ml) of peptide analogs. The cultures were incubated at 37° C. in air with 5% $CO_2$ for 2.5 h, gently sonicated for 10 s to disperse the streptococcal chains, and spread on THYE plates containing kanamycin. Plates were incubated at 37° C. in air with 5% $CO_2$ for 48 h. Total recipient cells were counted by spreading serial dilutions on THYE agar plates without antibiotic. Transformation efficiency was expressed as the percentage of kanamycin resistant transformants over the total number of recipient cells.

Acid Resistance Assay

The effect of peptides on acid tolerance was evaluated by assessment of growth in THYE at pH 7.5 and pH 5.5. Overnight *S. mutans* wild-type UA159 cells were diluted (1:20) with prewarmed THYE broth and incubated at 37° C. in air with 5% $CO_2$ until an $OD_{600}$ of approximately 0.4 was reached. A 20-fold dilution was made into 400 µl of either THYE pH 7.5 or THYE pH 5.5 broth containing different concentrations (0, 0.1, 0.5, 2, and 5 µg per ml) of peptide analogs and added in the individual wells of a 100-well Bioscreen C plate in triplicate. Wells without cells were used as blank controls. A Bioscreen microbiology reader (Labsystems, Helsinki, Finland) was employed to continuously grow cells and measure cell growth for 16 h at 37° C. Measurements were taken every 20 min with shaking to prevent cell aggregation.

Assay for "Steady-State" Biofilms

Biofilms were also grown in a chemostat-based biofilm fermentor to define and optimize the conditions for genetic competence of biofilm-grown cells. The biofilm fermentor was modified in the Mechanical Engineering and Glass Blowing Shops, University of Toronto, based on a similar system described previously (Li and Bowden, 1994). The vessel was made of glass with a working volume of 400 ml. The vessel lip was constructed of stainless steel with 10 sampling ports, which allowed sterile insertion and retrieval of glass rods (0.5 cm in diameter, approximately $4.0\,cm^2$ area immersed in fluid medium), providing abiotic surfaces for accumulation of biofilms. Temperature in the chemostat vessel was maintained at 37° C.±0.1 by a temperature controller (Model R-600F, Cole Farmer Instrument Cop., Vernon Hill, Ill.). The culture pH was controlled by a pH control unit (Digital pH Meter/Controller, Model 501-3400, Barnant Corp. Barrington, Ill.) through the addition of 1M KOH or 1M HCl. The vessel was placed on a magnetic stirrer (Fisher Scientific) and the culture was stirred at 200 rpm by a polypropylene coated magnetic stirrer bar (3 cm in length). Continuous cultures were obtained by pumping fresh 4× diluted THYE medium supplemented with a final concentration of 0.01% hog gastric mucin (Type III, Sigma) into the vessel (400 ml) at the desired dilution rates. Daily maintenance of the chemostat included optical density reading, viable cell counts and pH measurement in fluid cultures. When the cultures reached "steady-state" (at least 10 mean generation times), glass rods were aseptically inserted into the chemostat for the initiation of biofilm formation. Then, biofilms of different ages were removed from the cultures for both genetic transformation and quantification of biofilms using viable cell counts.

Scanning Electron Microscopy (SEM)

To examine spatial distribution and biofilm thickness by scanning electron microscopy, biofilms of different ages were removed by slicing off the bottom of the microtiter wells that were then washed once with 10 mM $KPO_4$ and fixed with 2 ml of 3.7% formaldehyde in 10 mM $KPO_4$ buffer overnight. The samples were then dehydrated with a series of alcohol baths (30%, 50%, 70%, 95% and 100%), critical point dried with liquid $CO_2$, mounted and sputter coated with gold. The samples were then examined using a scanning electron microscope (Model S-2500, Hitachi Instruments, San Jose, Calif.).

Transformation Protocol

Two methods modified based on the protocols described by Perry et al (Infect Immun, 41:722-727) and Lindler and Macrina (J Bacteriol, 166:658-665) were used to assay natural transformation of biofilm cells. Biofilms formed on polystyrene microtiter plates were added with 2 ml of pre-warmed, fresh THYE plus 5% horse serum (THYE-HS) immediately following removal of the BM medium, and the incubation continued at 37° C. After 2 h incubation, a final concentration of 1 µg/ml plasmid DNA or 10 µg/ml of chromosomal DNA was added to each well. The cultures were incubated for an additional 2 h before collection of the cells for plating. To assay induction of competence by synthetic competence stimulating peptide (SCSP) [SEQ ID NO:11], the cultures were incubated for 30 min and a final concentration of 500 ng/ml of SCSP [SEQ ID NO:11] was added to each well. After a 30 min incubation, equal amounts of DNA was added to each well (1 μg/ml plasmid or 10 μg/ml of chromosomal DNA) and incubation continued for another 2 h. Fluid medium was then removed from individual wells and the wells were washed once with PBS buffer. Biofilm cells were collected into 2 ml PBS buffer by gentle sonication or by washing the wells using a pipette. The samples were centrifuged at 12,000×g for 5 min. Both biofilm and planktonic cells were resuspended into 200 μl of fresh medium and were immediately spread on THYE agar plates plus appropriate antibiotics. For the biofilms developed in the chemostat, rods with biofilm cells were removed and placed into 2 ml of pre-warmed, fresh THYE-HS medium for 30 min incubation. Transformation was then initiated by using the same methods as described above. The planktonic cells were also removed to compare the transformation frequency. After completion of the transformation procedures, both biofilm and planktonic cells were spread on THYE agar plus appropriate antibiotic. Transformation frequency was assessed after 48-h incubation. Transformation frequency was expressed as the number of transformants per μg DNA per viable recipient at the time of DNA added.

Donor DNA

Both plasmid and chromosomal DNA were used as donor DNA to assay genetic transformation in this study. Plasmid DNA included an integrative plasmid, pVAGTFA carrying an erythromycin resistance ($Em^r$) determinant and a fragment of the S. mutans gtfA gene. The replicative plasmid, pDL289 carrying a kanamycin resistance gene ($Km^r$) was also used. Chromosomal DNA harboring an $Em^r$ gene was prepared from a recombinant S. mutans strain harboring a chromosomally integrated copy of pVAGTFA.

The present invention has been described in detail and with particular reference to the preferred embodiments; however, it will be understood by one having ordinary skill in the art that changes can be made without departing from the spirit and scope thereof. For example, where the application refers to peptides, it is clear that polypeptides may often be used. Likewise, where a gene is described in the application, it is clear that nucleic acid molecules or gene fragments may often be used.

All publications (including GenBank entries), patents and patent applications are incorporated by reference in their entirety to the same extent as if each individual publication, patent or patent application was specifically and individually indicated to be incorporated by reference in its entirety.

REFERENCES

Aspiras, M. B., R. P. Ellen, and D. G. Cvitkovitch. 2004. ComX activity of Streptococcus mutans growing in biofilms. FEMS Microbiol. Lett. 238: 167-174.

Balaban, N., L. V. Collins, J. S. Cullor, E. B. Hume, E. Medina-Acosta, O. Vieira da Motta, R. C'Callaghan, P. V. Rossitto, M. E. Shirtliff, L. Serafim da Silveira, A. Tarkowski, and J. V. Torres. 2000. Prevention of diseases caused by Staphylococcus aureus using the peptide RIP. Peptides 21:1301-1311.

Banas, J. A. 2004. Virulence properties of Streptococcus mutans. Front. Bioscience 9: 1267-1277.

Bassler, B. L. 2002. Small talk. Cell to cell communication in bacteria. Cell 109:421-424.

Buckley, N. D., L. N. Lee, and D. J. LeBlanc. 1995. Use of a novel mobilizable vector to inactivate the scrA gene of Streptococcus sobrinus by allelic replacement. J Bacteriol. 177:5028-5034.

Cvitkovitch, D. G., Y. Li, and R. P. Ellen. 2003. Quorum-sensing and biofilm formation in streptococcal infections. J. Clin. Invest. 112:1626-1632.

Davies, D. G., M. R. Parsek, J. P. Pearson, B. H. Iglewski, J. W. Costerton, E. P. Greenberg. 1998. The involvement of cell-to cell signals in the development of a bacterial biofilm. Science 280:295-298.

Dunny, G. M., and B. A. B. Leonard. 1997. Cell-cell communication in Gram-positive bacteria. Annu. Rev. Microbiol. 51:527-564.

Eberl, L., S. Molin, and M. Givskov. 1999. Surface motility of Serratia liquefaciens MG1. J. Bacteriol. 181:1703-1712.

Havarstein, L. S., G. Gaustad, I. F. Nes, and D. A. Morrison. 1996. Identification of the streptococcal competence pheromone receptor. Mol. Microbiol. 21:863-869.

Hentzer, M., and M. Givskov. 2003. Pharmacological inhibition of quorum sensing for the treatment of chronic bacterial infections. J. Clin. Invest. 112:1300-1307.

Jefferson, K. K. 2004. What drives bacteria to produce a biofilm? FEMS Microbiol. Rev. 236:163-173.

Ji, G., R. C. Beavisand, and R. P. Novick. 1995. Cell density control of staphylococcal virulence mediated by an octapeptide pheromone. Proc. Natl. Acad. Sci. USA. 92:12055-12059.

Lau, P. C. Y., C. K. Sung, J. H. Lee, D. A. Morrison, and D. G. Cvitkovitch. 2002. PCR ligation mutagenesis in transformable streptococci: application and efficiency. J. Microbiol. Methods 49:193-205.

Lee, M. S., and D. A. Morrison. 1999. Identification of a new regulator in Streptococcus pneumonias linking quorum sensing to competence for genetic transformation. J. Bacteriol. 181:5004-5016.

Lewis, K. 2001. Riddle of biofilm resistance. Antimicrob. Agents Chemother. 45:999-1007.

Li, Y.-H., P. C. Y. Lau, J. H. Lee, R. P. Ellen, and D. G. Cvitkovitch. 2001. Natural genetic transformation of Streptococcus mutans growing in biofilms. J. Bacteriol. 183:897-908.

Li, Y., N. Tang, M. B. Aspiras, P. C. Y. Lau, J. H. Lee, R. P. Ellen, and D. G. Cvitkovitch. 2002. A quorum-sensing signaling system essential for genetic competence in Streptococcus mutans is involved in biofilm formation. J. Bacteriol. 184:2699-2708.

Luo, P., H. Li, and D. A. Morrison. 2003. ComX is a unique link between multiple quorum sensing outputs and competence in Streptococcus pneumoniae. Mol. Microbiol. 50:623-633.

Marsh, P. D. 2004. Dental plaque as a microbial biofilm. Caries Res. 38:204-211.

Mayville, P., G. Ji, R. Beavis, H. Yang, M. Goger, R. P. Novick, and T. W. Muir. 1999. Structure-activity analysis of synthetic autoinducing thiolactone peptides from Staphylococcus aureus responsible for virulence. Proc. Natl. Acad. Sci. USA. 96:1218-1223.

Mitchell, T. J. 2003. The pathogenesis of streptococcal infections: from tooth decay to meningitis. Nat. Rev. Microbiol. 1:219-230.

Oggioni, M. R., F. Iannelli, S. Ricci, D. Chiavolini, R. Parigi, C. Trappetti, J.-P. Clayerys, and G. Pozzi. 2004. Antibacterial activity of a competence-stimulating peptide in experimental sepsis caused by Streptococcus pneumoniae. Antimicrob. Agents Chemother. 48:4725-4732.

Otto, M., R. Siibmuth, G. Vuong, G. Jung, and F. Gotz. 1999. Inhibition of virulence factor expression in Staphylococcus aureus by the Staphylococcus epidermidis agr pheromone and derivatives. FEES Lett. 450:257-262.

Petersen, F. C., and A. A. Scheie. 2000. Genetic transformation in Streptococcus mutans requires a peptide secretion-like apparatus. Oral Microbiol. Immunol. 15:329-34.

Shapiro, J. A. 1998. Thinking about bacterial populations as multicellular organisms. Arum Rev. Microbiol. 52:81-104.

SEQUENCE LISTING

<160> NUMBER OF SEQ ID NOS: 28

<210> SEQ ID NO 1
<211> LENGTH: 141
<212> TYPE: DNA
<213> ORGANISM: Streptococcus mutans
<220> FEATURE:
<221> NAME/KEY: CDS
<222> LOCATION: (1)..(141)

<400> SEQUENCE: 1

```
atg aaa aaa aca cta tca tta aaa aat gac ttt aaa gaa att aag act        48
Met Lys Lys Thr Leu Ser Leu Lys Asn Asp Phe Lys Glu Ile Lys Thr
1               5                   10                  15 gat gaa tta gag att atc att ggc gga agc gga agc cta tca aca ttt        96
Asp Glu Leu Glu Ile Ile Ile Gly Gly Ser Gly Ser Leu Ser Thr Phe
                20                  25                  30 ttc cgg ctg ttt aac aga agt ttt aca caa gct ttg gga aaa taa           141
Phe Arg Leu Phe Asn Arg Ser Phe Thr Gln Ala Leu Gly Lys
            35                  40                  45
```

<210> SEQ ID NO 2
<211> LENGTH: 46
<212> TYPE: PRT
<213> ORGANISM: Streptococcus mutans

<400> SEQUENCE: 2

```
Met Lys Lys Thr Leu Ser Leu Lys Asn Asp Phe Lys Glu Ile Lys Thr
1               5                   10                  15

Asp Glu Leu Glu Ile Ile Ile Gly Gly Ser Gly Ser Leu Ser Thr Phe
                20                  25                  30

Phe Arg Leu Phe Asn Arg Ser Phe Thr Gln Ala Leu Gly Lys
            35                  40                  45
```

<210> SEQ ID NO 3
<211> LENGTH: 1326
<212> TYPE: DNA
<213> ORGANISM: Streptococcus mutans
<220> FEATURE:
<221> NAME/KEY: CDS
<222> LOCATION: (1)..(1326)

<400> SEQUENCE: 3

```
atg aat gaa gcc tta atg ata ctt tca aat ggt tta tta act tat cta        48
Met Asn Glu Ala Leu Met Ile Leu Ser Asn Gly Leu Leu Thr Tyr Leu
1               5                   10                  15 acc gtt cta ttt ctc ttg ttt cta ttt tct aag gta agt aat gtc act        96
Thr Val Leu Phe Leu Leu Phe Leu Phe Ser Lys Val Ser Asn Val Thr
                20                  25                  30 tta tcg aaa aag gaa tta act ctt ttt tcg ata agc aat ttt ctg ata       144
Leu Ser Lys Lys Glu Leu Thr Leu Phe Ser Ile Ser Asn Phe Leu Ile
            35                  40                  45 atg att gct gtt acg atg gtg aac gta aac ctg ttt tat cct gca gag       192
Met Ile Ala Val Thr Met Val Asn Val Asn Leu Phe Tyr Pro Ala Glu
        50                  55                  60 cct ctt tat ttt ata gct tta tca att tat ctt aat aga cag aat agt       240
Pro Leu Tyr Phe Ile Ala Leu Ser Ile Tyr Leu Asn Arg Gln Asn Ser
65                  70                  75                  80 ctt tct cta aat ata ttt tat ggt ctg ctg cct gtt gcc agt tct gac       288
Leu Ser Leu Asn Ile Phe Tyr Gly Leu Leu Pro Val Ala Ser Ser Asp
                85                  90                  95
```

-continued

| | |
|---|---|
| ttg ttt agg cgg gca atc ata ttc ttt atc ttg gat gga act caa gga<br>Leu Phe Arg Arg Ala Ile Ile Phe Phe Ile Leu Asp Gly Thr Gln Gly<br>          100                        105                        110 | 336 |
| att gta atg ggc agt agc att ata acc acc tat atg atc gag ttt gca<br>Ile Val Met Gly Ser Ser Ile Ile Thr Thr Tyr Met Ile Glu Phe Ala<br>          115                        120                        125 | 384 |
| gga ata gcg cta agt tac ctc ttt ctc agt gtg ttc aat gtt gat att<br>Gly Ile Ala Leu Ser Tyr Leu Phe Leu Ser Val Phe Asn Val Asp Ile<br>130                        135                        140 | 432 |
| ggt cga ctt aaa gat agt ttg acc aag atg aag gtc aaa aaa cgc ttg<br>Gly Arg Leu Lys Asp Ser Leu Thr Lys Met Lys Val Lys Lys Arg Leu<br>145                      150                        155                        160 | 480 |
| att cca atg aat att act atg ctt cta tac tac ctt tta ata cag gta<br>Ile Pro Met Asn Ile Thr Met Leu Leu Tyr Tyr Leu Leu Ile Gln Val<br>                    165                        170                        175 | 528 |
| ttg tat gtt ata gag agt tat aat gtg ata ccg act tta aaa ttt cgt<br>Leu Tyr Val Ile Glu Ser Tyr Asn Val Ile Pro Thr Leu Lys Phe Arg<br>                    180                        185                        190 | 576 |
| aaa ttt gtc gtt att gtc tat ctt att tta ttt ttg att ctg atc tca<br>Lys Phe Val Val Ile Val Tyr Leu Ile Leu Phe Leu Ile Leu Ile Ser<br>          195                        200                        205 | 624 |
| ttt tta agc caa tat acc aaa caa aag gtt caa aat gag ata atg gca<br>Phe Leu Ser Gln Tyr Thr Lys Gln Lys Val Gln Asn Glu Ile Met Ala<br>210                        215                        220 | 672 |
| caa aag gaa gct cag att cga aat atc acc cag tat agt cag caa ata<br>Gln Lys Glu Ala Gln Ile Arg Asn Ile Thr Gln Tyr Ser Gln Gln Ile<br>225                      230                        235                        240 | 720 |
| gaa tct ctt tac aag gat att cga agt ttc cgc cat gat tat ctg aat<br>Glu Ser Leu Tyr Lys Asp Ile Arg Ser Phe Arg His Asp Tyr Leu Asn<br>                    245                        250                        255 | 768 |
| att tta act agc ctc aga tta ggc att gaa aat aaa gat tta gct agt<br>Ile Leu Thr Ser Leu Arg Leu Gly Ile Glu Asn Lys Asp Leu Ala Ser<br>          260                        265                        270 | 816 |
| att gaa aag att tac cat caa atc tta gaa aaa aca gga cat caa ttg<br>Ile Glu Lys Ile Tyr His Gln Ile Leu Glu Lys Thr Gly His Gln Leu<br>275                        280                        285 | 864 |
| cag gat acc cgt tat aat atc ggc cat cta gct aat att caa aac gat<br>Gln Asp Thr Arg Tyr Asn Ile Gly His Leu Ala Asn Ile Gln Asn Asp<br>          290                        295                        300 | 912 |
| gct gtc aag ggt atc ttg tca gca aaa atc tta gaa gct cag aat aaa<br>Ala Val Lys Gly Ile Leu Ser Ala Lys Ile Leu Glu Ala Gln Asn Lys<br>305                      310                        315                        320 | 960 |
| aag att gct gtc aat gta gaa gtc tca agt aaa ata caa ctg cct gag<br>Lys Ile Ala Val Asn Val Glu Val Ser Ser Lys Ile Gln Leu Pro Glu<br>                    325                        330                        335 | 1008 |
| atg gag ttg ctt gat ttc att acc ata ctt tct atc ttg tgt gat aat<br>Met Glu Leu Leu Asp Phe Ile Thr Ile Leu Ser Ile Leu Cys Asp Asn<br>                    340                        345                        350 | 1056 |
| gcc att gag gct gct ttc gaa tca tta aat cct gaa att cag tta gcc<br>Ala Ile Glu Ala Ala Phe Glu Ser Leu Asn Pro Glu Ile Gln Leu Ala<br>          355                        360                        365 | 1104 |
| ttt ttt aag aaa aat ggc agt ata gtc ttt atc att cag aat tcc acc<br>Phe Phe Lys Lys Asn Gly Ser Ile Val Phe Ile Ile Gln Asn Ser Thr<br>370                      375                        380 | 1152 |
| aaa gaa aaa caa ata gat gtg agt aaa att ttt aaa gaa aac tat tcc<br>Lys Glu Lys Gln Ile Asp Val Ser Lys Ile Phe Lys Glu Asn Tyr Ser<br>385                      390                        395                        400 | 1200 |
| act aaa ggc tcc aat cgc ggt att ggt tta gca aag gtg aat cat att<br>Thr Lys Gly Ser Asn Arg Gly Ile Gly Leu Ala Lys Val Asn His Ile<br>                    405                        410                        415 | 1248 |

```
ctt gaa cat tat ccc aaa acc agt tta caa aca agc aat cat cat cat      1296
Leu Glu His Tyr Pro Lys Thr Ser Leu Gln Thr Ser Asn His His His
            420                 425                 430 tta ttc aag caa ctc cta ata ata aaa tag                              1326
Leu Phe Lys Gln Leu Leu Ile Ile Lys
            435                 440
```

<210> SEQ ID NO 4
<211> LENGTH: 441
<212> TYPE: PRT
<213> ORGANISM: Streptococcus mutans

<400> SEQUENCE: 4

```
Met Asn Glu Ala Leu Met Ile Leu Ser Asn Gly Leu Leu Thr Tyr Leu
1               5                   10                  15

Thr Val Leu Phe Leu Leu Phe Leu Phe Ser Lys Val Ser Asn Val Thr
            20                  25                  30

Leu Ser Lys Lys Glu Leu Thr Leu Phe Ser Ile Ser Asn Phe Leu Ile
        35                  40                  45

Met Ile Ala Val Thr Met Val Asn Val Asn Leu Phe Tyr Pro Ala Glu
    50                  55                  60

Pro Leu Tyr Phe Ile Ala Leu Ser Ile Tyr Leu Asn Arg Gln Asn Ser
65                  70                  75                  80

Leu Ser Leu Asn Ile Phe Tyr Gly Leu Leu Pro Val Ala Ser Ser Asp
                85                  90                  95

Leu Phe Arg Arg Ala Ile Ile Phe Phe Ile Leu Asp Gly Thr Gln Gly
            100                 105                 110

Ile Val Met Gly Ser Ser Ile Ile Thr Thr Tyr Met Ile Glu Phe Ala
        115                 120                 125

Gly Ile Ala Leu Ser Tyr Leu Phe Leu Ser Val Phe Asn Val Asp Ile
    130                 135                 140

Gly Arg Leu Lys Asp Ser Leu Thr Lys Met Lys Val Lys Lys Arg Leu
145                 150                 155                 160

Ile Pro Met Asn Ile Thr Met Leu Leu Tyr Tyr Leu Leu Ile Gln Val
                165                 170                 175

Leu Tyr Val Ile Glu Ser Tyr Asn Val Ile Pro Thr Leu Lys Phe Arg
            180                 185                 190

Lys Phe Val Val Ile Val Tyr Leu Ile Leu Phe Leu Ile Leu Ile Ser
        195                 200                 205

Phe Leu Ser Gln Tyr Thr Lys Gln Lys Val Gln Asn Glu Ile Met Ala
    210                 215                 220

Gln Lys Glu Ala Gln Ile Arg Asn Ile Thr Gln Tyr Ser Gln Gln Ile
225                 230                 235                 240

Glu Ser Leu Tyr Lys Asp Ile Arg Ser Phe Arg His Asp Tyr Leu Asn
                245                 250                 255

Ile Leu Thr Ser Leu Arg Leu Gly Ile Glu Asn Lys Asp Leu Ala Ser
            260                 265                 270

Ile Glu Lys Ile Tyr His Gln Ile Leu Glu Lys Thr Gly His Gln Leu
        275                 280                 285

Gln Asp Thr Arg Tyr Asn Ile Gly His Leu Ala Asn Ile Gln Asn Asp
    290                 295                 300

Ala Val Lys Gly Ile Leu Ser Ala Lys Ile Leu Glu Ala Gln Asn Lys
305                 310                 315                 320

Lys Ile Ala Val Asn Val Glu Val Ser Ser Lys Ile Gln Leu Pro Glu
                325                 330                 335
```

```
Met Glu Leu Leu Asp Phe Ile Thr Ile Leu Ser Ile Leu Cys Asp Asn
                340                 345                 350

Ala Ile Glu Ala Ala Phe Glu Ser Leu Asn Pro Glu Ile Gln Leu Ala
            355                 360                 365

Phe Phe Lys Lys Asn Gly Ser Ile Val Phe Ile Ile Gln Asn Ser Thr
        370                 375                 380

Lys Glu Lys Gln Ile Asp Val Ser Lys Ile Phe Lys Glu Asn Tyr Ser
385                 390                 395                 400

Thr Lys Gly Ser Asn Arg Gly Ile Gly Leu Ala Lys Val Asn His Ile
                405                 410                 415

Leu Glu His Tyr Pro Lys Thr Ser Leu Gln Thr Ser Asn His His His
            420                 425                 430

Leu Phe Lys Gln Leu Leu Ile Ile Lys
        435                 440

<210> SEQ ID NO 5
<211> LENGTH: 750
<212> TYPE: DNA
<213> ORGANISM: Streptococcus mutans
<220> FEATURE:
<221> NAME/KEY: CDS
<222> LOCATION: (1)..(750)

<400> SEQUENCE: 5 atg att tct att ttt gta ttg gaa gat gat ttt tta caa caa gga cgt      48
Met Ile Ser Ile Phe Val Leu Glu Asp Asp Phe Leu Gln Gln Gly Arg
1               5                   10                  15 ctt gaa acc acc att gca gct atc atg aaa gaa aaa aat tgg tct tat      96
Leu Glu Thr Thr Ile Ala Ala Ile Met Lys Glu Lys Asn Trp Ser Tyr
            20                  25                  30 aaa gaa ttg act att ttt gga aaa cca caa caa ctt att gac gct atc     144
Lys Glu Leu Thr Ile Phe Gly Lys Pro Gln Gln Leu Ile Asp Ala Ile
        35                  40                  45 cct gaa aag ggc aat cac cag att ttc ttt ttg gat att gaa atc aaa     192
Pro Glu Lys Gly Asn His Gln Ile Phe Phe Leu Asp Ile Glu Ile Lys
    50                  55                  60 aaa gag gaa aag aaa gga ctg gaa gta gcc aat cag att aga cag cat     240
Lys Glu Glu Lys Lys Gly Leu Glu Val Ala Asn Gln Ile Arg Gln His
65                  70                  75                  80 aat cct agt gca gtt att gtc ttt gtc acg aca cat tct gag ttt atg     288
Asn Pro Ser Ala Val Ile Val Phe Val Thr Thr His Ser Glu Phe Met
                85                  90                  95 ccc ctc act ttt cag tat cag gta tct gct ttg gat ttt att gat aaa     336
Pro Leu Thr Phe Gln Tyr Gln Val Ser Ala Leu Asp Phe Ile Asp Lys
            100                 105                 110 tct ttg aat cct gag gag ttc tcc cac cgc att gaa tca gcg ctg tat     384
Ser Leu Asn Pro Glu Glu Phe Ser His Arg Ile Glu Ser Ala Leu Tyr
        115                 120                 125 tat gct atg gaa aac agc cag aag aat ggt caa tca gag gaa ctt ttt     432
Tyr Ala Met Glu Asn Ser Gln Lys Asn Gly Gln Ser Glu Glu Leu Phe
    130                 135                 140 att ttc cat tca tct gaa act cag ttt cag gtc cct ttt gct gag att     480
Ile Phe His Ser Ser Glu Thr Gln Phe Gln Val Pro Phe Ala Glu Ile
145                 150                 155                 160 ctg tat ttt gaa aca tct tca aca gcc cat aag ctc tgc ctt tat act     528
Leu Tyr Phe Glu Thr Ser Ser Thr Ala His Lys Leu Cys Leu Tyr Thr
                165                 170                 175 tat gat gaa cgg att gaa ttc tac ggc agt atg act gac att gtt aaa     576
Tyr Asp Glu Arg Ile Glu Phe Tyr Gly Ser Met Thr Asp Ile Val Lys
            180                 185                 190
```

-continued

```
atg gat aag aga ctt ttt cag tgc cat cgc tct ttt att gtc aat cct        624
Met Asp Lys Arg Leu Phe Gln Cys His Arg Ser Phe Ile Val Asn Pro
        195                 200                 205 gcc aat att acc cgt att gat cgg aaa aaa cgc ttg gcc tat ttt cga        672
Ala Asn Ile Thr Arg Ile Asp Arg Lys Lys Arg Leu Ala Tyr Phe Arg
    210                 215                 220 aat aat aag tct tgt ctt att tca cga act aag tta aca aaa ctg aga        720
Asn Asn Lys Ser Cys Leu Ile Ser Arg Thr Lys Leu Thr Lys Leu Arg
225                 230                 235                 240 gct gtg att gct gat caa agg aga gca aaa                                750
Ala Val Ile Ala Asp Gln Arg Arg Ala Lys
                245                 250

<210> SEQ ID NO 6
<211> LENGTH: 250
<212> TYPE: PRT
<213> ORGANISM: Streptococcus mutans

<400> SEQUENCE: 6

Met Ile Ser Ile Phe Val Leu Glu Asp Asp Phe Leu Gln Gln Gly Arg
1               5                   10                  15

Leu Glu Thr Thr Ile Ala Ala Ile Met Lys Glu Lys Asn Trp Ser Tyr
            20                  25                  30

Lys Glu Leu Thr Ile Phe Gly Lys Pro Gln Gln Leu Ile Asp Ala Ile
        35                  40                  45

Pro Glu Lys Gly Asn His Gln Ile Phe Phe Leu Asp Ile Glu Ile Lys
    50                  55                  60

Lys Glu Glu Lys Lys Gly Leu Glu Val Ala Asn Gln Ile Arg Gln His
65                  70                  75                  80

Asn Pro Ser Ala Val Ile Val Phe Val Thr Thr His Ser Glu Phe Met
                85                  90                  95

Pro Leu Thr Phe Gln Tyr Gln Val Ser Ala Leu Asp Phe Ile Asp Lys
            100                 105                 110

Ser Leu Asn Pro Glu Glu Phe Ser His Arg Ile Glu Ser Ala Leu Tyr
        115                 120                 125

Tyr Ala Met Glu Asn Ser Gln Lys Asn Gly Gln Ser Glu Glu Leu Phe
    130                 135                 140

Ile Phe His Ser Ser Glu Thr Gln Phe Gln Val Pro Phe Ala Glu Ile
145                 150                 155                 160

Leu Tyr Phe Glu Thr Ser Ser Thr Ala His Lys Leu Cys Leu Tyr Thr
                165                 170                 175

Tyr Asp Glu Arg Ile Glu Phe Tyr Gly Ser Met Thr Asp Ile Val Lys
            180                 185                 190

Met Asp Lys Arg Leu Phe Gln Cys His Arg Ser Phe Ile Val Asn Pro
        195                 200                 205

Ala Asn Ile Thr Arg Ile Asp Arg Lys Lys Arg Leu Ala Tyr Phe Arg
    210                 215                 220

Asn Asn Lys Ser Cys Leu Ile Ser Arg Thr Lys Leu Thr Lys Leu Arg
225                 230                 235                 240

Ala Val Ile Ala Asp Gln Arg Arg Ala Lys
                245                 250

<210> SEQ ID NO 7
<211> LENGTH: 46
<212> TYPE: PRT
<213> ORGANISM: Streptococcus mutans
```

```
<220> FEATURE:
<221> NAME/KEY: PEPTIDE
<222> LOCATION: (1)..(46)

<400> SEQUENCE: 7

Met Lys Lys Thr Pro Ser Leu Lys Asn Asp Phe Lys Glu Ile Lys Thr
1               5                   10                  15

Asp Glu Leu Glu Ile Ile Ile Gly Gly Ser Gly Ser Leu Ser Thr Phe
            20                  25                  30

Phe Arg Leu Phe Asn Arg Ser Phe Thr Gln Ala Leu Gly Lys
        35                  40                  45

<210> SEQ ID NO 8
<211> LENGTH: 46
<212> TYPE: PRT
<213> ORGANISM: Streptococcus mutans
<220> FEATURE:
<221> NAME/KEY: PEPTIDE
<222> LOCATION: (1)..(46)

<400> SEQUENCE: 8

Met Lys Lys Thr Leu Ser Leu Lys Asn Asp Phe Lys Glu Ile Lys Thr
1               5                   10                  15

Asp Glu Leu Glu Ile Ile Ile Gly Gly Ser Gly Ser Leu Ser Thr Phe
            20                  25                  30

Phe Arg Leu Phe Asn Arg Ser Phe Thr Gln Ala Leu Gly Lys
        35                  40                  45

<210> SEQ ID NO 9
<211> LENGTH: 46
<212> TYPE: PRT
<213> ORGANISM: Streptococcus mutans
<220> FEATURE:
<221> NAME/KEY: PEPTIDE
<222> LOCATION: (1)..(46)

<400> SEQUENCE: 9

Met Lys Lys Thr Leu Ser Leu Lys Asn Asp Phe Lys Glu Ile Lys Thr
1               5                   10                  15

Asp Glu Leu Glu Ile Ile Ile Gly Gly Ser Gly Ser Leu Ser Thr Phe
            20                  25                  30

Phe Arg Leu Phe Asn Arg Ser Phe Thr Gln Ala Leu Gly Lys
        35                  40                  45

<210> SEQ ID NO 10
<211> LENGTH: 43
<212> TYPE: PRT
<213> ORGANISM: Streptococcus mutans
<220> FEATURE:
<221> NAME/KEY: PEPTIDE
<222> LOCATION: (1)..(43)

<400> SEQUENCE: 10

Met Lys Lys Thr Leu Ser Leu Lys Asn Asp Phe Lys Glu Ile Lys Thr
1               5                   10                  15

Asp Glu Leu Glu Ile Ile Ile Gly Gly Ser Gly Thr Leu Ser Thr Phe
            20                  25                  30

Phe Arg Leu Phe Asn Arg Ser Phe Thr Gln Ala
        35                  40
```

```
<210> SEQ ID NO 11
<211> LENGTH: 46
<212> TYPE: PRT
<213> ORGANISM: Streptococcus mutans
<220> FEATURE:
<221> NAME/KEY: PEPTIDE
<222> LOCATION: (1)..(46)

<400> SEQUENCE: 11

Met Lys Lys Thr Leu Ser Leu Lys Asn Asp Phe Lys Glu Ile Lys Thr
1               5                   10                  15

Asp Glu Leu Glu Ile Ile Ile Gly Gly Ser Gly Ser Leu Ser Thr Phe
                20                  25                  30

Phe Arg Leu Phe Asn Arg Ser Phe Thr Gln Ala Leu Gly Lys
            35                  40                  45

<210> SEQ ID NO 12
<211> LENGTH: 46
<212> TYPE: PRT
<213> ORGANISM: Streptococcus mutans
<220> FEATURE:
<221> NAME/KEY: PEPTIDE
<222> LOCATION: (1)..(46)

<400> SEQUENCE: 12

Met Lys Lys Thr Leu Ser Leu Lys Asn Asp Phe Lys Glu Ile Lys Thr
1               5                   10                  15

Asp Glu Leu Glu Ile Ile Ile Gly Gly Ser Gly Ser Leu Ser Thr Phe
                20                  25                  30

Phe Arg Leu Phe Asn Arg Ser Phe Thr Gln Ala Leu Gly Lys
            35                  40                  45

<210> SEQ ID NO 13
<211> LENGTH: 46
<212> TYPE: PRT
<213> ORGANISM: Streptococcus mutans
<220> FEATURE:
<221> NAME/KEY: PEPTIDE
<222> LOCATION: (1)..(46)

<400> SEQUENCE: 13

Met Lys Lys Thr Leu Ser Leu Lys Asn Asp Phe Lys Glu Ile Lys Thr
1               5                   10                  15

Asp Glu Leu Glu Ile Ile Ile Gly Gly Ser Gly Ser Leu Ser Thr Phe
                20                  25                  30

Phe Arg Leu Phe Asn Arg Ser Phe Thr Gln Ala Leu Gly Lys
            35                  40                  45

<210> SEQ ID NO 14
<211> LENGTH: 21
<212> TYPE: PRT
<213> ORGANISM: synthetic construct
<220> FEATURE:
<221> NAME/KEY: PEPTIDE
<222> LOCATION: (1)..(21)

<400> SEQUENCE: 14

Ser Gly Ser Leu Ser Thr Phe Phe Arg Leu Phe Asn Arg Ser Phe Thr
1               5                   10                  15

Gln Ala Leu Gly Lys
            20
```

```
<210> SEQ ID NO 15
<211> LENGTH: 19
<212> TYPE: DNA
<213> ORGANISM: synthetic construct
<220> FEATURE:
<221> NAME/KEY: PRIMER
<222> LOCATION: (1)..(19)

<400> SEQUENCE: 15
agttttttgt ctggctgcg                                                    19

<210> SEQ ID NO 16
<211> LENGTH: 20
<212> TYPE: DNA
<213> ORGANISM: synthetic construct
<220> FEATURE:
<221> NAME/KEY: PRIMER
<222> LOCATION: (1)..(20)

<400> SEQUENCE: 16
tccactaaag gctccaatcg                                                   20

<210> SEQ ID NO 17
<211> LENGTH: 24
<212> TYPE: DNA
<213> ORGANISM: synthetic construct
<220> FEATURE:
<221> NAME/KEY: PRIMER
<222> LOCATION: (1)..(24)

<400> SEQUENCE: 17
cgctaagtta cctctttctc agtg                                              24

<210> SEQ ID NO 18
<211> LENGTH: 21
<212> TYPE: DNA
<213> ORGANISM: synthetic construct
<220> FEATURE:
<221> NAME/KEY: PRIMER
<222> LOCATION: (1)..(21)

<400> SEQUENCE: 18
gcttcctttt gtgccattat c                                                 21

<210> SEQ ID NO 19
<211> LENGTH: 21
<212> TYPE: DNA
<213> ORGANISM: synthetic construct
<220> FEATURE:
<221> NAME/KEY: PRIMER
<222> LOCATION: (1)..(21)

<400> SEQUENCE: 19
cctgaaaagg gcaatcacca g                                                 21

<210> SEQ ID NO 20
<211> LENGTH: 22
<212> TYPE: DNA
<213> ORGANISM: synthetic construct
<220> FEATURE:
<221> NAME/KEY: PRIMER
<222> LOCATION: (1)..(22)

<400> SEQUENCE: 20
gcgatggcac tgaaaaagtc tc                                                22
```

<210> SEQ ID NO 21
<211> LENGTH: 2557
<212> TYPE: DNA
<213> ORGANISM: Streptococcus mutans
<220> FEATURE:
<221> NAME/KEY: misc_feature
<222> LOCATION: (1)..(2557)

<400> SEQUENCE: 21

| | | | | | |
|---|---|---|---|---|---|
| acattatgtg | tcctaaggaa | aatattactt | tttcaagaaa | atccatgatt | ttttcataaa | 60 |
| aaatagtata | ctaattataa | tcaaaaaaag | gagatataaa | atgaaaaaaa | cactatcatt | 120 |
| aaaaaatgac | tttaaagaaa | ttaagactga | tgaattagag | attatcattg | gcggaagcgg | 180 |
| aagcctatca | acatttttcc | ggctgtttaa | cagaagtttt | acacaagctt | tgggaaaata | 240 |
| agataggcta | acattggaat | aaaacaaggc | tggatttatt | attccagcct | ttttaaatgt | 300 |
| aaaataaaaa | tacagggtta | aataatcaag | tgtgctgtcg | tggatgagaa | gataaaacta | 360 |
| tctcttagag | aataggcctc | ctctatttta | ttattaggag | ttgcttgaat | aaatgatgat | 420 |
| gattgcttgt | ttgtaaactg | gttttgggat | aatgttcaag | aatatgattc | acctttgcta | 480 |
| aaccaatacc | gcgattggag | cctttagtgg | aatagttttc | tttaaaaatt | ttactcacat | 540 |
| ctatttgttt | ttcttggtg | gaattctgaa | tgataaagac | tatactgcca | tttttcttaa | 600 |
| aaaaggctaa | ctgaatttca | ggatttaatg | attcgaaagc | agcctcaatg | gcattatcac | 660 |
| acaagataga | aagtatggta | atgaaatcaa | gcaactccat | ctcaggcagt | tgtattttac | 720 |
| ttgagacttc | tacattgaca | gcaatctttt | tattctgagc | ttctaagatt | tttgctgaca | 780 |
| agataccctt | gacagcatcg | ttttgaatat | tagctagatg | gccgatatta | taacgggtat | 840 |
| cctgcaattg | atgtcctgtt | ttttctaaga | tttgatggta | aatcttttca | atactagcta | 900 |
| aatctttatt | ttcaatgcct | aatctgaggc | tagttaaaat | attcagataa | tcatggcgga | 960 |
| aacttcgaat | atccttgtaa | agagattcta | tttgctgact | atactgggtg | atatttcgaa | 1020 |
| tctgagcttc | cttttgtgcc | attatctcat | tttgaacctt | ttgtttggta | tattggctta | 1080 |
| aaaatgagat | cagaatcaaa | aataaaataa | gatagacaat | aacgacaaat | ttacgaaatt | 1140 |
| ttaaagtcgg | tatcacatta | taactctcta | taacatacaa | tacctgtatt | aaaaggtagt | 1200 |
| atagaagcat | agtaatattc | attggaatca | agcgtttttt | gaccttcatc | ttggtcaaac | 1260 |
| tatctttaag | tcgaccaata | tcaacattga | acacactgag | aaagaggtaa | cttagcgcta | 1320 |
| ttcctgcaaa | ctcgatcata | taggtggtta | taatgctact | gcccattaca | attccttgag | 1380 |
| ttccatccaa | gataaagaat | atgattgccc | gcctaaacaa | gtcagaactg | gcaacaggca | 1440 |
| gcagaccata | aaatatattt | agagaaagac | tattctgtct | attaagataa | attgataaag | 1500 |
| ctataaaata | aagaggctct | gcaggataaa | acaggtttac | gttcaccatc | gtaacagcaa | 1560 |
| tcattatcag | aaaattgctt | atcgaaaaaa | gagttaattc | cttttttcgat | aaagtgacat | 1620 |
| tacttacctt | agaaaataga | aacaagagaa | atagaacggt | tagataagtt | aataaaccat | 1680 |
| ttgaaagtat | cattaaggct | tcattcattt | tgctctcctt | tgatcagcaa | tcacagctct | 1740 |
| cagttttgtt | aacttagttc | gtgaaataag | acaagactta | ttatttcgaa | aataggccaa | 1800 |
| gcgttttttc | cgatcaatac | gggtaatatt | ggcaggattg | acaataaaag | agcgatggca | 1860 |
| ctgaaaaagt | ctcttatcca | ttttaacaat | gtcagtcata | ctgccgtaga | attcaatccg | 1920 |
| ttcatcataa | gtataaaggc | agagcttatg | ggctgttgaa | gatgtttcaa | aatacagaat | 1980 |
| ctcagcaaaa | gggaccctgaa | actgagtttc | agatgaatgg | aaaataaaaa | gttcctctga | 2040 |
| ttgaccattc | ttctggctgt | tttccatagc | ataatacagc | gctgattcaa | tgcggtggga | 2100 |

-continued

```
gaactcctca ggattcaaag atttatcaat aaaatccaaa gcagatacct gatactgaaa        2160
agtgaggggc ataaactcag aatgtgtcgt gacaaagaca ataactgcac taggattatg        2220
ctgtctaatc tgattggcta cttccagtcc tttcttttcc tcttttttga tttcaatatc        2280 caaaagaaa atctggtgat tgcccttttc agggatagcg tcaataagtt gttgtggttt         2340
tccaaaaata gtcaattctt tataagacca attttttct ttcatgatag ctgcaatggt         2400
ggtttcaaga cgtccttgtt gtaaaaaatc atcttccaat acaaaatag aaatcattat         2460 ttctccttta atcttctatt taggttagct gattaacact atacacagaa aaggtataaa        2520
acgatatcac tcaataaaat ctactaactt aataacc                                 2557
```

<210> SEQ ID NO 22
<211> LENGTH: 480
<212> TYPE: DNA
<213> ORGANISM: Streptococcus mutans
<220> FEATURE:
<221> NAME/KEY: CDS
<222> LOCATION: (1)..(408)

<400> SEQUENCE: 22

```
atg gaa gaa gat ttt gaa att gtt ttt aat aag gtt aag cca att gta           48
Met Glu Glu Asp Phe Glu Ile Val Phe Asn Lys Val Lys Pro Ile Val
1               5                   10                  15 tgg aaa tta agc cgt tat tac ttt att aaa atg tgg act cgt gaa gat           96
Trp Lys Leu Ser Arg Tyr Tyr Phe Ile Lys Met Trp Thr Arg Glu Asp
            20                  25                  30 tgg caa caa gag gga atg ttg att ttg cac caa tta tta agg gaa cat          144
Trp Gln Gln Glu Gly Met Leu Ile Leu His Gln Leu Leu Arg Glu His
        35                  40                  45 cca gaa tta gaa gag gat gat aca aaa ttg tat atc tat ttt aag aca          192
Pro Glu Leu Glu Glu Asp Asp Thr Lys Leu Tyr Ile Tyr Phe Lys Thr
    50                  55                  60 cgt ttt tct aat tac att aaa gat gtt ttg cgt cag caa gaa agt cag          240
Arg Phe Ser Asn Tyr Ile Lys Asp Val Leu Arg Gln Gln Glu Ser Gln
65                  70                  75                  80 aaa cgt cgt ttt aat aga atg tct tat gaa gaa gtc ggt gag att gaa          288
Lys Arg Arg Phe Asn Arg Met Ser Tyr Glu Glu Val Gly Glu Ile Glu
                85                  90                  95 cac tgt ttg tca agt ggc ggt atg caa ttg gat gaa tat att tta ttt          336
His Cys Leu Ser Ser Gly Gly Met Gln Leu Asp Glu Tyr Ile Leu Phe
            100                 105                 110 cgt gat agt ttg ctt gca tat aaa caa ggt ctg agt act gaa aag caa          384
Arg Asp Ser Leu Leu Ala Tyr Lys Gln Gly Leu Ser Thr Glu Lys Gln
        115                 120                 125 gag ctg ttt gag cgc ttg gta gca ggagagcact ttttgggaag gcaaagtatg        438
Glu Leu Phe Glu Arg Leu Val Ala
    130                 135 ctgaaagatt tacgtaaaaa attaagtgat tttaaggaaa aa                           480
```

<210> SEQ ID NO 23
<211> LENGTH: 136
<212> TYPE: PRT
<213> ORGANISM: Streptococcus mutans

<400> SEQUENCE: 23

```
Met Glu Glu Asp Phe Glu Ile Val Phe Asn Lys Val Lys Pro Ile Val
1               5                   10                  15

Trp Lys Leu Ser Arg Tyr Tyr Phe Ile Lys Met Trp Thr Arg Glu Asp
            20                  25                  30
```

```
Trp Gln Gln Glu Gly Met Leu Ile Leu His Gln Leu Leu Arg Glu His
        35                  40                  45

Pro Glu Leu Glu Glu Asp Asp Thr Lys Leu Tyr Ile Tyr Phe Lys Thr
 50                  55                  60

Arg Phe Ser Asn Tyr Ile Lys Asp Val Leu Arg Gln Gln Glu Ser Gln
 65                  70                  75                  80

Lys Arg Arg Phe Asn Arg Met Ser Tyr Glu Glu Val Gly Glu Ile Glu
                 85                  90                  95

His Cys Leu Ser Ser Gly Gly Met Gln Leu Asp Glu Tyr Ile Leu Phe
            100                 105                 110

Arg Asp Ser Leu Leu Ala Tyr Lys Gln Gly Leu Ser Thr Glu Lys Gln
            115                 120                 125

Glu Leu Phe Glu Arg Leu Val Ala
        130                 135

<210> SEQ ID NO 24
<211> LENGTH: 680
<212> TYPE: DNA
<213> ORGANISM: Streptococcus mutans
<220> FEATURE:
<221> NAME/KEY: misc_feature
<222> LOCATION: (1)..(680)

<400> SEQUENCE: 24
gtaaataaaa cagccagtta agatgggaca tttatgtcct gttcttaaag tctttttcgt      60
tttataataa ttttattata aaaggaggtc atcgtaatag atggaagaag attttgaaat     120
tgtttttaat aaggttaagc caattgtatg gaaattaagc cgttattact ttattaaaat     180
gtggactcgt gaagattggc aacaagaggg aatgttgatt ttgcaccaat tattaaggga     240
acatccagaa ttagaagagg atgatacaaa attgtatatc tattttaaga cacgtttttc     300
taattacatt aaagatgttt tgcgtcagca agaaagtcag aaacgtcgtt ttaatagaat     360
gtcttatgaa gaagtcggtg agattgaaca ctgtttgtca gtggcggta tgcaattgga     420 tgaatatatt ttatttcgtg atagtttgct tgcatataaa caaggtctga gtactgaaaa     480
gcaagagctg tttgagcgct tggtagcagg agagcacttt ttgggaaggc aaagtatgct     540
gaaagattta cgtaaaaaat taagtgattt taaggaaaaa tagttaaaaa gggaaagaat     600
ggaacatgtg attgtaccat tctttttggt tgaaaattaa gaaaagttat tataaattat     660
tggtttaaca tgccatatta                                                 680

<210> SEQ ID NO 25
<211> LENGTH: 2280
<212> TYPE: DNA
<213> ORGANISM: Streptococcus mutans
<220> FEATURE:
<221> NAME/KEY: CDS
<222> LOCATION: (1)..(2280)

<400> SEQUENCE: 25 atg aaa caa gtt att tat gtt gtt tta atc gtc ata gcc gtt aac att       48
Met Lys Gln Val Ile Tyr Val Val Leu Ile Val Ile Ala Val Asn Ile
  1               5                  10                  15 ctc tta gag att atc aaa aga gta aca aaa agg gga ggg aca gtt tcg       96
Leu Leu Glu Ile Ile Lys Arg Val Thr Lys Arg Gly Gly Thr Val Ser
             20                  25                  30 tca tct aat cct tta cca gat ggg cag tct aag ttg ttt tgg cgc aga      144
Ser Ser Asn Pro Leu Pro Asp Gly Gln Ser Lys Leu Phe Trp Arg Arg
         35                  40                  45
```

-continued

| | |
|---|---|
| cat tat aag cta gta cct cag att gat acc aga gac tgt ggg ccg gca<br>His Tyr Lys Leu Val Pro Gln Ile Asp Thr Arg Asp Cys Gly Pro Ala<br> 50                       55                   60 | 192 |
| gtg ctg gca tct gtt gca aag cat tac gga tct aat tac tct atc gct<br>Val Leu Ala Ser Val Ala Lys His Tyr Gly Ser Asn Tyr Ser Ile Ala<br>65                    70                   75                   80 | 240 |
| tat ctg cgg gaa ctc tca aag act aac aag cag gga aca aca gct ctt<br>Tyr Leu Arg Glu Leu Ser Lys Thr Asn Lys Gln Gly Thr Thr Ala Leu<br>                  85                   90                   95 | 288 |
| ggc att gtt gaa gct gct aaa aag tta ggc ttt gaa aca cgc tct atc<br>Gly Ile Val Glu Ala Ala Lys Lys Leu Gly Phe Glu Thr Arg Ser Ile<br>               100                  105                110 | 336 |
| aag gcg gat atg acg ctt ttt gat tat aat gat ttg acc tat cct ttt<br>Lys Ala Asp Met Thr Leu Phe Asp Tyr Asn Asp Leu Thr Tyr Pro Phe<br>             115                  120                125 | 384 |
| atc gtc cat gtg att aaa gga aaa cgt ctg cag cat tat tat gtc gtc<br>Ile Val His Val Ile Lys Gly Lys Arg Leu Gln His Tyr Tyr Val Val<br>130                    135                  140 | 432 |
| tat ggc agc cag aat aat cag ctg att att gga gat cct gat cct tca<br>Tyr Gly Ser Gln Asn Asn Gln Leu Ile Ile Gly Asp Pro Asp Pro Ser<br>145                  150                  155                160 | 480 |
| gtt aag gtg act agg atg agt aag gaa cgc ttt caa tca gag tgg aca<br>Val Lys Val Thr Arg Met Ser Lys Glu Arg Phe Gln Ser Glu Trp Thr<br>                  165                170                175 | 528 |
| ggc ctt gca att ttc cta gct cct cag cct aac tat aag cct cat aaa<br>Gly Leu Ala Ile Phe Leu Ala Pro Gln Pro Asn Tyr Lys Pro His Lys<br>             180                  185                190 | 576 |
| ggt gaa aaa aat ggt ttg tct aat ttc ttc ccg ttg atc ttt aag cag<br>Gly Glu Lys Asn Gly Leu Ser Asn Phe Phe Pro Leu Ile Phe Lys Gln<br>             195                  200                205 | 624 |
| aaa gct ttg atg act tat att atc ata gct agc ttg att gtg acg ctc<br>Lys Ala Leu Met Thr Tyr Ile Ile Ile Ala Ser Leu Ile Val Thr Leu<br>210                    215                  220 | 672 |
| att gat att gtc gga tca tac tat ctc caa gga ata ttg gac gag tac<br>Ile Asp Ile Val Gly Ser Tyr Tyr Leu Gln Gly Ile Leu Asp Glu Tyr<br>225                  230                  235                240 | 720 |
| att cct gat cag ctg att tca act tta gga atg att acg att ggt ctg<br>Ile Pro Asp Gln Leu Ile Ser Thr Leu Gly Met Ile Thr Ile Gly Leu<br>             245                  250                255 | 768 |
| ata ata acc tat att atc cag cag gtc atg gct ttt gca aaa gaa tac<br>Ile Ile Thr Tyr Ile Ile Gln Gln Val Met Ala Phe Ala Lys Glu Tyr<br>             260                  265                270 | 816 |
| ctc ttg gcc gta ctc agt ttg cgt tta gtc att gat gtt atc ctg tct<br>Leu Leu Ala Val Leu Ser Leu Arg Leu Val Ile Asp Val Ile Leu Ser<br>             275                  280                285 | 864 |
| tat atc aaa cat att ttt acg ctt cct atg tct ttc ttt gcg aca agg<br>Tyr Ile Lys His Ile Phe Thr Leu Pro Met Ser Phe Phe Ala Thr Arg<br>290                    295                  300 | 912 |
| cga aca gga gaa atc acg tct cgt ttt aca gat gcc aat cag att att<br>Arg Thr Gly Glu Ile Thr Ser Arg Phe Thr Asp Ala Asn Gln Ile Ile<br>305                  310                  315                320 | 960 |
| gat gct gta gcg tca acc atc ttt tca atc ttt tta gat atg act atg<br>Asp Ala Val Ala Ser Thr Ile Phe Ser Ile Phe Leu Asp Met Thr Met<br>             325                  330                335 | 1008 |
| gta att ttg gtt ggt ggg gtt ttg ttg gcg caa aac aat aac ctt ttc<br>Val Ile Leu Val Gly Gly Val Leu Leu Ala Gln Asn Asn Asn Leu Phe<br>             340                  345                350 | 1056 |
| ttt cta acc ttg ctc tcc att ccg att tat gcc atc att att ttt gct<br>Phe Leu Thr Leu Leu Ser Ile Pro Ile Tyr Ala Ile Ile Ile Phe Ala<br>             355                  360                365 | 1104 |

```
ttc ttg aaa ccc ttt gag aaa atg aat cac gaa gtg atg gaa agc aat      1152
Phe Leu Lys Pro Phe Glu Lys Met Asn His Glu Val Met Glu Ser Asn
        370                 375                 380 gct gtg gta agt tct tct atc att gaa gat atc aat ggg atg gaa acc      1200
Ala Val Val Ser Ser Ser Ile Ile Glu Asp Ile Asn Gly Met Glu Thr
385                 390                 395                 400 att aaa tca ctc aca agt gag tcc gct cgt tat caa aac att gat agt      1248
Ile Lys Ser Leu Thr Ser Glu Ser Ala Arg Tyr Gln Asn Ile Asp Ser
                405                 410                 415 gaa ttt gtt gat tat ttg gag aaa aac ttt aag cta cac aag tat agt      1296
Glu Phe Val Asp Tyr Leu Glu Lys Asn Phe Lys Leu His Lys Tyr Ser
            420                 425                 430 gcc att caa acc gca tta aaa agc ggt gct aag ctt atc ctc aat gtt      1344
Ala Ile Gln Thr Ala Leu Lys Ser Gly Ala Lys Leu Ile Leu Asn Val
        435                 440                 445 gtc att ctc tgg tat ggc tct cgt cta gtt atg gat aat aaa atc tca      1392
Val Ile Leu Trp Tyr Gly Ser Arg Leu Val Met Asp Asn Lys Ile Ser
450                 455                 460 gtt ggt cag ctt atc acc ttt aat gct ttg ctg tct tat ttc tca aat      1440
Val Gly Gln Leu Ile Thr Phe Asn Ala Leu Leu Ser Tyr Phe Ser Asn
465                 470                 475                 480 cca att gaa aat att atc aat ctg caa tcc aaa ctg cag tca gct cgc      1488
Pro Ile Glu Asn Ile Ile Asn Leu Gln Ser Lys Leu Gln Ser Ala Arg
                485                 490                 495 gtt gcc aat aca cgt ctt aat gag gtc tat ctt gtc gaa tct gaa ttt      1536
Val Ala Asn Thr Arg Leu Asn Glu Val Tyr Leu Val Glu Ser Glu Phe
            500                 505                 510 gaa aaa gac ggc gat tta tca gaa aat agc ttt tta gat ggt gat att      1584
Glu Lys Asp Gly Asp Leu Ser Glu Asn Ser Phe Leu Asp Gly Asp Ile
        515                 520                 525 tcg ttt gaa aat ctt tct tat aaa tat gga ttt ggg cga gat acc tta      1632
Ser Phe Glu Asn Leu Ser Tyr Lys Tyr Gly Phe Gly Arg Asp Thr Leu
    530                 535                 540 tca gat att aat tta tca atc aaa aaa ggc tcc aag gtc agt cta gtt      1680
Ser Asp Ile Asn Leu Ser Ile Lys Lys Gly Ser Lys Val Ser Leu Val
545                 550                 555                 560 gga gcc agt ggt tct ggt aaa aca act ttg gct aaa ctg att gtc aat      1728
Gly Ala Ser Gly Ser Gly Lys Thr Thr Leu Ala Lys Leu Ile Val Asn
                565                 570                 575 ttc tac gag cct aac aag ggg att gtt cga atc aat ggc aat gat tta      1776
Phe Tyr Glu Pro Asn Lys Gly Ile Val Arg Ile Asn Gly Asn Asp Leu
            580                 585                 590 aaa gtt att gat aag aca gct ttg cgg cgg cat att agc tat ttg ccg      1824
Lys Val Ile Asp Lys Thr Ala Leu Arg Arg His Ile Ser Tyr Leu Pro
        595                 600                 605 caa cag gcc tat gtt ttt agt ggc tct att atg gat aat ctc gtt tta      1872
Gln Gln Ala Tyr Val Phe Ser Gly Ser Ile Met Asp Asn Leu Val Leu
    610                 615                 620 gga gct aaa gaa gga acg agt cag gaa gac att att cgt gct tgt gaa      1920
Gly Ala Lys Glu Gly Thr Ser Gln Glu Asp Ile Ile Arg Ala Cys Glu
625                 630                 635                 640 att gct gaa atc cgc tcg gac att gaa caa atg cct cag ggc tat cag      1968
Ile Ala Glu Ile Arg Ser Asp Ile Glu Gln Met Pro Gln Gly Tyr Gln
                645                 650                 655 aca gag tta tca gat ggt gcc ggt att tct ggc ggt caa aaa cag cgg      2016
Thr Glu Leu Ser Asp Gly Ala Gly Ile Ser Gly Gly Gln Lys Gln Arg
            660                 665                 670 att gct tta gct agg gcc tta tta aca cag gca ccg gtt ttg att ctg      2064
Ile Ala Leu Ala Arg Ala Leu Leu Thr Gln Ala Pro Val Leu Ile Leu
        675                 680                 685
```

```
gat gaa gcc acc agc agt ctt gat att ttg aca gaa aag aaa att atc      2112
Asp Glu Ala Thr Ser Ser Leu Asp Ile Leu Thr Glu Lys Lys Ile Ile
    690                 695                 700 agc aat ctc tta cag atg acg gag aaa aca ata att ttt gtt gcc cac      2160
Ser Asn Leu Leu Gln Met Thr Glu Lys Thr Ile Ile Phe Val Ala His
705                 710                 715                 720 cgc tta agc att tca cag cgt act gac gaa gtc att gtc atg gat cag      2208
Arg Leu Ser Ile Ser Gln Arg Thr Asp Glu Val Ile Val Met Asp Gln
                725                 730                 735 gga aaa att gtt gaa caa ggc act cat aag gaa ctt tta gct aag caa      2256
Gly Lys Ile Val Glu Gln Gly Thr His Lys Glu Leu Leu Ala Lys Gln
            740                 745                 750 ggt ttc tat tat aac ctg ttt aat                                       2280
Gly Phe Tyr Tyr Asn Leu Phe Asn
                755                 760

<210> SEQ ID NO 26
<211> LENGTH: 760
<212> TYPE: PRT
<213> ORGANISM: Streptococcus mutans

<400> SEQUENCE: 26

Met Lys Gln Val Ile Tyr Val Val Leu Ile Val Ile Ala Val Asn Ile
1               5                   10                  15

Leu Leu Glu Ile Ile Lys Arg Val Thr Lys Arg Gly Gly Thr Val Ser
            20                  25                  30

Ser Ser Asn Pro Leu Pro Asp Gly Gln Ser Lys Leu Phe Trp Arg Arg
        35                  40                  45

His Tyr Lys Leu Val Pro Gln Ile Asp Thr Arg Asp Cys Gly Pro Ala
    50                  55                  60

Val Leu Ala Ser Val Ala Lys His Tyr Gly Ser Asn Tyr Ser Ile Ala
65                  70                  75                  80

Tyr Leu Arg Glu Leu Ser Lys Thr Asn Lys Gln Gly Thr Thr Ala Leu
                85                  90                  95

Gly Ile Val Glu Ala Ala Lys Lys Leu Gly Phe Glu Thr Arg Ser Ile
            100                 105                 110

Lys Ala Asp Met Thr Leu Phe Asp Tyr Asn Asp Leu Thr Tyr Pro Phe
        115                 120                 125

Ile Val His Val Ile Lys Gly Lys Arg Leu Gln His Tyr Tyr Val Val
    130                 135                 140

Tyr Gly Ser Gln Asn Asn Gln Leu Ile Ile Gly Asp Pro Asp Pro Ser
145                 150                 155                 160

Val Lys Val Thr Arg Met Ser Lys Glu Arg Phe Gln Ser Glu Trp Thr
                165                 170                 175

Gly Leu Ala Ile Phe Leu Ala Pro Gln Pro Asn Tyr Lys Pro His Lys
            180                 185                 190

Gly Glu Lys Asn Gly Leu Ser Asn Phe Phe Pro Leu Ile Phe Lys Gln
        195                 200                 205

Lys Ala Leu Met Thr Tyr Ile Ile Ala Ser Leu Ile Val Thr Leu
    210                 215                 220

Ile Asp Ile Val Gly Ser Tyr Tyr Leu Gln Gly Ile Leu Asp Glu Tyr
225                 230                 235                 240

Ile Pro Asp Gln Leu Ile Ser Thr Leu Gly Met Ile Thr Ile Gly Leu
                245                 250                 255

Ile Ile Thr Tyr Ile Ile Gln Gln Val Met Ala Phe Ala Lys Glu Tyr
            260                 265                 270
```

-continued

```
Leu Leu Ala Val Leu Ser Leu Arg Leu Val Ile Asp Val Ile Leu Ser
            275                 280                 285

Tyr Ile Lys His Ile Phe Thr Leu Pro Met Ser Phe Phe Ala Thr Arg
        290                 295                 300

Arg Thr Gly Glu Ile Thr Ser Arg Phe Thr Asp Ala Asn Gln Ile Ile
305                 310                 315                 320

Asp Ala Val Ala Ser Thr Ile Phe Ser Ile Phe Leu Asp Met Thr Met
                325                 330                 335

Val Ile Leu Val Gly Val Leu Leu Ala Gln Asn Asn Asn Leu Phe
            340                 345                 350

Phe Leu Thr Leu Leu Ser Ile Pro Ile Tyr Ala Ile Ile Phe Ala
        355                 360                 365

Phe Leu Lys Pro Phe Glu Lys Met Asn His Glu Val Met Glu Ser Asn
        370                 375                 380

Ala Val Val Ser Ser Ile Ile Glu Asp Ile Asn Gly Met Glu Thr
385                 390                 395                 400

Ile Lys Ser Leu Thr Ser Glu Ser Ala Arg Tyr Gln Asn Ile Asp Ser
                405                 410                 415

Glu Phe Val Asp Tyr Leu Glu Lys Asn Phe Lys Leu His Lys Tyr Ser
            420                 425                 430

Ala Ile Gln Thr Ala Leu Lys Ser Gly Ala Lys Leu Ile Leu Asn Val
        435                 440                 445

Val Ile Leu Trp Tyr Gly Ser Arg Leu Val Met Asp Asn Lys Ile Ser
450                 455                 460

Val Gly Gln Leu Ile Thr Phe Asn Ala Leu Leu Ser Tyr Phe Ser Asn
465                 470                 475                 480

Pro Ile Glu Asn Ile Ile Asn Leu Gln Ser Lys Leu Gln Ser Ala Arg
                485                 490                 495

Val Ala Asn Thr Arg Leu Asn Glu Val Tyr Leu Val Glu Ser Glu Phe
            500                 505                 510

Glu Lys Asp Gly Asp Leu Ser Glu Asn Ser Phe Leu Asp Gly Asp Ile
        515                 520                 525

Ser Phe Glu Asn Leu Ser Tyr Lys Tyr Gly Phe Gly Arg Asp Thr Leu
        530                 535                 540

Ser Asp Ile Asn Leu Ser Ile Lys Lys Gly Ser Lys Val Ser Leu Val
545                 550                 555                 560

Gly Ala Ser Gly Ser Gly Lys Thr Thr Leu Ala Lys Leu Ile Val Asn
                565                 570                 575

Phe Tyr Glu Pro Asn Lys Gly Ile Val Arg Ile Asn Gly Asn Asp Leu
            580                 585                 590

Lys Val Ile Asp Lys Thr Ala Leu Arg Arg His Ile Ser Tyr Leu Pro
        595                 600                 605

Gln Gln Ala Tyr Val Phe Ser Gly Ser Ile Met Asp Asn Leu Val Leu
        610                 615                 620

Gly Ala Lys Glu Gly Thr Ser Gln Glu Asp Ile Ile Arg Ala Cys Glu
625                 630                 635                 640

Ile Ala Glu Ile Arg Ser Asp Ile Glu Gln Met Pro Gln Gly Tyr Gln
                645                 650                 655

Thr Glu Leu Ser Asp Gly Ala Gly Ile Ser Gly Gly Gln Lys Gln Arg
            660                 665                 670

Ile Ala Leu Ala Arg Ala Leu Leu Thr Gln Ala Pro Val Leu Ile Leu
        675                 680                 685
```

```
Asp Glu Ala Thr Ser Ser Leu Asp Ile Leu Thr Glu Lys Lys Ile Ile
        690                 695                 700
Ser Asn Leu Leu Gln Met Thr Glu Lys Thr Ile Ile Phe Val Ala His
705                 710                 715                 720
Arg Leu Ser Ile Ser Gln Arg Thr Asp Glu Val Ile Val Met Asp Gln
                725                 730                 735
Gly Lys Ile Val Glu Gln Gly Thr His Lys Glu Leu Leu Ala Lys Gln
                740                 745                 750
Gly Phe Tyr Tyr Asn Leu Phe Asn
            755                 760

<210> SEQ ID NO 27
<211> LENGTH: 900
<212> TYPE: DNA
<213> ORGANISM: Streptococcus mutans
<220> FEATURE:
<221> NAME/KEY: CDS
<222> LOCATION: (1)..(900)

<400> SEQUENCE: 27 atg gat cct aaa ttt tta caa agt gca gaa ttt tat agg aga cgc tat       48
Met Asp Pro Lys Phe Leu Gln Ser Ala Glu Phe Tyr Arg Arg Arg Tyr
1               5                   10                  15 cat aat ttt gcg aca cta tta att gtt cct ttg gtc tgc ttg att atc       96
His Asn Phe Ala Thr Leu Leu Ile Val Pro Leu Val Cys Leu Ile Ile
            20                  25                  30 ttc ttg gtc ata ttc ctt tgt ttt gct aaa aaa gaa att aca gtg att      144
Phe Leu Val Ile Phe Leu Cys Phe Ala Lys Lys Glu Ile Thr Val Ile
        35                  40                  45 tct act ggt gaa gtt gca cca aca aag gtt gta gat gtt atc caa tct      192
Ser Thr Gly Glu Val Ala Pro Thr Lys Val Val Asp Val Ile Gln Ser
50                  55                  60 tac agt gac agt tca atc att aaa aat aat tta gat aat aat gca gct      240
Tyr Ser Asp Ser Ser Ile Ile Lys Asn Asn Leu Asp Asn Asn Ala Ala
65                  70                  75                  80 gtt gag aag gga gac gtt tta att gaa tat tca gaa aat gcc agt cca      288
Val Glu Lys Gly Asp Val Leu Ile Glu Tyr Ser Glu Asn Ala Ser Pro
                85                  90                  95 aac cgt cag act gaa caa aag aat att ata aaa gaa aga caa aaa cga      336
Asn Arg Gln Thr Glu Gln Lys Asn Ile Ile Lys Glu Arg Gln Lys Arg
            100                 105                 110 gaa gag aag gaa aag aaa aaa cac caa aag agc aag aaa aag aag aag      384
Glu Glu Lys Glu Lys Lys Lys His Gln Lys Ser Lys Lys Lys Lys Lys
        115                 120                 125 tct aag agc aag aaa gct tcc aaa gat aag aaa aag aaa tcg aaa gac      432
Ser Lys Ser Lys Lys Ala Ser Lys Asp Lys Lys Lys Lys Ser Lys Asp
    130                 135                 140 aag gaa agc agc tct gac gat gaa aat gag aca aaa aag gtt tcg att      480
Lys Glu Ser Ser Ser Asp Asp Glu Asn Glu Thr Lys Lys Val Ser Ile
145                 150                 155                 160 ttt gct tca gaa gat ggt att att cat acc aat ccc aaa tat gat ggt      528
Phe Ala Ser Glu Asp Gly Ile Ile His Thr Asn Pro Lys Tyr Asp Gly
                165                 170                 175 gcc aat att att ccg aag caa acc gag att gct caa atc tat cct gat      576
Ala Asn Ile Ile Pro Lys Gln Thr Glu Ile Ala Gln Ile Tyr Pro Asp
            180                 185                 190 att caa aaa aca aga aaa gtg tta atc acc tat tat gct tct tct gat      624
Ile Gln Lys Thr Arg Lys Val Leu Ile Thr Tyr Tyr Ala Ser Ser Asp
        195                 200                 205
```

```
gat gtt gtt tct atg aaa aag ggg caa acc gct cgt ctt tcc ttg gaa      672
Asp Val Val Ser Met Lys Lys Gly Gln Thr Ala Arg Leu Ser Leu Glu
    210             215                 220 aaa aag gga aat gac aag gtt gtt att gaa gga aaa att aac aat gtc      720
Lys Lys Gly Asn Asp Lys Val Val Ile Glu Gly Lys Ile Asn Asn Val
225                 230                 235                 240 gct tca tca gca act act act aaa aaa gga aat ctc ttt aag gtt act      768
Ala Ser Ser Ala Thr Thr Thr Lys Lys Gly Asn Leu Phe Lys Val Thr
                245                 250                 255 gcc aaa gta aag gtt tct aag aaa aat agc aaa ctc atc aag tat ggt      816
Ala Lys Val Lys Val Ser Lys Lys Asn Ser Lys Leu Ile Lys Tyr Gly
            260                 265                 270 atg aca ggc aag aca gtc act gtc att gat aaa aag act tat ttt gat      864
Met Thr Gly Lys Thr Val Thr Val Ile Asp Lys Lys Thr Tyr Phe Asp
        275                 280                 285 tat ttc aaa gat aaa tta ctg cat aaa atg gat aat                      900
Tyr Phe Lys Asp Lys Leu Leu His Lys Met Asp Asn
    290                 295                 300

<210> SEQ ID NO 28
<211> LENGTH: 300
<212> TYPE: PRT
<213> ORGANISM: Streptococcus mutans

<400> SEQUENCE: 28

Met Asp Pro Lys Phe Leu Gln Ser Ala Glu Phe Tyr Arg Arg Tyr
1               5                   10                  15

His Asn Phe Ala Thr Leu Leu Ile Val Pro Leu Val Cys Leu Ile Ile
                20                  25                  30

Phe Leu Val Ile Phe Leu Cys Phe Ala Lys Lys Glu Ile Thr Val Ile
            35                  40                  45

Ser Thr Gly Glu Val Ala Pro Thr Lys Val Val Asp Val Ile Gln Ser
    50                  55                  60

Tyr Ser Asp Ser Ser Ile Ile Lys Asn Asn Leu Asp Asn Asn Ala Ala
65                  70                  75                  80

Val Glu Lys Gly Asp Val Leu Ile Glu Tyr Ser Glu Asn Ala Ser Pro
                85                  90                  95

Asn Arg Gln Thr Glu Gln Lys Asn Ile Ile Lys Glu Arg Gln Lys Arg
                100                 105                 110

Glu Glu Lys Glu Lys Lys His Gln Lys Ser Lys Lys Lys Lys Lys
            115                 120                 125

Ser Lys Ser Lys Lys Ala Ser Lys Asp Lys Lys Lys Ser Lys Asp
    130                 135                 140

Lys Glu Ser Ser Ser Asp Asp Glu Asn Glu Thr Lys Lys Val Ser Ile
145                 150                 155                 160

Phe Ala Ser Glu Asp Gly Ile Ile His Thr Asn Pro Lys Tyr Asp Gly
                165                 170                 175

Ala Asn Ile Ile Pro Lys Gln Thr Glu Ile Ala Gln Ile Tyr Pro Asp
                180                 185                 190

Ile Gln Lys Thr Arg Lys Val Leu Ile Thr Tyr Tyr Ala Ser Ser Asp
            195                 200                 205

Asp Val Val Ser Met Lys Lys Gly Gln Thr Ala Arg Leu Ser Leu Glu
    210                 215                 220

Lys Lys Gly Asn Asp Lys Val Val Ile Glu Gly Lys Ile Asn Asn Val
225                 230                 235                 240

Ala Ser Ser Ala Thr Thr Thr Lys Lys Gly Asn Leu Phe Lys Val Thr
                245                 250                 255
```

```
Ala Lys Val Lys Val Ser Lys Lys Asn Ser Lys Leu Ile Lys Tyr Gly
            260                 265                 270

Met Thr Gly Lys Thr Val Thr Val Ile Asp Lys Lys Thr Tyr Phe Asp
            275                 280                 285

Tyr Phe Lys Asp Lys Leu Leu His Lys Met Asp Asn
            290             295                 300
```

We claim:

1. A composition comprising a peptide analog of SEQ ID NO:11, wherein the peptide analog is SEQ ID NO:48.

2. The composition of claim 1 further comprising at least one other inhibitor of SEQ ID NO: 11.

3. The composition of claim 2 wherein the other inhibitor of SEQ ID NO: 11 is an antibody specific for SEQ ID NO: 11.

4. The composition of claim 3 wherein the antibody is a monoclonal antibody.

5. The composition of claim 2 wherein the other inhibitor of SEQ ID NO: 11 is SEQ ID NO: 41, SEQ ID NO: 42, SEQ ID NO: 43, SEQ ID NO: 49, SEQ ID NO: 50, SEQ ID NO: 51, or a combination thereof.

6. The composition of claim 1 further comprising an antibiotic.

7. The composition of claim 2 further comprising an antibiotic.

8. The composition of claim 1 further comprising an antioxidant.

9. The composition of claim 2 further comprising an antioxidant.

10. The composition of claim 1, wherein the composition is toothpaste, mouthwash, food, food additive, dental floss, or chewing gum.

11. The composition of claim 2, wherein the composition is toothpaste, mouthwash, food, food additive, dental floss, or chewing gum.

12. The composition of claim 1, wherein SEQ ID NO:48 is coupled to a lipid, a carbohydrate, or a polymer.

13. The composition of claim 2, wherein SEQ ID NO:48 is coupled to a lipid, a carbohydrate, or a polymer.

14. The composition of claim 5, wherein SEQ ID NO: 41, SEQ ID NO: 42, SEQ ID NO: 43, SEQ ID NO: 49, SEQ ID NO: 50, SEQ ID NO: 51, or a combination thereof is coupled to a lipid, a carbohydrate, or a polymer.

15. A method of treating caries comprising administering a composition of claim 1.

* * * * *

UNITED STATES PATENT AND TRADEMARK OFFICE
CERTIFICATE OF CORRECTION

| | |
|---|---|
| PATENT NO. | : 7,597,895 B2 |
| APPLICATION NO. | : 11/005636 |
| DATED | : October 6, 2009 |
| INVENTOR(S) | : Huang et al. |

It is certified that error appears in the above-identified patent and that said Letters Patent is hereby corrected as shown below:

Col. 29-64: This sequence listing should be replaced with the sequence listing included with the March 26, 2008 amendment, as shown on the attached pages.

SEQUENCE LISTING

<110> Cvitkovitch, Dennis

<120> SIGNAL PEPTIDES, NUCLEIC ACID MOLECULES AND METHODS FOR TREATMENT OF CARIES

<130> 60327.7USI1

<140> 11/005,636
<141> 2004-12-06

<150> 60/269,949
<151> 2001-02-20

<150> 09/833,017
<151> 2001-04-10

<160> 57

<170> PatentIn version 3.4

<210> 1
<211> 46
<212> PRT
<213> Streptococcus mutans

<400> 1

Met Lys Lys Thr Leu Ser Leu Lys Asn Asp Phe Lys Glu Ile Lys Thr
1               5                   10                  15

Asp Glu Leu Glu Ile Ile Ile Gly Gly Ser Gly Ser Leu Ser Thr Phe
                20                  25                  30

Phe Arg Leu Phe Asn Arg Ser Phe Thr Gln Ala Leu Gly Lys
                35                  40                  45

<210> 2
<211> 441
<212> PRT
<213> Staphylococcus mutans

<400> 2

Met Asn Glu Ala Leu Met Ile Leu Ser Asn Gly Leu Leu Thr Tyr Leu
1               5                   10                  15

Thr Val Leu Phe Leu Leu Phe Leu Phe Ser Lys Val Ser Asn Val Thr
                20                  25                  30

Leu Ser Lys Lys Glu Leu Thr Leu Phe Ser Ile Ser Asn Phe Leu Ile
                35                  40                  45

```
Met Ile Ala Val Thr Met Val Asn Val Asn Leu Phe Tyr Pro Ala Glu
     50                  55                  60

Pro Leu Tyr Phe Ile Ala Leu Ser Ile Tyr Leu Asn Arg Gln Asn Ser
65                  70                  75                  80

Leu Ser Leu Asn Ile Phe Tyr Gly Leu Leu Pro Val Ala Ser Ser Asp
                 85                  90                  95

Leu Phe Arg Arg Ala Ile Ile Phe Phe Ile Leu Asp Gly Thr Gln Gly
             100                 105                 110

Ile Val Met Gly Ser Ser Ile Ile Thr Thr Tyr Met Ile Glu Phe Ala
         115                 120                 125

Gly Ile Ala Leu Ser Tyr Leu Phe Leu Ser Val Phe Asn Val Asp Ile
    130                 135                 140

Gly Arg Leu Lys Asp Ser Leu Thr Lys Met Lys Val Lys Lys Arg Leu
145                 150                 155                 160

Ile Pro Met Asn Ile Thr Met Leu Leu Tyr Tyr Leu Leu Ile Gln Val
                165                 170                 175

Leu Tyr Val Ile Glu Ser Tyr Asn Val Ile Pro Thr Leu Lys Phe Arg
             180                 185                 190

Lys Phe Val Val Ile Val Tyr Leu Ile Leu Phe Leu Ile Leu Ile Ser
         195                 200                 205

Phe Leu Ser Gln Tyr Thr Lys Gln Lys Val Gln Asn Glu Ile Met Ala
    210                 215                 220

Gln Lys Glu Ala Gln Ile Arg Asn Ile Thr Gln Tyr Ser Gln Gln Ile
225                 230                 235                 240

Glu Ser Leu Tyr Lys Asp Ile Arg Ser Phe Arg His Asp Tyr Leu Asn
                245                 250                 255

Ile Leu Thr Ser Leu Arg Leu Gly Ile Glu Asn Lys Asp Leu Ala Ser
             260                 265                 270

Ile Glu Lys Ile Tyr His Gln Ile Leu Glu Lys Thr Gly His Gln Leu
         275                 280                 285
```

```
Gln Asp Thr Arg Tyr Asn Ile Gly His Leu Ala Asn Ile Gln Asn Asp
    290                 295                 300

Ala Val Lys Gly Ile Leu Ser Ala Lys Ile Leu Glu Ala Gly Asn Lys
305                 310                 315                 320

Lys Ile Ala Val Asn Val Glu Val Ser Ser Lys Ile Gln Leu Pro Glu
                325                 330                 335

Met Glu Leu Leu Asp Phe Ile Thr Ile Leu Ser Ile Leu Cys Asp Asn
            340                 345                 350

Ala Ile Glu Ala Ala Phe Glu Ser Leu Asn Pro Glu Ile Gln Leu Ala
        355                 360                 365

Phe Phe Lys Lys Asn Gly Ser Ile Val Phe Ile Ile Gln Asn Ser Thr
    370                 375                 380

Lys Glu Lys Gln Ile Asp Val Ser Lys Ile Phe Lys Glu Asn Tyr Ser
385                 390                 395                 400

Thr Lys Gly Ser Asn Arg Gly Ile Gly Leu Ala Lys Val Asn His Ile
                405                 410                 415

Leu Glu His Tyr Pro Lys Thr Ser Leu Gln Thr Ser Asn His His His
            420                 425                 430

Leu Phe Lys Gln Leu Leu Ile Ile Lys
        435                 440

<210> 3
<211> 250
<212> PRT
<213> Staphylococcus mutans

<400> 3

Met Ile Ser Ile Phe Val Leu Glu Asp Asp Phe Leu Gln Gln Gly Arg
1               5                   10                  15

Leu Glu Thr Thr Ile Ala Ala Ile Met Lys Glu Lys Asn Trp Ser Tyr
            20                  25                  30

Lys Glu Leu Thr Ile Phe Gly Lys Pro Gln Gln Leu Ile Asp Ala Ile
        35                  40                  45

Pro Glu Lys Gly Asn His Gln Ile Phe Phe Leu Asp Ile Glu Ile Lys
```

```
                    50                      55                      60

Lys Glu Glu Lys Lys Gly Leu Glu Val Ala Asn Gln Ile Arg Gln His
         65              70                  75                  80

Asn Pro Ser Ala Val Ile Val Phe Val Thr Thr His Ser Glu Phe Met
                         85                  90                  95

Pro Leu Thr Phe Gln Tyr Gln Val Ser Ala Leu Asp Phe Ile Asp Lys
                        100                 105                 110

Ser Leu Asn Pro Glu Glu Phe Ser His Arg Ile Glu Ser Ala Leu Tyr
                    115                 120                 125

Tyr Ala Met Glu Asn Ser Gln Lys Asn Gly Gln Ser Glu Glu Leu Phe
                130                 135                 140

Ile Phe His Ser Ser Glu Thr Gln Phe Gln Val Pro Phe Ala Glu Ile
        145                 150                 155                 160

Leu Tyr Phe Glu Thr Ser Ser Thr Ala His Lys Leu Cys Leu Tyr Thr
                        165                 170                 175

Tyr Asp Glu Arg Ile Glu Phe Tyr Gly Ser Met Thr Asp Ile Val Lys
                    180                 185                 190

Met Asp Lys Arg Leu Phe Gln Cys His Arg Ser Phe Ile Val Asn Pro
                195                 200                 205

Ala Asn Ile Thr Arg Ile Asp Arg Lys Lys Arg Leu Ala Tyr Phe Arg
        210                 215                 220

Asn Asn Lys Ser Cys Leu Ile Ser Arg Thr Lys Leu Thr Lys Leu Arg
        225                 230                 235                 240

Ala Val Ile Ala Asp Gln Arg Arg Ala Lys
                        245                 250

<210> 4
        <211> 141
        <212> DNA
        <213> Staphylococcus mutans

<400> 4
        atgaaaaaaa cactatcatt aaaaaatgac tttaagaaa ttaagactga tgaattagag      60
attatcattg gcggaagcgg aagcctatca acattttcc ggctgtttaa cagaagtttt     120
```

```
acacaagctt tgggaaaata a                                                  141

<210> 5
<211> 63
<212> DNA
<213> Staphylococcus mutans

<400> 5
agcggaagcc tatcaacatt tttccggctg tttaacagaa gttttacaca agctttggga         60
aaa                                                                       63

<210> 6
<211> 1326
<212> DNA
<213> Staphylococcus mutans

<400> 6
atgaatgaag ccttaatgat actttcaaat ggtttattaa cttatctaac cgttctattt         60
ctcttgtttc tattttctaa ggtaagtaat gtcactttat cgaaaaagga attaactctt        120
ttttcgataa gcaatttttct gataatgatt gctgttacga tggtgaacgt aaacctgttt       180
tatcctgcag agcctcttta ttttatagct ttatcaattt atcttaatag acagaatagt        240
ctttctctaa atatatttta tggtctgctg cctgttgcca gttctgactt gtttaggcgg        300
gcaatcatat tctttatctt ggatggaact caaggaattg taatgggcag tagcattata        360
accacctata tgatcgagtt tgcaggaata gcgctaagtt acctctttct cagtgtgttc        420
aatgttgata ttggtcgact taaagatagt ttgaccaaga tgaaggtcaa aaaacgcttg        480
attccaatga atattactat gcttctatac tacctttaa tacaggtatt gtatgttata         540
gagagttata atgtgatacc gactttaaaa tttcgtaaat ttgtcgttat tgtctatctt        600
attttatttt tgattctgat ctcattttta agccaatata ccaaacaaaa ggttcaaaat        660
gagataatgg cacaaaagga agctcagatt cgaaatatca cccagtatag tcagcaaata        720
gaatctcttt acaaggatat tcgaagtttc cgccatgatt atctgaatat tttaactagc        780
ctcagattag gcattgaaaa taaagattta gctagtattg aaaagattta ccatcaaatc        840
ttagaaaaaa caggacatca attgcaggat acccgttata atatcggcca tctagctaat        900
attcaaaacg atgctgtcaa gggtatcttg tcagcaaaaa tcttagaagc tcagaataaa        960
aagattgctg tcaatgtaga agtctcaagt aaaatacaac tgcctgagat ggagttgctt       1020
gatttcatta ccatactttc tatcttgtgt gataatgcca ttgaggctgc tttcgaatca       1080
ttaaatcctg aaattcagtt agccttttt aagaaaaatg gcagtatagt ctttatcatt        1140
cagaattcca ccaaagaaaa acaaatagat gtgagtaaaa tttttaaaga aaactattcc       1200
```

```
actaaaggct ccaatcgcgg tattggttta gcaaaggtga atcatattct tgaacattat    1260
cccaaaacca gtttacaaac aagcaatcat catcatttat tcaagcaact cctaataata    1320
aaatag                                                                1326
```

<210> 7
<211> 753
<212> DNA
<213> Staphylococcus mutans

<400> 7
```
atgatttcta tttttgtatt ggaagatgat tttttacaac aaggacgtct tgaaaccacc     60
attgcagcta tcatgaaaga aaaaaattgg tcttataaag aattgactat ttttggaaaa    120
ccacaacaac ttattgacgc tatccctgaa aagggcaatc accagatttt cttttggat    180 attgaaatca aaaagagga aagaaagga ctggaagtag ccaatcagat tagacagcat     240
aatcctagtg cagttattgt ctttgtcacg acacattctg agtttatgcc cctcactttt    300
cagtatcagg tatctgcttt ggattttatt gataaatctt gaatcctga ggagttctcc     360 caccgcattg aatcagcgct gtattatgct atggaaaaca gccagaagaa tggtcaatca    420
gaggaacttt ttattttcca ttcatctgaa actcagtttc aggtcccttt tgctgagatt    480
ctgtattttg aacatcttc aacagcccat aagctctgcc tttatactta tgatgaacgg    540
attgaattct acggcagtat gactgacatt gttaaaatgg ataagagact ttttcagtgc    600
catcgctctt ttattgtcaa tcctgccaat attacccgta ttgatcggaa aaaacgcttg    660
gcctattttc gaaataataa gtcttgtctt atttcacgaa ctaagttaac aaaactgaga    720
gctgtgattg ctgatcaaag gagagcaaaa tga                                753
```

<210> 8
<211> 46
<212> PRT
<213> Staphylococcus mutans

<400> 8

```
Met Lys Lys Thr Pro Ser Leu Lys Asn Asp Phe Lys Glu Ile Lys Thr
1               5                   10                  15

Asp Glu Leu Glu Ile Ile Ile Gly Gly Ser Gly Ser Leu Ser Thr Phe
                20                  25                  30

Phe Arg Leu Phe Asn Arg Ser Phe Thr Gln Ala Leu Gly Lys
            35                  40                  45
```

```
<210>  9
<211>  46
<212>  PRT
<213>  Staphylococcus mutans

<400>  9

Met Lys Lys Thr Leu Ser Leu Lys Asn Asp Phe Lys Glu Ile Lys Thr
 1               5                  10                  15

Asp Glu Leu Glu Ile Ile Ile Gly Gly Ser Gly Ser Leu Ser Thr Phe
            20                  25                  30

Phe Arg Leu Phe Asn Arg Ser Phe Thr Gln Ala Leu Gly Lys
            35                  40                  45

<210>  10
<211>  43
<212>  PRT
<213>  Staphylococcus mutans

<400>  10

Met Lys Lys Thr Leu Ser Leu Lys Asn Asp Phe Lys Glu Ile Lys Thr
 1               5                  10                  15

Asp Glu Leu Glu Ile Ile Ile Gly Gly Ser Gly Thr Leu Ser Thr Phe
            20                  25                  30

Phe Arg Leu Phe Asn Arg Ser Phe Thr Gln Ala
            35                  40

<210>  11
<211>  21
<212>  PRT
<213>  Artificial

<220>
<223>  Synthetic signal peptide

<400>  11

Ser Gly Ser Leu Ser Thr Phe Phe Arg Leu Phe Asn Arg Ser Phe Thr
 1               5                  10                  15

Gln Ala Leu Gly Lys
            20

<210>  12
<211>  19
<212>  DNA
<213>  Artificial
```

```
<220>
<223>  Synthetic ComC Forward Primer

<400>  12
agtttttgt ctggctgcg                                                    19

<210>  13
<211>  20
<212>  DNA
<213>  Artificial

<220>
<223>  Synthetic ComC Backward Primer

<400>  13
tccactaaag gctccaatcg                                                  20

<210>  14
<211>  24
<212>  DNA
<213>  Artificial

<220>
<223>  Synthetic ComD Forward Primer

<400>  14
cgctaagtta cctctttctc agtg                                             24

<210>  15
<211>  21
<212>  DNA
<213>  Artificial

<220>
<223>  Synthetic ComD Backward Primer

<400>  15
gcttcctttt gtgccattat c                                                21

<210>  16
<211>  21
<212>  DNA
<213>  Artificial

<220>
<223>  Synthetic ComE Forward Primer

<400>  16
cctgaaaagg gcaatcacca g                                                21

<210>  17
<211>  22
<212>  DNA
<213>  Artificial
```

<220>
<223> Synthetic ComE Backward Primer

<400> 17
gcgatggcac tgaaaaagtc tc                                              22

<210> 18
<211> 2557
<212> DNA
<213> Staphylococcus mutans

<400> 18
acattatgtg tcctaaggaa aatattactt tttcaagaaa atccatgatt ttttcataaa        60
aaatagtata ctaattataa tcaaaaaaag gagatataaa atgaaaaaaa cactatcatt       120
aaaaaatgac tttaagaaa ttaagactga tgaattagag attatcattg gcggaagcgg        180
aagcctatca acatttttcc ggctgtttaa cagaagtttt acacaagctt tgggaaaata       240
agataggcta acattggaat aaaacaaggc tggatttatt attccagcct ttttaaatgt       300
aaaataaaaa tacagggtta aataatcaag tgtgctgtcg tggatgagaa gataaaacta       360
tctcttagag aataggcctc ctctatttta ttattaggag ttgcttgaat aaatgatgat       420
gattgcttgt ttgtaaactg gttttgggat aatgttcaag aatatgattc acctttgcta       480
aaccaatacc gcgattggag cctttagtgg aatagttttc tttaaaaatt ttactcacat       540
ctatttgttt ttctttggtg gaattctgaa tgataaagac tatactgcca ttttttcttaa      600
aaaaggctaa ctgaatttca ggatttaatg attcgaaagc agcctcaatg gcattatcac       660
acaagataga aagtatggta atgaaatcaa gcaactccat ctcaggcagt tgtattttac       720
ttgagacttc tacattgaca gcaatctttt tattctgagc ttctaagatt tttgctgaca       780
agatacccttt gacagcatcg ttttgaatat tagctagatg gccgatatta taacgggtat       840
cctgcaattg atgtcctgtt ttttctaaga tttgatggta aatcttttca atactagcta       900
aatctttatt ttcaatgcct aatctgaggc tagttaaaat attcagataa tcatggcgga       960
aacttcgaat atccttgtaa agagattcta tttgctgact atactgggtg atatttcgaa      1020
tctgagcttc cttttgtgcc attatctcat tttgaacctt ttgtttggta tattggctta      1080
aaaatgagat cagaatcaaa aataaaataa gatagacaat aacgacaaat ttacgaaatt      1140
ttaaagtcgg tatcacatta taactctcta taacatacaa tacctgtatt aaaaggtagt      1200
atagaagcat agtaatattc attggaatca agcgtttttt gaccttcatc ttggtcaaac      1260
tatctttaag tcgaccaata tcaacattga acacactgag aaagaggtaa cttagcgcta      1320
ttcctgcaaa ctcgatcata taggtggtta taatgctact gcccattaca attccttgag      1380

```
ttccatccaa gataaagaat atgattgccc gcctaaacaa gtcagaactg gcaacaggca    1440
gcagaccata aaatatattt agagaaagac tattctgtct attaagataa attgataaag    1500
ctataaaata aagaggctct gcaggataaa acaggtttac gttcaccatc gtaacagcaa    1560
tcattatcag aaaattgctt atcgaaaaa  gagttaattc cttttcgat  aaagtgacat    1620
tacttacctt agaaataga  aacaagagaa atagaacggt tagataagtt aataaaccat    1680
ttgaaagtat cattaaggct tcattcattt tgctctcctt tgatcagcaa tcacagctct    1740
cagttttgtt aacttagttc gtgaaataag acaagactta ttatttcgaa aataggccaa    1800
gcgttttttc cgatcaatac gggtaatatt ggcaggattg acaataaaag agcgatggca    1860
ctgaaaaagt ctcttatcca ttttaacaat gtcagtcata ctgccgtaga attcaatccg    1920
ttcatcataa gtataaaggc agagcttatg ggctgttgaa gatgtttcaa aatacagaat    1980
ctcagcaaaa gggacctgaa actgagtttc agatgaatgg aaaataaaaa gttcctctga    2040
ttgaccattc ttctggctgt tttccatagc ataatacagc gctgattcaa tgcggtggga    2100
gaactcctca ggattcaaag atttatcaat aaaatccaaa gcagatacct gatactgaaa    2160
agtgagggc  ataaactcag aatgtgtcgt gacaaagaca ataactgcac taggattatg    2220
ctgtctaatc tgattggcta cttccagtcc tttctttttcc tcttttttga tttcaatatc    2280
caaaagaaa  atctggtgat tgccctttc  agggatagcg tcaataagtt gttgtggttt    2340
tccaaaaata gtcaattctt tataagacca attttttct  ttcatgatag ctgcaatggt    2400
ggtttcaaga cgtccttgtt gtaaaaaatc atcttccaat acaaaaatag aaatcattat    2460
ttctccttta atcttctatt taggttagct gattaacact atacacagaa aaggtataaa    2520
acgatatcac tcaataaaat ctactaactt aataacc                             2557

<210> 19
<211> 2557
<212> DNA
<213> Staphylococcus mutans

<400> 19
ggttattaag ttagtagatt ttattgagtg atatcgtttt atacctttc  tgtgtatagt      60
gttaatcagc taacctaaat agaagattaa aggagaaata atgatttcta tttttgtatt     120
ggaagatgat ttttacaac  aaggacgtct tgaaccacc  attgcagcta tcatgaaaga     180
aaaaaattgg tcttataaag aattgactat ttttggaaaa ccacaacaac ttattgacgc     240
tatccctgaa aagggcaatc accagatttt cttttggat  attgaaatca aaaagagga     300
aaagaaagga ctggaagtag ccaatcagat tagacagcat aatcctagtg cagttattgt     360
ctttgtcacg acacattctg agtttatgcc cctcactttt cagtatcagg tatctgcttt     420
```

```
ggattttatt gataaatctt tgaatcctga ggagttctcc caccgcattg aatcagcgct    480
gtattatgct atggaaaaca gccagaagaa tggtcaatca gaggaacttt ttattttcca    540
ttcatctgaa actcagtttc aggtcccttt tgctgagatt ctgtatttg aaacatcttc     600
aacagcccat aagctctgcc tttatactta tgatgaacgg attgaattct acggcagtat    660
gactgacatt gttaaaatgg ataagagact ttttcagtgc catcgctctt ttattgtcaa    720
tcctgccaat attacccgta ttgatcggaa aaacgcttg gcctattttc gaaataataa     780
gtcttgtctt atttcacgaa ctaagttaac aaaactgaga gctgtgattg ctgatcaaag    840
gagagcaaaa tgaatgaagc cttaatgata ctttcaaatg gtttattaac ttatctaacc    900
gttctatttc tcttgtttct attttctaag gtaagtaatg tcactttatc gaaaaaggaa    960
ttaactcttt tttcgataag caattttctg ataatgattg ctgttacgat ggtgaacgta    1020
aacctgtttt atcctgcaga gcctctttat tttatagctt tatcaattta tcttaataga    1080
cagaatagtc tttctctaaa tatattttat ggtctgctgc ctgttgccag ttctgacttg    1140
tttaggcggg caatcatatt ctttatcttg gatggaactc aaggaattgt aatgggcagt    1200
agcattataa ccacctatat gatcgagttt gcaggaatag cgctaagtta cctctttctc    1260
agtgtgttca atgttgatat tggtcgactt aaagatagtt tgaccaagat gaaggtcaaa    1320
aaacgcttga ttccaatgaa tattactatg cttctatact acctttaat acaggtattg     1380
tatgttatag agagttataa tgtgataccg actttaaaat ttcgtaaatt tgtcgttatt    1440
gtctatctta ttttatttt gattctgatc tcatttttaa gccaatatac caaacaaaag     1500
gttcaaaatg agataatggc acaaaggaa gctcagattc gaaatatcac ccagtatagt     1560
cagcaaatag aatctcttta caaggatatt cgaagtttcc gccatgatta tctgaatatt    1620
ttaactagcc tcagattagg cattgaaaat aaagatttag ctagtattga aagatttac     1680
catcaaatct tagaaaaaac aggacatcaa ttgcaggata cccgttataa tatcggccat    1740
ctagctaata ttcaaaacga tgctgtcaag ggtatcttgt cagcaaaaat cttagaagct    1800
cagaataaaa agattgctgt caatgtagaa gtctcaagta aaatacaact gcctgagatg    1860
gagttgcttg atttcattac catactttct atcttgtgtg ataatgccat tgaggctgct    1920
ttcgaatcat taaatcctga aattcagtta gcctttttta agaaaaatgg cagtatagtc    1980
tttatcattc agaattccac caaagaaaaa caaatagatg tgagtaaaat ttttaaagaa    2040
aactattcca ctaaaggctc caatcgcggt attggtttag caaaggtgaa tcatattctt    2100
gaacattatc ccaaaccag tttacaaaca agcaatcatc atcatttatt caagcaactc    2160
ctaataataa aatagaggag gcctattctc taagagatag ttttatcttc tcatccacga    2220
```

```
cagcacactt gattatttaa ccctgtattt ttattttaca tttaaaaagg ctggaataat    2280
aaatccagcc ttgttttatt ccaatgttag cctatcttat tttcccaaag cttgtgtaaa    2340
acttctgtta aacagccgga aaaatgttga taggcttccg cttccgccaa tgataatctc    2400
taattcatca gtcttaattt ctttaaagtc atttttaat gatagtgttt ttttcatttt     2460
atatctcctt tttttgatta taattagtat actattttt atgaaaaaat catggatttt     2520
cttgaaaaag taatattttc cttaggacac ataatgt                             2557
```

<210> 20
<211> 47
<212> PRT
<213> Staphylococcus mutans

<400> 20

```
Met Ile Ile Ser Asn Ser Ser Val Leu Ile Ser Leu Lys Ser Phe Phe
1               5                   10                  15

Asn Asp Ser Val Phe Phe Ile Leu Tyr Leu Leu Phe Leu Ile Ile Ile
            20                  25                  30

Ser Ile Leu Phe Phe Met Lys Lys Ser Trp Ile Phe Leu Lys Lys
        35                  40                  45
```

<210> 21
<211> 36
<212> PRT
<213> Staphylococcus mutans

<400> 21

```
Met Ala Leu Ser His Lys Ile Glu Ser Met Val Met Lys Ser Ser Asn
1               5                   10                  15

Ser Ile Ser Gly Ser Cys Ile Leu Leu Glu Thr Ser Thr Leu Thr Ala
            20                  25                  30

Ile Phe Leu Phe
        35
```

<210> 22
<211> 42
<212> PRT
<213> Staphylococcus mutans

<400> 22

Met Ala Glu Thr Ser Asn Ile Leu Val Lys Arg Phe Tyr Leu Leu Thr

```
1               5                   10                  15

Ile Leu Gly Asp Ile Ser Asn Leu Ser Phe Leu Leu Cys His Tyr Leu
            20                  25                  30

Ile Leu Asn Leu Leu Phe Gly Ile Leu Ala
            35                  40
```

<210> 23
<211> 27
<212> PRT
<213> Streptococcus mutans

<400> 23

```
Met Val Cys Cys Leu Leu Pro Val Leu Thr Cys Leu Gly Gly Gln Ser
1               5                   10                  15

Tyr Ser Leu Ser Trp Met Glu Leu Lys Glu Leu
            20                  25
```

<210> 24
<211> 34
<212> PRT
<213> Staphylococcus mutans

<400> 24

```
Met Ala Leu Lys Lys Ser Leu Ile His Phe Asn Asn Val Ser His Thr
1               5                   10                  15

Ala Val Glu Phe Asn Pro Phe Ile Ile Ser Ile Lys Ala Glu Leu Met
            20                  25                  30

Gly Cys
```

<210> 25
<211> 57
<212> PRT
<213> Staphylococcus mutans

<400> 25

```
Met Leu Trp Lys Thr Ala Arg Arg Met Val Asn Gln Arg Asn Phe Leu
1               5                   10                  15

Phe Ser Ile His Leu Lys Leu Ser Phe Arg Ser Leu Leu Leu Arg Phe
            20                  25                  30
```

```
            Cys Ile Leu Lys His Leu Gln Gln Pro Ile Ser Ser Ala Phe Ile Leu
                         35                  40                  45

Met Met Asn Gly Leu Asn Ser Thr Ala
                 50                  55

<210>  26
<211>  80
<212>  PRT
<213>  Staphylococcus mutans

<400>  26

Met Cys Arg Asp Lys Asp Asn Asn Cys Thr Arg Ile Met Leu Ser Asn
            1                5                   10                  15

Leu Ile Gly Tyr Phe Gln Ser Phe Leu Phe Leu Phe Asp Phe Asn
                         20                  25                  30

Ile Gln Lys Glu Asn Leu Val Ile Ala Leu Phe Arg Asp Ser Val Asn
                         35                  40                  45

Lys Leu Leu Trp Phe Ser Lys Asn Ser Gln Phe Phe Ile Arg Pro Ile
                         50                  55                  60

Phe Phe Phe His Asp Ser Cys Asn Gly Gly Phe Lys Thr Ser Leu Leu
            65                  70                  75                  80

<210>  27
<211>  34
<212>  PRT
<213>  Staphylococcus mutans

<400>  27

Met Ile Ala Ala Met Val Val Ser Arg Arg Pro Cys Cys Lys Lys Ser
            1                5                   10                  15

Ser Ser Asn Thr Lys Ile Glu Ile Ile Ser Pro Leu Ile Phe Tyr
                         20                  25                  30

Leu Gly

<210>  28
<211>  480
<212>  DNA
<213>  Staphylococcus mutans

<400>  28
```

```
atggaagaag attttgaaat tgtttttaat aaggttaagc caattgtatg gaaattaagc    60
cgttattact ttattaaaat gtggactcgt gaagattggc aacaagaggg aatgttgatt   120
ttgcaccaat tattaaggga acatccagaa ttagaagagg atgatacaaa attgtatatc   180
tattttaaga cacgtttttc taattacatt aaagatgttt tgcgtcagca agaaagtcag   240
aaacgtcgtt ttaatagaat gtcttatgaa gaagtcggtg agattgaaca ctgtttgtca   300
agtggcggta tgcaattgga tgaatatatt ttatttcgtg atagtttgct tgcatataaa   360
caaggtctga gtactgaaaa gcaagagctg tttgagcgct ggtagcagg agagcacttt    420
ttgggaaggc aaagtatgct gaaagattta cgtaaaaaat taagtgattt taaggaaaaa   480
```

<210> 29
<211> 160
<212> PRT
<213> Staphylococcus mutans

<400> 29

Met Glu Glu Asp Phe Glu Ile Val Phe Asn Lys Val Lys Pro Ile Val
1               5                   10                  15

Trp Lys Leu Ser Arg Tyr Tyr Phe Ile Lys Met Trp Thr Arg Glu Asp
            20                  25                  30

Trp Gln Gln Glu Gly Met Leu Ile Leu His Gln Leu Leu Arg Glu His
        35                  40                  45

Pro Glu Leu Glu Glu Asp Asp Thr Lys Leu Tyr Ile Tyr Phe Lys Thr
    50                  55                  60

Arg Phe Ser Asn Tyr Ile Lys Asp Val Leu Arg Gln Gln Glu Ser Gln
65                  70                  75                  80

Lys Arg Arg Phe Asn Arg Met Ser Tyr Glu Glu Val Gly Glu Ile Glu
                85                  90                  95

His Cys Leu Ser Ser Gly Gly Met Gln Leu Asp Glu Tyr Ile Leu Phe
            100                 105                 110

Arg Asp Ser Leu Leu Ala Tyr Lys Gln Gly Leu Ser Thr Glu Lys Gln
        115                 120                 125

Glu Leu Phe Glu Arg Leu Val Ala Gly Glu His Phe Leu Gly Arg Gln
    130                 135                 140

```
Ser Met Leu Lys Asp Leu Arg Lys Lys Leu Ser Asp Phe Lys Glu Lys
145                 150                 155                 160
```

<210> 30
<211> 680
<212> DNA
<213> Staphylococcus mutans

<400> 30

| | | | | | |
|---|---|---|---|---|---|
| gtaaataaaa | cagccagtta | agatgggaca | tttatgtcct | gttcttaaag | tcttttcgt | 60 |
| tttataataa | ttttattata | aaaggaggtc | atcgtaatag | atggaagaag | attttgaaat | 120 |
| tgtttttaat | aaggttaagc | caattgtatg | gaaattaagc | cgttattact | ttattaaaat | 180 |
| gtggactcgt | gaagattggc | aacaagaggg | aatgttgatt | ttgcaccaat | tattaaggga | 240 |
| acatccagaa | ttagaagagg | atgatacaaa | attgtatatc | tattttaaga | cacgtttttc | 300 |
| taattacatt | aaagatgttt | tgcgtcagca | agaaagtcag | aaacgtcgtt | taatagaat | 360 |
| gtcttatgaa | gaagtcggtg | agattgaaca | ctgtttgtca | agtggcggta | tgcaattgga | 420 |
| tgaatatatt | ttatttcgtg | atagtttgct | tgcatataaa | caaggtctga | gtactgaaaa | 480 |
| gcaagagctg | tttgagcgct | tggtagcagg | agagcacttt | ttgggaaggc | aaagtatgct | 540 |
| gaaagattta | cgtaaaaaat | taagtgattt | taaggaaaaa | tagttaaaaa | gggaaagaat | 600 |
| ggaacatgtg | attgtaccat | tcttttggt | tgaaaattaa | gaaaagttat | tataaattat | 660 |
| tggtttaaca | tgccatatta | | | | | 680 |

<210> 31
<211> 2280
<212> DNA
<213> Staphylococcus mutans

<400> 31

| | | | | | |
|---|---|---|---|---|---|
| atgaaacaag | ttatttatgt | tgtttaatc | gtcatagccg | ttaacattct | cttagagatt | 60 |
| atcaaaagag | taacaaaaag | gggagggaca | gtttcgtcat | ctaatccttt | accagatggg | 120 |
| cagtctaagt | tgttttggcg | cagacattat | aagctagtac | ctcagattga | taccagagac | 180 |
| tgtgggccgg | cagtgctggc | atctgttgca | aagcattacg | gatctaatta | ctctatcgct | 240 |
| tatctgcggg | aactctcaaa | gactaacaag | cagggaacaa | cagctcttgg | cattgttgaa | 300 |
| gctgctaaaa | agttaggctt | tgaaacacgc | tctatcaagg | cggatatgac | gcttttgat | 360 |
| tataatgatt | tgacctatcc | ttttatcgtc | catgtgatta | aaggaaaacg | tctgcagcat | 420 |
| tattatgtcg | tctatggcag | ccagaataat | cagctgatta | ttggagatcc | tgatccttca | 480 |
| gttaaggtga | ctaggatgag | taaggaacgc | tttcaatcag | agtggacagg | ccttgcaatt | 540 |
| ttcctagctc | ctcagcctaa | ctataagcct | cataaaggtg | aaaaaaatgg | tttgtctaat | 600 |

```
ttcttcccgt tgatctttaa gcagaaagct tgatgactt atattatcat agctagcttg      660
attgtgacgc tcattgatat tgtcggatca tactatctcc aaggaatatt ggacgagtac      720
attcctgatc agctgatttc aactttagga atgattacga ttggtctgat aataacctat      780
attatccagc aggtcatggc ttttgcaaaa gaatacctct tggccgtact cagtttgcgt      840
ttagtcattg atgttatcct gtcttatatc aaacatattt ttacgcttcc tatgtctttc      900
tttgcgacaa ggcgaacagg agaaatcacg tctcgtttta cagatgccaa tcagattatt      960
gatgctgtag cgtcaaccat cttttcaatc tttttagata tgactatggt aattttggtt     1020
ggtggggttt tgttggcgca aaacaataac cttttctttc taaccttgct ctccattccg     1080
atttatgcca tcattatttt tgctttcttg aaaccctttg agaaatgaa tcacgaagtg     1140
atggaaagca atgctgtggt aagttcttct atcattgaag atatcaatgg gatggaaacc     1200
attaaatcac tcacaagtga gtccgctcgt tatcaaaaca ttgatagtga atttgttgat     1260
tatttggaga aaaactttaa gctacacaag tatagtgcca ttcaaaccgc attaaaaagc     1320
ggtgctaagc ttatcctcaa tgttgtcatt ctctggtatg gctctcgtct agttatggat     1380
aataaaatct cagttggtca gcttatcacc tttaatgctt tgctgtctta tttctcaaat     1440
ccaattgaaa atattatcaa tctgcaatcc aaactgcagt cagctcgcgt tgccaataca     1500
cgtcttaatg aggtctatct tgtcgaatct gaatttgaaa aagacggcga tttatcagaa     1560
aatagctttt tagatggtga tatttcgttt gaaaatcttt cttataaata tggatttggg     1620
cgagatacct tatcagatat taatttatca atcaaaaaag gctccaaggt cagtctagtt     1680
ggagccagtg gttctggtaa acaactttg gctaaactga ttgtcaattt ctacgagcct     1740
aacaagggga ttgttcgaat caatggcaat gatttaaaag ttattgataa gacagctttg     1800
cggcggcata ttagctattt gccgcaacag gcctatgttt ttagtggctc tattatggat     1860
aatctcgttt taggagctaa agaaggaacg agtcaggaag acattattcg tgcttgtgaa     1920
attgctgaaa tccgctcgga cattgaacaa atgcctcagg gctatcagac agagttatca     1980
gatggtgccg gtatttctgg cggtcaaaaa cagcggattg ctttagctag ggccttatta     2040
acacaggcac cggttttgat tctggatgaa gccaccagca gtcttgatat tttgacagaa     2100
aagaaaatta tcagcaatct cttacagatg acggagaaaa caataatttt tgttgcccac     2160
cgcttaagca tttcacagcg tactgacgaa gtcattgtca tggatcaggg aaaaattgtt     2220
gaacaaggca ctcataagga acttttagct aagcaaggtt tctattataa cctgtttaat     2280
```

<210> 32
<211> 760

<212> PRT
<213> Staphylococcus mutans

<400> 32

Met Lys Gln Val Ile Tyr Val Val Leu Ile Val Ile Ala Val Asn Ile
1               5                   10                  15

Leu Leu Glu Ile Ile Lys Arg Val Thr Lys Arg Gly Gly Thr Val Ser
                20                  25                  30

Ser Ser Asn Pro Leu Pro Asp Gly Gln Ser Lys Leu Phe Trp Arg Arg
            35                  40                  45

His Tyr Lys Leu Val Pro Gln Ile Asp Thr Arg Asp Cys Gly Pro Ala
        50                  55                  60

Val Leu Ala Ser Val Ala Lys His Tyr Gly Ser Asn Tyr Ser Ile Ala
65                  70                  75                  80

Tyr Leu Arg Glu Leu Ser Lys Thr Asn Lys Gln Gly Thr Thr Ala Leu
                85                  90                  95

Gly Ile Val Glu Ala Ala Lys Lys Leu Gly Phe Glu Thr Arg Ser Ile
            100                 105                 110

Lys Ala Asp Met Thr Leu Phe Asp Tyr Asn Asp Leu Thr Tyr Pro Phe
        115                 120                 125

Ile Val His Val Ile Lys Gly Lys Arg Leu Gln His Tyr Tyr Val Val
    130                 135                 140

Tyr Gly Ser Gln Asn Asn Gln Leu Ile Ile Gly Asp Pro Asp Pro Ser
145                 150                 155                 160

Val Lys Val Thr Arg Met Ser Lys Glu Arg Phe Gln Ser Glu Trp Thr
                165                 170                 175

Gly Leu Ala Ile Phe Leu Ala Pro Gln Pro Asn Tyr Lys Pro His Lys
            180                 185                 190

Gly Glu Lys Asn Gly Leu Ser Asn Phe Phe Pro Leu Ile Phe Lys Gln
        195                 200                 205

Lys Ala Leu Met Thr Tyr Ile Ile Ala Ser Leu Ile Val Thr Leu
    210                 215                 220

```
Ile Asp Ile Val Gly Ser Tyr Tyr Leu Gln Gly Ile Leu Asp Glu Tyr
225                 230                 235                 240

Ile Pro Asp Gln Leu Ile Ser Thr Leu Gly Met Ile Thr Ile Gly Leu
                245                 250                 255

Ile Ile Thr Tyr Ile Ile Gln Gln Val Met Ala Phe Ala Lys Glu Tyr
            260                 265                 270

Leu Leu Ala Val Leu Ser Leu Arg Leu Val Ile Asp Val Ile Leu Ser
        275                 280                 285

Tyr Ile Lys His Ile Phe Thr Leu Pro Met Ser Phe Phe Ala Thr Arg
    290                 295                 300

Arg Thr Gly Glu Ile Thr Ser Arg Phe Thr Asp Ala Asn Gln Ile Ile
305                 310                 315                 320

Asp Ala Val Ala Ser Thr Ile Phe Ser Ile Phe Leu Asp Met Thr Met
                325                 330                 335

Val Ile Leu Val Gly Gly Val Leu Leu Ala Gln Asn Asn Asn Leu Phe
            340                 345                 350

Phe Leu Thr Leu Leu Ser Ile Pro Ile Tyr Ala Ile Ile Ile Phe Ala
        355                 360                 365

Phe Leu Lys Pro Phe Glu Lys Met Asn His Glu Val Met Glu Ser Asn
    370                 375                 380

Ala Val Val Ser Ser Ser Ile Ile Glu Asp Ile Asn Gly Met Glu Thr
385                 390                 395                 400

Ile Lys Ser Leu Thr Ser Glu Ser Ala Arg Tyr Gln Asn Ile Asp Ser
                405                 410                 415

Glu Phe Val Asp Tyr Leu Glu Lys Asn Phe Lys Leu His Lys Tyr Ser
            420                 425                 430

Ala Ile Gln Thr Ala Leu Lys Ser Gly Ala Lys Leu Ile Leu Asn Val
        435                 440                 445

Val Ile Leu Trp Tyr Gly Ser Arg Leu Val Met Asp Asn Lys Ile Ser
450                 455                 460
```

```
Val Gly Gln Leu Ile Thr Phe Asn Ala Leu Leu Ser Tyr Phe Ser Asn
465                 470                 475                 480

Pro Ile Glu Asn Ile Ile Asn Leu Gln Ser Lys Leu Gln Ser Ala Arg
                485                 490                 495

Val Ala Asn Thr Arg Leu Asn Glu Val Tyr Leu Val Glu Ser Glu Phe
            500                 505                 510

Glu Lys Asp Gly Asp Leu Ser Glu Asn Ser Phe Leu Asp Gly Asp Ile
        515                 520                 525

Ser Phe Glu Asn Leu Ser Tyr Lys Tyr Gly Phe Gly Arg Asp Thr Leu
    530                 535                 540

Ser Asp Ile Asn Leu Ser Ile Lys Lys Gly Ser Lys Val Ser Leu Val
545                 550                 555                 560

Gly Ala Ser Gly Ser Gly Lys Thr Thr Leu Ala Lys Leu Ile Val Asn
                565                 570                 575

Phe Tyr Glu Pro Asn Lys Gly Ile Val Arg Ile Asn Gly Asn Asp Leu
            580                 585                 590

Lys Val Ile Asp Lys Thr Ala Leu Arg Arg His Ile Ser Tyr Leu Pro
        595                 600                 605

Gln Gln Ala Tyr Val Phe Ser Gly Ser Ile Met Asp Asn Leu Val Leu
    610                 615                 620

Gly Ala Lys Glu Gly Thr Ser Gln Glu Asp Ile Ile Arg Ala Cys Glu
625                 630                 635                 640

Ile Ala Glu Ile Arg Ser Asp Ile Glu Gln Met Pro Gln Gly Tyr Gln
                645                 650                 655

Thr Glu Leu Ser Asp Gly Ala Gly Ile Ser Gly Gly Gln Lys Gln Arg
            660                 665                 670

Ile Ala Leu Ala Arg Ala Leu Leu Thr Gln Ala Pro Val Leu Ile Leu
        675                 680                 685

Asp Glu Ala Thr Ser Ser Leu Asp Ile Leu Thr Glu Lys Lys Ile Ile
690                 695                 700
```

```
Ser Asn Leu Leu Gln Met Thr Glu Lys Thr Ile Ile Phe Val Ala His
705                 710                 715                 720

Arg Leu Ser Ile Ser Gln Arg Thr Asp Glu Val Ile Val Met Asp Gln
                725                 730                 735

Gly Lys Ile Val Glu Gln Gly Thr His Lys Glu Leu Leu Ala Lys Gln
            740                 745                 750

Gly Phe Tyr Tyr Asn Leu Phe Asn
            755                 760

<210>  33
<211>  900
<212>  DNA
<213>  Staphylococcus mutans

<400>  33
atggatccta aattttaca  aagtgcagaa  ttttatagga  gacgctatca  taattttgcg    60
acactattaa ttgttccttt ggtctgcttg  attatcttct  tggtcatatt  cctttgtttt   120
gctaaaaaag aaattacagt gatttctact  ggtgaagttg  caccaacaaa  ggttgtagat   180
gttatccaat cttacagtga cagttcaatc  attaaaaata  atttagataa  taatgcagct   240
gttgagaagg gagacgtttt aattgaatat  tcagaaaatg  ccagtccaaa  ccgtcagact   300
gaacaaaaga atattataaa agaaagacaa  aaacgagaag  agaaggaaaa  gaaaaaacac   360
caaaagagca agaaaaagaa gaagtctaag  agcaagaaag  cttccaaaga  taagaaaaag   420
aaatcgaaag acaaggaaag cagctctgac  gatgaaaatg  agacaaaaaa  ggtttcgatt   480
tttgcttcag aagatggtat tattcatacc  aatcccaaat  atgatggtgc  aatattatt   540
ccgaagcaaa ccgagattgc tcaaatctat  cctgatattc  aaaaaacaag  aaaagtgtta   600
atcacctatt atgcttcttc tgatgatgtt  gtttctatga  aaaaggggca  aaccgctcgt   660
ctttccttgg aaaaaagggg aaatgacaag  gttgttattg  aaggaaaaat  taacaatgtc   720
gcttcatcag caactactac taaaaaagga  aatctcttta  aggttactgc  caaagtaaag   780
gtttctaaga aaaatagcaa actcatcaag  tatggtatga  caggcaagac  agtcactgtc   840
attgataaaa agacttattt tgattatttc  aaagataaat  tactgcataa  aatggataat   900

<210>  34
<211>  300
<212>  PRT
<213>  Staphylococcus mutans

<400>  34
```

```
Met Asp Pro Lys Phe Leu Gln Ser Ala Glu Phe Tyr Arg Arg Arg Tyr
1               5                   10                  15

His Asn Phe Ala Thr Leu Leu Ile Val Pro Leu Val Cys Leu Ile Ile
            20                  25                  30

Phe Leu Val Ile Phe Leu Cys Phe Ala Lys Lys Glu Ile Thr Val Ile
            35                  40                  45

Ser Thr Gly Glu Val Ala Pro Thr Lys Val Val Asp Val Ile Gln Ser
50                      55                  60

Tyr Ser Asp Ser Ser Ile Ile Lys Asn Asn Leu Asp Asn Asn Ala Ala
65                  70                  75                  80

Val Glu Lys Gly Asp Val Leu Ile Glu Tyr Ser Glu Asn Ala Ser Pro
                85                  90                  95

Asn Arg Gln Thr Glu Gln Lys Asn Ile Ile Lys Glu Arg Gln Lys Arg
            100                 105                 110

Glu Glu Lys Glu Lys Lys Lys His Gln Lys Ser Lys Lys Lys Lys Lys
            115                 120                 125

Ser Lys Ser Lys Lys Ala Ser Lys Asp Lys Lys Lys Ser Lys Asp
            130                 135                 140

Lys Glu Ser Ser Ser Asp Asp Glu Asn Glu Thr Lys Lys Val Ser Ile
145                 150                 155                 160

Phe Ala Ser Glu Asp Gly Ile Ile His Thr Asn Pro Lys Tyr Asp Gly
                165                 170                 175

Ala Asn Ile Ile Pro Lys Gln Thr Glu Ile Ala Gln Ile Tyr Pro Asp
                180                 185                 190

Ile Gln Lys Thr Arg Lys Val Leu Ile Thr Tyr Tyr Ala Ser Ser Asp
            195                 200                 205

Asp Val Val Ser Met Lys Lys Gly Gln Thr Ala Arg Leu Ser Leu Glu
        210                 215                 220

Lys Lys Gly Asn Asp Lys Val Val Ile Glu Gly Lys Ile Asn Asn Val
225                 230                 235                 240
```

```
Ala Ser Ser Ala Thr Thr Thr Lys Lys Gly Asn Leu Phe Lys Val Thr
                245                 250                 255

Ala Lys Val Lys Val Ser Lys Lys Asn Ser Lys Leu Ile Lys Tyr Gly
                260                 265                 270

Met Thr Gly Lys Thr Val Thr Val Ile Asp Lys Lys Thr Tyr Phe Asp
                275                 280                 285

Tyr Phe Lys Asp Lys Leu Leu His Lys Met Asp Asn
                290                 295                 300

<210> 35
<211> 20
<212> PRT
<213> Artificial

<220>
<223> Synthetic peptide IH-1

<400> 35

Gly Ser Leu Ser Thr Phe Phe Arg Leu Phe Asn Arg Ser Phe Thr Gln
1               5                   10                  15

Ala Leu Gly Lys
            20

<210> 36
<211> 20
<212> PRT
<213> Artificial

<220>
<223> Synthetic peptide IH-2

<400> 36

Ser Gly Ser Leu Ser Thr Phe Phe Arg Leu Phe Asn Arg Ser Phe Thr
1               5                   10                  15

Gln Ala Leu Gly
            20

<210> 37
<211> 20
<212> PRT
<213> Artificial

<220>
<223> Synthetic peptide B1
```

```
<400> 37

Ser Ser Leu Ser Thr Phe Phe Arg Leu Phe Asn Arg Ser Phe Thr Gln
1               5                   10                  15

Ala Leu Gly Lys
            20

<210> 38
<211> 20
<212> PRT
<213> Artificial

<220>
<223> Synthetic peptide C1

<400> 38

Ser Gly Leu Ser Thr Phe Phe Arg Leu Phe Asn Arg Ser Phe Thr Gln
1               5                   10                  15

Ala Leu Gly Lys
            20

<210> 39
<211> 20
<212> PRT
<213> Artificial

<220>
<223> Synthetic peptide D1

<400> 39

Ser Gly Ser Ser Thr Phe Phe Arg Leu Phe Asn Arg Ser Phe Thr Gln
1               5                   10                  15

Ala Leu Gly Lys
            20

<210> 40
<211> 20
<212> PRT
<213> Artificial

<220>
<223> Synthetic peptide E1

<400> 40

Ser Gly Ser Leu Thr Phe Phe Arg Leu Phe Asn Arg Ser Phe Thr Gln
1               5                   10                  15
```

```
Ala Leu Gly Lys
            20

<210>  41
<211>  20
<212>  PRT
<213>  Artificial

<220>
<223>  Synthetic peptide F1

<400>  41

Ser Gly Ser Leu Ser Thr Phe Phe Arg Leu Phe Asn Arg Ser Phe Thr
1               5                   10                  15

Gln Ala Leu Lys
            20

<210>  42
<211>  20
<212>  PRT
<213>  Artificial

<220>
<223>  Synthetic peptide G1

<400>  42

Ser Gly Ser Leu Ser Thr Phe Phe Arg Leu Phe Asn Arg Ser Phe Thr
1               5                   10                  15

Gln Ala Gly Lys
            20

<210>  43
<211>  20
<212>  PRT
<213>  Artificial

<220>
<223>  Synthetic peptide H1

<400>  43

Ser Gly Ser Leu Ser Thr Phe Phe Arg Leu Phe Asn Arg Ser Phe Thr
1               5                   10                  15

Gln Leu Gly Lys
            20

<210>  44
```

```
<211>  20
<212>  PRT
<213>  Artificial

<220>
<223>  Synthetic peptide A2

<400>  44

Ser Gly Ser Leu Ser Thr Phe Phe Arg Leu Phe Asn Arg Ser Phe Thr
1               5                   10                  15

Ala Leu Gly Lys
            20

<210>  45
<211>  21
<212>  PRT
<213>  Artificial

<220>
<223>  Synthetic peptide B2

<400>  45

Ser Gly Ser Leu Ser Thr Phe Phe Val Leu Phe Asn Arg Ser Phe Thr
1               5                   10                  15

Gln Ala Leu Gly Lys
            20

<210>  46
<211>  21
<212>  PRT
<213>  Artificial

<220>
<223>  Synthetic peptide C2

<400>  46

Ser Gly Ser Leu Ser Thr Phe Phe Ala Leu Phe Asn Arg Ser Phe Thr
1               5                   10                  15

Gln Ala Leu Gly Lys
            20

<210>  47
<211>  21
<212>  PRT
<213>  Artificial

<220>
<223>  Synthetic peptide D2
```

<400> 47

Ser Gly Ser Leu Ser Thr Phe Phe Arg Leu Phe Asn Val Ser Phe Thr
1               5                   10                  15

Gln Ala Leu Gly Lys
            20

<210> 48
<211> 21
<212> PRT
<213> Artificial

<220>
<223> Synthetic peptide E2

<400> 48

Ser Gly Ser Leu Ser Thr Phe Phe Arg Leu Phe Asn Ala Ser Phe Thr
1               5                   10                  15

Gln Ala Leu Gly Lys
            20

<210> 49
<211> 21
<212> PRT
<213> Artificial

<220>
<223> Synthetic peptide F2

<400> 49

Ser Gly Ser Leu Ser Thr Phe Phe Arg Leu Phe Asn Arg Ser Phe Thr
1               5                   10                  15

Gln Ala Leu Gly Val
            20

<210> 50
<211> 21
<212> PRT
<213> Artificial

<220>
<223> Synthetic peptide G2

<400> 50

Ser Gly Ser Leu Ser Thr Phe Phe Arg Leu Phe Asn Arg Ser Phe Thr
1               5                   10                  15

```
Gln Ala Leu Gly Ala
         20

<210>  51
<211>  18
<212>  PRT
<213>  Artificial

<220>
<223>  Synthetic peptide B3

<400>  51

Ser Gly Thr Leu Ser Thr Phe Phe Arg Leu Phe Asn Arg Ser Phe Thr
1               5                   10                  15

Gln Ala

<210>  52
<211>  25
<212>  DNA
<213>  Artificial

<220>
<223>  Synthetic P1-HK13 primer

<400>  52
cacaacaact tattgacgct atccc                                          25

<210>  53
<211>  30
<212>  DNA
<213>  Artificial

<220>
<223>  Synthetic P2-HK13 primer

<400>  53
ggcgcgccaa ctggcaacag gcagcagacc                                     30

<210>  54
<211>  29
<212>  DNA
<213>  Artificial

<220>
<223>  Synthetic P3-HK13 primer

<400>  54
ggccggcctc aaaacgatgc tgtcaaggg                                      29

<210>  55
```

CERTIFICATE OF CORRECTION (continued)
U.S. Pat. No. 7,597,895 B2

```
<211> 21
<212> DNA
<213> Artificial

<220>
<223> Synthetic P4-HK13 primer

<400> 55
agattatcat tggcggaagc g                                          21

<210> 56
<211> 30
<212> DNA
<213> Artificial

<220>
<223> Synthetic Erm-19 primer

<400> 56
ggcgcgcccc gggcccaaaa tttgtttgat                                 30

<210> 57
<211> 30
<212> DNA
<213> Artificial

<220>
<223> Synthetic Erm-20 primer

<400> 57
ggccggccag tcggcagcga ctcatagaat                                 30
```

Signed and Sealed this

Nineteenth Day of January, 2010

David J. Kappos
*Director of the United States Patent and Trademark Office*